United States Patent
Kay et al.

(10) Patent No.: US 6,703,482 B2
(45) Date of Patent: *Mar. 9, 2004

(54) SRC SH3 BINDING PEPTIDES AND METHODS OF ISOLATING AND USING SAME

(75) Inventors: Brian K. Kay, Chapel Hill, NC (US); Andrew B. Sparks, Carrboro, NC (US); Judith M. Thorn, Carrboro, NC (US); Lawrence A. Quilliam, Chapel Hill, NC (US); Channing J. Der, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/938,315

(22) Filed: Aug. 23, 2001

(65) Prior Publication Data

US 2002/0091085 A1 Jul. 11, 2002

Related U.S. Application Data

(63) Continuation of application No. 08/278,865, filed on Jul. 22, 1994, now Pat. No. 6,303,574.

(51) Int. Cl.[7] .................................................. C07K 7/08
(52) U.S. Cl. .................... 530/324; 530/325; 530/300; 514/15; 514/14; 514/13; 514/12
(58) Field of Search ....................... 514/15–12; 530/324, 530/325, 300

(56) References Cited

U.S. PATENT DOCUMENTS 5,541,109 A 7/1996 Searfoss .................. 435/252.3

FOREIGN PATENT DOCUMENTS

WO WO 93/18054 9/1993
WO WO 95/24419 9/1995

OTHER PUBLICATIONS

Barfod et al., 1993, "Cloning and expression of a human CDC42 GTPase–activating protein reveals a functional SH3–binding domain," J. Biol. Chem. 268:26059–26062.
Blond–Elguindi et al., 1993, "Affinity panning of a library of peptides displayed on bacteriophages reveals the binding specificity of BiP," Cell 75:717–728.
Brugge, 1993, "New intracellular targets for therapeutic drug design," Science 260:918–919.
Buchwald et al., 1980, "Long–term, continuous intravenous heparin administration by an implantable infusion pump in ambulatory patients with recurrent venous thrombosis," Surgery 88:507–516.
Buday and Downward, 1993, "Epidermal growth factor regulates p21$^{res}$ through the formation of a complex of receptor, Grb2 adapter protein, and Sos nucleotide exchange factor," Cell 73:611–620.
Burns et al., 1992, "Temperature–sensitive polioviruses containing mutations in RNA polymerase," Virology 189:568–582.
Carmo et al., 1993, "Physical association of the cytopolasmic domain of CD2 with the tyrosine kinases p56$^{lck}$ and p59$^{fyn}$," Eur. J. Immunol. 23:2196–2201.
Cartwright et al., 1987, "Cell transformation by pp60$^{c-src}$ mutated in the carboxy–terminal regulatory domain," Cell 49:83–91.
Cooper et al., 1986, "Tyr$^{527}$ is phosphorylated in pp60$^{c-src}$: implications for regulation," Science 231:1431–1434.
Dedman et al., 1993, "Selection of targeted biological modifiers from a bacteriophage library of random peptides," J. Biol. Chem. 268:23025–23030.
Donovan and Koretzky, 1993, "CD45 and the immune response," J. Am. Soc. Nephrol. 4:976–985.
During et al., 1989, "Controlled release of dopamine from a polymeric brain implant: in vivo characterization," Ann. Neurol. 25:351–356.
Flynn et al., 1993, "Identification and sequence analysis of cDNAs encoding a 110–kilodalton actin filament–associated pp60$^{src}$ substrate," Mol. Cell. Biol. 13:7892–7900.
Fumagalli et al., 1994, "A target for src in mitosis," Nature 368(6474):871–874.
Hall, 1994, "Evidence that c–src is involved in the process of osteoclastic bone resorption," Biochem. Biophys. Res. Commun. 199:1237–44.
Hershfield and Buckley, 1987, "Treatment of adenosine deaminase deficiency with polyethylene glycol–modified adenosine deaminase," N. Engl. J. Med. 316:589–596.
Hirai and Varmus, 1990, "Site–directed mutagenesis of the SH2– and SH3–coding domains of c–src produces varied phenotypes, including oncogenic activation of p60$^{c-src}$," Mol. Cell. Biol. 10:1307–1318.
Ho et al., 1986, "Clinical pharmacology of polyethylene glycol–l–asparaginase," Drug. Metab. Dispos. 14:349–352.
Howard et al., 1989, "Intracerebral drug delivery in rats with lesion–induced memory deficits," J. Neurosurg. 71:105–112.

(List continued on next page.)

*Primary Examiner*—T. D. Wessendorf
(74) *Attorney, Agent, or Firm*—Morgan & Finnegan, L.L.P.; Eugene Moroz

(57) ABSTRACT

Peptides having general and specific binding affinities for the Src homology region 3 (SH3) domains of proteins are disclosed in the present invention. In particular, SH3 binding peptides have been isolated from three phage-displayed random peptide libraries which had been screened for isolates that bind to bacterial fusion proteins of SH3 domains and glutathione S-transferase (GST). Preferred peptides are disclosed having a core 7-mer sequence (preferably, a consensus motif) and two or more, preferably at least six, additional amino acid residues flanking the core sequence, for a total length of 9, preferably at least 13, amino acid residues and no more than about 45 amino acid residues. Such peptides manifest preferential binding affinities for certain SH3 domains. The preferred peptides exhibit specific binding affinities for the Src-family of proteins. In vitro and in vivo results are presented which demonstrate the biochemical activity of such peptides.

1 Claim, 12 Drawing Sheets

OTHER PUBLICATIONS

Figure 1:
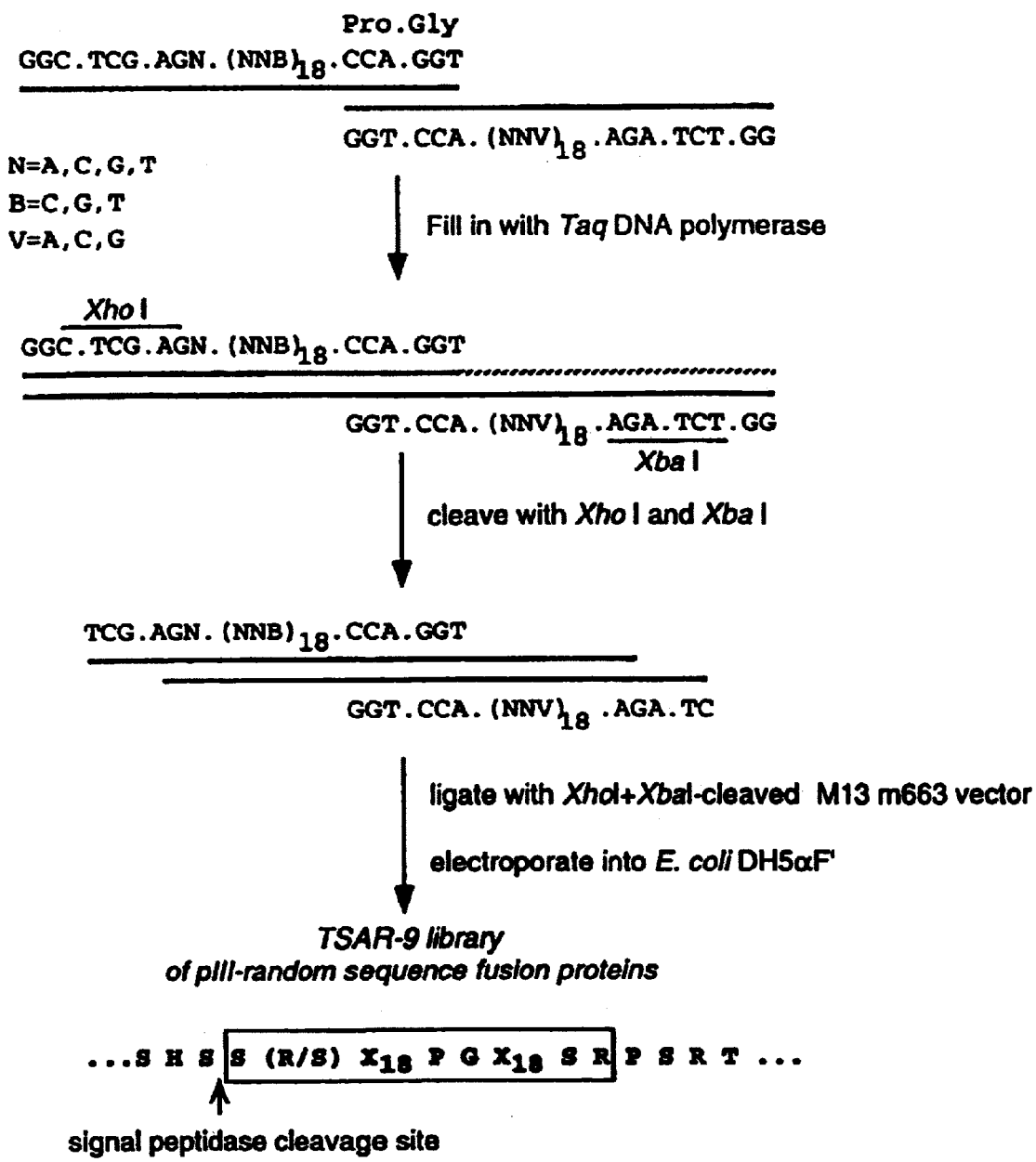

Klinz and Maness, 1992, "Tyrosine kinase pp60$^{c-src}$ in nerve growth cones and developing brain: topographical and functional analysis," Neuroprotocols (a companion to Neuroscience) 1(3):224–231.

Kmiecik et al., 1987, "Activation and suppression of pp60$^{c-src}$ transforming ability by mutation of its primary sites of tyrosine phosphorylation," Cell 49:65–73.

Kopecek and Duncan, 1987, "Targetable polymeric pro-drugs," J. Controlled Release 6:315–327.

Koyama et al., 1993, "$^1$H and $^{15}$H assignments and secondary structure of the P13K SH3 domain," FEBS 324:93–98.

Kraulis, 1991, "Molscript: a program to produce both detailed and schematic plots of protein structures," J. Appl. Crystallogr. 24:946–950.

Langer and Peppas, 1983, "Chemical and physical structure of polymers as carriers for controlled release of bioactive agents: a review," JMS—Rev. Macromol. Chem. Phys. 23:61–126.

Langer, 1990, "New methods of drug delivery," Science 249:1527–1533.

Levy et al, 1985, "Inhibition of calcification of bioprosthetic heart valves by local controlled-release diphosphonate," Science 228:190–192.

Liu et al., 1993, "Regulation of c–src tyrosine kinase activity by the src SH2 domain," Oncogene 8:1119–1126.

Lopez–Berestein, 1989, in *Liposomes in the Therapy of Infectious Disease and Cancer*, Lopez–Berestein and Fidler (eds.), Liss, New York pp. 317–327.

Lowell et al., 1994, "Functional overlap in the src gene family: inactivation of hck and fgr impairs natural immunity," Genes and Development 8:387–398.

Matsuda et al., 1990, "Binding of transforming protein, P47$^{gag-crk}$, to a broad range of phosphotyrosine–containing proteins," Science 248:1537–1539.

Matsumura and Maeda, 1986, "A new concept for macromolecular therapeutics in cancer chemotherapy: mechanism of tumoritropic accumulation of proteins and the antitumor agent Smancs," Cancer Res. 46:6387–6392.

Mayer and Baltimore, 1993, "Signalling through SH2 and SH3 domains," Trends Cell. Biol. 8:8–13.

Paxton et al., 1994, "The angiotensin II AT$_1$ receptor is tyrosine and serine phosphorylated and can serve as a substrate for the src family of tyrosine kinases," Biochem. Biophys. Res. Commun. 200(1):260–267.

Piwnica–Worms et al., 1987, "Tyrosine phosphorylation regulates the biochemical and biological properties of pp60$^{c-src}$," Cell 49:75–82.

Ren et al., 1994, "Signal transduction via CD40 involves activation of lyn kinase and phosphatidylinositol–3–kinase, and phosphorylation of phospholipase Cγ2," J. Exp. Med. 179(2):673–680.

Roussel et al., 1991, "Selective binding of activated pp60$^{c-src}$ by an immobilized synthetic phosphopeptide modeled on the carboxyl terminus of pp60$^{c-src}$," Proc. Natl. Acad. Sci. U S A 88:10696–700.

Saudek et al., 1989, "A preliminary trial of the programmable implantable medication system for insulin delivery," N. Engl. J. Med. 321:574–579.

Scott and Smith, 1990, "Searching for peptide ligands with an epitope library," Science 249:386–390.

Sefton, 1987, "Implantable pumps," CRC Crit. Ref. Biomed. Eng. 14:201–240.

Smith and Johnson, 1988, "Single–step purification of polypeptides expressed in *Escherichia coli* as fusions with glutathione S–transferase," Gene. 67:31–40.

Soriano et al. "Targeted disruption of the c–src proto–oncogene leads to osteopetrosis in mice," Cell 54:693–702.

Taylor and Shalloway, 1994, "An RNA–binding protein associated with src through its SH2 and SH3 domains in mitosis," Nature 368:876–871.

Thony–Meyer et al., 1992, "Prokaryotic polyprotein precursors," FEBS 307:62–65.

Treat et al., 1989, Liposomes in the Therapy of Infectious Disease and Cancer, Lopez–Berestein and Fidler (eds.), Liss, New York (1989) pp. 353–365.

Umemori et al., 1992, "Specific expressions of fyn and lyn, lymphocyte antigen receptor–associated tyrosine kinases, in the central nervous system," Mol. Brain Res. 16:303–310.

Straus & Weiss, 1992, "Genetic evidence for the involvement of the lck tyrosine kinase in signal transduction through the T cell antigen receptor," Cell 70:585–593.

Appleby et al., 1992, "Defective T cell receptor signalling in mice lacking the thymic isoform of p59$^{fyn}$," Cell 70:751–763.

The Journal of Biological Chemistry, vol. 268, No. 3, Jan. 25, 1993, pp. 1775–1779, Guochang Zhu, et al., "Direct Analysis Of The Binding Of The abl Src Homology 2 Domain To The Activated Epidermal Growth Factor Receptor".

Science, vol. 258, Dec. 4, 1992, Nongtao Yu, et al., "Solution Structure Of The SH3 Domain Of Src And Identification Of Its Ligand–Binding Site", pp. 1665–1668.

FEBS Letters, vol. 324, No. 1, pp. 87–92, Jun. 1993, Hongtao Yu, et al., "1H and 15N Assignments And Secondary Structure Of The Src SH3 Domain".

Cell, vol. 76, pp. 933–945, Mar. 11, 1994, Nongtao Yu, et al., "Structural Basis For The Binding Of Proline–Rich Peptides To SH3 Domains".

Molecular and Cellular Biology, Oct. 1991, pp. 5113–5124, vol. 11, No. 10, Hong Wu, et al. "Identification And Characterization Of A Novel Cytoskeleton–Associated pp60src Substrate".

The Journal of Cell Biology, vol. 120, 1993, pp. 1417–1426, Hong Wu, et al., "Contactin, An 80/85–Kilodalton pp60src Substrate, Is A Filamentous Actin–Binding Protein Enriched In The Cell Cortex".

The Journal of Biological Chemistry, vol. 268, No. 20, Jul. 15, 1993, pp. 14956–14963, Zhigang Weng, et al., "Detection Of Src Homology 3–Binding Proteins, Including Paxillin, In Normal And v–Src–Transformed Balb/c 3T3 Cells".

Journal of Virology, Apr. 1992, pp. 1866–1874, vol. 66, No. 4, David S. Wages, et al., "Mutations In The SH3 Domain Of The src Oncogene Which Decrease Association Of Phosphatidylinositol 3'–Kinase Activity With pp60v–src And Alter Cellular Morphology".

Molecular and Cellular Biology, Dec. 1992, pp. 5485–5498, vol. 12, No. 12, Thomas F. Unger, et al., "Biochemical And Cytological Changes Associated With Expression Of Deregulated pp60src In Xenopus Oocytes".

Molecular and Cellular Biology, Jul. 1993, pp. 4409–4415, vol. 13, No. 7, Shinya Tamaka, et al., "Both The SH2 and SH3 Domains Of Human CRK Protein Are Required For Neuronal Differentiation Of PC12 Cells".

The EMBO Journal, vol. 12, No. 7, pp. 2625–2634, 1993, Giulio Superti–Furga, et al., "CSK Inhibition Of c–Src Activity Requires Both The SH2 and SH3 Domains of Src".

Molecular and Cellular Biology, Sep. 1993, pp. 5500–5512, vol. 13, No. 9, Ki–Ling Suen, et al., "Molecular Cloning Of The Mouse grb2 Gene: Differential Interaction Of The Grb2 Adaptor Protein With Epidermal Growth Factor And A Nerve Growth Factor Receptors".

J. Mol. Biol. 1992, vol. 225, pp. 577–583, Charles W. Stephen, et al., "Mutant Conformation of p53 Precise Epitope Mapping Using A Filamentous Phage Epitope Library".

The Journal of Biological Chemistry, vol. 269, No. 39, Sep. 30, 1994, Andrew B. Sparks, et al., "Identification And Characterization Of Src SH3 Ligands From Phage Displayed Random Peptide Libraries", pp. 23853–23856.

Gene, vol. 67, 1988, pp. 31–40, "Single–Step Purification Of Polypeptides Expressed In *Escherichia coli* As Fusions With Glutathione S–Transferase".

Cell, vol. 73, pp. 169–177, Apr. 9, 1993, Michael A. Simon, et al., "AN SH3–SH2–SH3 Protein Is Required For p21res1 Activation And Binds To Sevenless And SOS Proteins In Vitro".

Molecular and Cellular Biology, Apr. 1992, vol. 12, No. 4, pp. 1835–1845, Cynthia Seidel–Dugan, et al., "Effects Of SH2 and SH3 Delections On The Functional Activities Of Wild–Type And Transforming Variants Of c–Src".

Current Opinion in Genetics and Development, 1994, vol. 4, pp. 25–30, Joseph Schlessinger, "SH2/SH3 Signaling Proteins".

Proc. Natl. Acad. Sci. USA, vol. 74, No. 12, pp. 5463–5467, Dec. 1977, F. Sanger, et al., "DNA Sequencing With Chain–Terminating Inhibitors".

Proc. Natl. Acad. Sci. USA, vol. 89, pp. 5398–5402, Jun. 1992, Jamie K. Scott, et al., "A Family Of Concanavalin A–Binding Peptides From A Hexapeptide Epitope Library".

Nature, vol. 363, May 6, 1993, Maria Rozakis–Adcock, et al., "The SH2 and SH3 Domains Of Mammalian Grb2 Couple The EGF Receptor To The Ras Activator mSos1", pp. 83–85.

Nature, vol. 364, Aug. 26, 1993, Robert B, Russell, et al., "An SH2–SH3 Domain Hybrid", p. 765.

Oncogene, 1992, vol. 7, pp. 1949–1955, Pamela J. Reynolds, et al., "Functional Analysis Of The SH2 And SH3 Domains Of the lck Tyrosine Protein Kinase".

Science, vol. 259, Feb. 19, 1993, Ruibao Ren, et al., "Identification Of A Ten–Amino Acid Proline–Rich SH3 Binding Site", pp. 1157–1161.

Proc. Natl. Acad. Sci, USA, vol. 90, pp. 7366–7370, Aug. 1993, Kanteti V.S. Prasad, et al., "Src–Homology 3 Domain Of Protein Kinase p59fyn Mediates Binding to Phosphatidylinositol 3–Kinase In T Cells".

Oncogene Research, 1968, vol. 3, pp. 343–355, William M. Potts, et al., "Activation Of pp60c–src Transforming Potential By Mutations Altering The Structure Of An Amino Terminal Domain Containing Residues 90–95".

Molecular and Cellular Biology, Sep. 1993, pp. 5877–5887, vol. 13, No. 9, Christopher M. Pleiman, et al., "Mapping Of Sites On The Src Family Protein Tyrosine Kinases p55blk, p59fyn, And p56lyn Which Interact With The Effector Molecules Phospholipase C–y2, Microtubule–Associated Protein Kinase, GTPase–Activating Protein, And Phosphatidylinositol 3–Kinase".

Phil. Trans. R. Soc. Land. B, 1993, vol. 340, pp. 279–285, Tony Pawson, et al., "Proteins With SH2 And SH3 Domains Couple Receptor Tyrosine Kinases to Intracellular Signalling Pathways".

Cell, vol. 71, pp. 359–362, Oct. 30, 1992, Tony Pawson, et al., "SH2 And SH3 Domains: From Structure To Function".

Current Biology, 1993, vol. 3, No. 7, T. Pawson, et al., "SH2 and SH3 Domains", pp. 434–442.

Cell, vol. 73, pp. 179–191, Apr. 9, 1993, Jean Paul Olivier, et al., "A Drosophila SH2–SH3 Adaptor Protein Implicated In Coupling The Sevenless Tyrosine Kinase To An Activator Of Ras Guanine Nucleotide Exchange, SOS".

Proc. Natl. Acad. Sci. USA, vol. 89, pp. 5393–5397, Jun. 1992, Kevin R. Oldenburg, et al., "Peptide Ligands For A Sugar–Binding Protein Isolated From a Random Peptide Library".

The Journal of Biological Chemistry, vol. 268, No. 24, Aug. 25, 1993, pp. 18070–18075, Masato Okada, et al., "Deletion Of The SH3 Domain Of Src Interferes With Regulation By The Phosphorylated Carboxyl–Terminal Tyrosine".

The EMBO Journal, vol. 12, No. 7, pp. 2617–2624, 1993, Martin E.M. Noble, et al., "Crystal Structure Of The SH3 Domain In Human Fyn; Comparison Of The Three–Dimensional Structures of SH3 Domains In Tyrosine Kinases And Spectrin".

Nature, vol. 359, Oct. 29, 1992, Andrea Musacchio, et al., "Crystal Structure Of A Src–Homology 3 (SH3) Domain", pp. 851–855.

FEBS Letters, vol. 307, No. 1, pp. 55–61, Jul. 1992, Andrea Musacchio, et al., "SH3—An Abundant Protein Domain In Search Of A Function".

Molecular and Cellular Biology, Sep. 1993, pp. 5290–5300, vol. 13, No. 9, Steven M. Murphy, et al., "Suppression Of c–Src Activity By C–Terminal Src Kinase Involves The c–Src SH2 And SH3 Domains: Analysis With *Saccharomyces cerevisiae*".

Journal of Cell Science, vol. 105, pp. 647–654, 1993, J. Merilainen, et al., Binding of theα–Fodrin SH3 Domain To The Leading Lamellae Of Locomoting Chicken Fibroblasts.

Molecular and Cellular Biology, Aug. 1992, pp. 3425–3430, vol. 12, No. 8, Rene H. Medena, et al., "GTPase–Activating Protein SH2–SH3 Domains Induce Gene Expression In A Ras–Dependent Fashion".

The EMBO Journal, vol. 12, No. 8, pp. 3073–3081, 1993, Jane McGlade, et al., "The N–Terminal Region Of Gap Regulates Cytoskeletal Structure And Cell Adhesion".

Science, vol. 255, George A. Martin, et al., "Gap Domains Responsible For Ras p21–Dependent Inhibition Of Muscarinic Atrial K+ Channel Currents", pp. 192–194.

Cell, vol. 70, pp. 431–442, Aug. 7, 1992, E.J. Lowenstein, et al., "The SH2 and SH3 Domain–Containing Protein GRB2 Links Receptor Tyrosine Kinases To ras Singaling".

Journal of Immunological Methods, vol. 152, 1992, pp. 149–157, Johannes A. Lenstra, et al., "Isolation Of Sequences From A Random–Sequence Expression Library That Mimic Viral Epitopes".

Molecular and Cellular Biology, Sep. 1993, pp. 5225–5232, vol. 13, No. 9, Xingquan Liu, et al., "The v–Src SH3 Domain Binds Prosphatidylinositol 3'–Kinase".

Nature, vol. 354, Nov. 7, 1991, pp. 82–84, Kit S. Lam, et al., "A New Type Of Synthetic Peptide Library For Identification Ligand–Binding Activity".

Cell, vol. 72, pp. 945–952, Mar. 26, 1993, Satoshi Koyama, et al., "Structure Of The P13K SH3 Domain And Analysis Of The SH3 Family".

Cell, vol. 72, pp. 953–960, Mar. 26, 1993, D. Kohda, et al., "Solution Structure Of The SH3 Domain Of Phospholipase C–γ".

Science, vol. 252, May 3, 1991, C. Anne Koch, et al., "SH2 And SH3 Domains: Elements That Control Interactions Of Cytoplasmic Signaling Proteins", pp. 668–674.

Gene, vol. 128, 1993, pp. 59–65, Brian K. Kay, et al., "An M13 Phage Library Displaying Random 38–Amino–Acid Peptides As A Source Of Novel Sequences With Affinity To Selected Targets".

Methods in Cell Biology, vol. 36, Brian K. Kay, "Injection Of Oocytes And Embryos", pp. 663–669.

Oncogene, 1993, vol. 8, pp. 1943–1956, Peter K. Jackson, et al., "Mutation Of A Phenylalanine Conserved In SH3–Containing Tyrosine Kinases Activates The Transforming Ability Of c–Abl".

BioFeature, vol. 13, No. 3, 1992, pp. 412–421, R.A. Houghten, et al., "The Use Of Synthetic Peptide Combinatorial Libraries For The Identification Of Bioactive Peptides".

Nature, vol. 354, Nov. 7, 1991, Richard A. Houghton, et al., "Generation And Use Of Synthetic Peptide Combinatorial Libraries For Basic Research And Drug Discover", pp. 84–86.

The Journal of Cell Biology, vol. 122, No. 3, Aug. 1993, pp. 635–644, Douglas A. Holtzman, et al., Synthetic–Lethal Interactions Identify Two Novel Genes, SLA1 and SLA2, That Control Membrane Cytoskeleton Assembly In *Saccharomyces cerevisiae*.

Cell, vol. 75, pp. 25–36, Oct. 8, 1993, Ivan Gout, et al., "The Gtpase Dynamin Binds To And Is Activated By A Subset Of SH3 Domains".

Nature, vol. 363, May 6, 1993, pp. 88–92, Nicholas W. Gale, et al., "GRB2 Mediated The EGF–Dependent Activation Of Guanine Nucleotide Exchange On Ras".

Research Report, vol. 13, No. 3, 1992, Dana M. Fowlkes, et al., "Multipurpose Vectors For Peptide Expression On The M13 Viral Surface", 6 pages.

Science, vol. 251, Feb. 15, 1991, Stephen P.A. Fodor, et al., "Light–Directed, Spatially Addressable Parallel Chemical Synthesis", pp. 767–773.

Peptide Research, Gregg B. Fields, vol. 6, No. 3, 1993, "Synthetic Peptides And Tumor Cell Metastasis", pp. 115–120.

J. Mol. Biol., 1991, vol. 222, pp. 301–310, Franco Felici, et al., "Selection Of Antibody Ligands From A Large Library Of Oligopeptides Expressed On A Multivalent Exposition Vector".

Nature, vol. 363, May 6, 1993, Sean E. Egan, et al., pp. 45–51, "Association Of SOS RAS Exchange Protein With GRB2 Is Implicated In Tyrosine Kinase Signal Transduction And Transformation".

Science, vol. 259, Jan. 22, 1993, Marc Duchesne, et al., "Identification Of The SK3 Domain of Gap As An Essential Sequence For RAS–GAP–Mediated Signaling", pp. 525–528.

Virology, vol. 189, pp. 556–567, 1992, Philippe Dezelee, et al., "Small Deletion In V–SRC SH3 Domain Of A Transformation Defective Mutant Of Rous Sarcoma Virus Restores Wild Type Transforming Properties".

Science, vol. 249, James J. Devlin, et al., "Random Peptide Libraries: A Source Of Specific Protein Binding Molecules", pp. 404–406.

Proc. Natl. Acad. Sci. USA, vol. 87, Aug. 1990, pp. 6378–6382, Steven E. Cwirla, et al., "Peptides On Phage: A Vast Library Of Peptides For Identifying Ligands".

Nature, vol. 356, Mar. 26, 1992, Scott G. Clark, et al., "*C. elegans* cell–Signalling Gene Sem–5 Encodes A Protein With SH2 And SH3 Domains", pp. 340–343.

Science, vol. 257, Aug. 7, 1992, Piera Ciccnetti, et al., "Identification Of A Protein That Binds To The SH3 Region Of Abl And Is Similar to BCR And GAP–RHO", pp. 803–806.

Nature, vol. 356, Mar. 5, 1992, Janet Chemevert, et al., "A Yeast Gene (BEM1) Necessary For Cell Polarization Whose Product Contains Two SH3 Domains", pp. 77–79.

J. Am. Chem. Soc., 1993, vol. 115, pp. 12591–12592, James K. Chen, et al., "Biased Combinatorial Libraries: Novel Ligands For The SH3 Domain Of Phosphatidylinositol 3–Kinase".

Science, vol. 260, May 28, 1993, pp. 1338–1343, "Human SOS1: A Guanine Nucleotide Exchange Factor For RAS That Binds To GRB2", Pierre Chardin, et al.

Cell, vol. 73, pp. 813–822, May 21, 1993, Grant W. Booker, et al., "Solution Struture And Ligand–Binding Site Of The SH3 Domain Of The p85α Subunit Of Phosphatidylinositol 3–Kinase".

Molecular and Cellular Biology, Aug. 1993, pp. 5070–5084, vol. 13, No. 8, Florian Bauer, et al., "Alteration Of A Yeast SH3 Protein Leads To Conditional Viability With Defects In Cytoskeletal And Budding Patterns".

Cell, vol. 74, pp. 83–91, Jul. 16, 1993, D. Bar–Sagi, et al., "SH3 Domains Direct Cellular Localization Of Signaling Molecules".

Current Opinion in Structural Biology, 1993, vol. 3, pp. 572–579, Ronald N. Noess, "Phage Display Of Peptides And Protein Domains".

The Journal of Biological Chemistry, vol. 269, No. 39, Sep. 1994, Christopher Cheadle, et al., "Identification Of A SRC SH3 Domain Binding Motif By Screening A Random Phage Display Library", pp. 24034–24039.

Proc. Natl. Acad. Sci. USA, vol. 89, pp. 5398–5402, Jun. 1992, Jamie K. Scott, et al., "A Family Of Concanavalin A–Binding Peptides From A Hexapeptide Epitope Library".

Sparks et al., 1996, "Cloning of ligand targets: systematic isolation of SH3 domain–containing proteins," Nature Biotechnology 14:741–744.

Rickles et al., 1994, "Identification of Src, Fyn, Lyn, P13K and Abl SH3 domain ligands using phage display libraries," EMBO J. 12:5598–5604.

FIG. 5

| CLONE | SEQUENCE | | | FREQUENCY |
|---|---|---|---|---|
| T9.SRC3.2 | | RELPPLP | PSRASFGGGASRPSR | 2 |
| T12.SRC3.4 | | RPLPIPP | ETRPSR | 1 |
| T12.SRC3.6 | | RPLPIPP | VTRPSR | 1 |
| T9.SRC3.4 | SSSFDQQDWDYSIAEKMHPIRPGF | SPLPPLP | THLQSSRPSR | 1 |
| T9.SRC3.6 | STNVVTGSVIARGAQS | GPLPPLP | NDSRPSR | 2 |
| T12.SRC3.7 | STAPWGLRVAHEGGVLK | RPVPPIT | RPSRT | 1 |
| T12.SRC3.5 | SSSGYVVPKRLGDMREYNAHPGLHVPPN | RLPPLPT | RPSRT | 1 |
| T9.SRC3.7 | SSSRGEGNNIISSRPFLSNSDPGVSNKLTGR | RALPSPP | SASRPSR | 1 |
| T12.SRC3.3 | STAVSFRFMPGGGGAFYST | RRLPPTP | ATRPSR | 4 |
| T9.SRC3.5 | STAHSLVDWGTFSGVSHKS | RQLPPTP | GRDPSHSRPSR | 1 |
| T9.SRC3.1 | PGYARIVSYRF | RRLPRTP | PPASRPSR | 5 |
| T12.SRC3.2 | STNDVDWHMNSGGPH | RPLPTRP | SRTVESC | 19 |
| T9.SRC3.3 | SSDNWARRVHASELIYTDLSPGILLAQ | RPLPSRP | SRTVESC | 2 |
| T9.SRC3.8 | SSESPLMYNRVGALQSLTSVPGSMMHFALQ | RILLLPS | EPRTFYNYGHDSRPSR | 1 |
| T12.SRC3.1 | STRWSHSWPGYVGGANPSPAT SRYNDLGTRPVSEVIKYDYFPGYSQHVITPDGSYST PG | PPVPPRN | TRPSR | 25 |
| Consensus | STMYGVSWLSSGSGGILA | RPLPPLP | | |

| | | | | |
|---|---|---|---|---|
| R8C.YES3.6 | SSCTEKTVSGWCGSRST | RPLPILP | RTTRPSR | 1 |
| R8C.YES3.5 | SSCMLPTDGVQCGSRSTP | RPLPMLP | TTRPSR | 1 |
| R8C.YES3.3/SRC3.1 | SSCDGTQFRLNCGSRSTN | RPLPMIP | TTRPSR | 3 |
| R8C.YES3.1/SRC3.2 | SSCMQGQAGLKCGSRSI | RPLPSLP | ITTRPSR | 7 |
| R8C.YES3.7 | SSCYREKDTWGCGSRSTS | RPLPSLP | TTRPSR | 2 |
| R8C.YES3.2 | SSCLFEQGAGTCGSRST | RSLPPLP | PTTRPSR | 2 |
| R8C.YES3.4 | SSCDHTLGLGWCGSRSI | RQLPIPP | TITRPSR | 1 |
| R8C.YES3.10 | SSCDTGRIAPGCGSRSTP | RPLPLIP | TTPRSTNLNLTSTTTRPSR | 2 |
| R8C.YES3.8 | SSCGLDNAAKTCGSRST | RPLPPTP | LTTRPSR | 2 |
| R8C.YES3.9 | SSCSRAHETEMCGSRST | RPQPPPP | ITTRPSR | 2 |
| Consensus | | RPLPPLP | | |

SRC SH3 BINDING PEPTIDES AND METHODS OF ISOLATING AND USING SAME

This is a continuation of application Ser. No. 08/278,865 filed Jul. 22, 1994, now U.S. Pat. No. 6,303,574.

1. FIELD OF THE INVENTION

The present invention relates to SH3 binding peptides having a broad range of binding specificities. That is, certain members of the SH3 binding peptides disclosed bind with approximately the same facility with SH3 domains derived from different SH3 domain-containing proteins. Other members, in contrast, bind with a much greater degree of affinity for specific SH3 domains. The SH3 binding peptides are obtained from random peptide libraries that are also phage-displayed. Methods are described of obtaining the phage clones that bind to the SH3 domain targets and of determining their relevant nucleotide sequences and consequent primary amino acid sequence of the binding peptides. The resulting SH3 binding proteins are useful in a number of ways, including, but not limited to, providing a method of modulating signal transduction pathways at the cellular level, of modulating oncogenic protein activity or of providing lead compounds for development of drugs with the ability to modulate broad classes, as well as specific classes, of proteins involved in signal transduction.

2. BACKGROUND OF THE INVENTION

2.1. Src and the SH3 Domain

Among a number of proteins involved in eukaryotic cell signaling, there is a common sequence motif called the SH3 domain. It is 50–70 amino acids in length, moderately conserved in primary structure, and can be present from one to several times in a large number of proteins involved in signal transduction and in cytoskeletal proteins.

The protein pp60c-src represents a family of at least nine non-receptor protein tyrosine kinases (NR-PTKs). Members of this family share an overall structural organization comprising a series of catalytic and non-catalytic domains. In Src, a 14-amino-acid myristylation signal resides at the extreme amino-terminus, and is followed by a unique region that is not highly conserved among family members. Following this region are two highly conserved 60- and 100-amino-acid regions, the Src homology (SH) domains 3 and 2, respectively. SH2 and SH3 domains have been shown to play an important role in mediating protein—protein interactions in a variety of signaling pathways. Koch, C. A., et al., in *Science* (1991) 252:668–74. The carboxy-terminal half of Src contains the PTK catalytic domain, as well as a negative regulatory tyrosine (Y527) near the carboxy terminus. Phosphorylation of this residue (e.g., by Csk) results in the inhibition of PTK activity. Cooper, J. A., et al., in *Science* (1986) 231:1431–1434. Mutation of Y527→F generates forms of Src with increased PTK and oncogenic activity. Cartwright, C. A., et al., in *Cell* (1987) 49:83–91; Kmiecik, T. E., et al., in *Cell* (1987) 49:65–73; and Piwicna-Worms, H., et al., in *Cell* (1987) 75–82.

The fact that some mutations which result in increased Src PTK and transforming activity map to the Src SH2 (Seidel-Dugan, C., et al., in *Mol. Cell. Biol.* (1992) 12:1835–45; and Hirai, H. and Varmus, H. E. in *Mol. Cell. Biol.* (1990) 10:1307–1318) and SH3 domains (Seidel-Dugan, C., et al., supra; Hirai, H. and Varmus, H. E., supra; Superti-Furga, G., et al., in *Embo. J.* (1993) 12:2625–34; and Potts, W. M., et al., in *Oncogene Res.* (1988) 3:343–355) suggests a negative regulatory role for these domains. That phosphotyrosine residues within specific sequence contexts represent high affinity ligands for SH2 domains suggests a model in which the SH2 domain participates in Y527-mediated inhibition of PTK activity by binding phosphorylated Y527, thereby locking the kinase domain in an inactive configuration. Matsuda, M., Mayer, B. J., et al., in *Science* (1990) 248:1537–1539. This model is supported by the observation that phosphopeptides corresponding to the carboxy-terminal tail of Src bind active, but not inactive, variants of Src. Roussel, R. R., et al., in *Proc. Natl. Acad. Sci. USA* (1991) 88:10696–700; and Liu, X., et al., in *Oncogene* (1993) 8:1119–1126.

The mechanism of SH3-mediated inhibition of Src PTK activity remains unclear. There is evidence that pY527-mediated inhibition of Src PTK activity involves the SH3 domain as well as the SH2 domain. Okada, M., Howell, et al., in *J. Biol. Chem.* (1993) 268:18070–5; Murphy, S. M., et al., in *Mol. Cell. Biol.* (1993) 13:5290–300; and Superti-Furga, G., et al., supra. Although these effects are thought to be a consequence of SH3-mediated protein—protein interactions, precisely how the Src SH3 domain exerts its negative regulatory effect is unclear. Identification of high affinity ligands for the Src SH3 domain could help resolve these issues.

2.2. Protein Tyrosine Kinases and the Immune Response

Src-related tyrosine kinases are expressed in a variety of cell types including those of the immune system (lymphocytes, T cells, B cells, and natural killer cells) and the central nervous system (neural cells, neurons, oligodendrocytes, parts of the cerebellum, and the like). Umemori, H. et al., in *Brain Res. Mol. Brain Res.* (1992) Dec. 16(3–4):303–310. Their presence in these cells and tissues and their interaction with specific cell surface receptors and immunomodulatory proteins (such as T cell antigen receptor, CD14, CD2, CD4, CD40 or CD45) suggest that these kinases serve an important role in the signalling pathways of not only the central nervous system but of the immune system, as well. See, e.g., Ren, C. L. et al., in *J. Exp. Med.* (1994) 179(2):673–680 (signal transduction via CD40 involves activation of Lyn kinase); Donovan, J. A. and Koretzky, G. A., in *J. Am. Soc. Nephrol.* (1993) 4(4):976–985 (CD45, the immune response, and regulation of Lck and Fyn kinases); and Carmo, A. M. et al., in *Eur. J. Immunol.* (1993) 23(9):2196–2201 (physical association of the cytoplasmic domain of CD2 with p56lck and p59fyn).

For instance, mice with disruptions in their Src-like genes, Hck and Fgr, possess macrophages with impaired phagocytic activity or exhibit a novel immunodeficiency characterized by an increased susceptibility to infection with Listeria monocytogenes. Lowell, C. A. et al., in *Genes Dev.* (1994) 8(4):387–398. Also, it has been shown that bacterial lipopolysaccharide (LPS) activates CD14-associated p56lyn, p68hck, and p59c-fgr, while inducing the production of lymphokines, such as TNF-alpha, IL-1, IL-6, and IL-8. Inhibition of the protein tyrosine kinases blocks production of TNF-alpha and IL-1.

2.3. SH3 Binding Peptides

As mentioned above, it has long been suspected that SH3 domains are sites of protein—protein interaction, but it has been unclear what SH3 domains actually bind. Efforts to identify ligands for SH3 domains have led to the characterization of a number of SH3-binding proteins, including 3BP1 and 2 (Ren, R., Mayer, et al., in *Science* (1993) 259:1157–61), SOS (Olivier, J. P., et al., in *Cell* (1993) 73:179–91; and Rozakis-Adcock, M., et al., in *Nature*

(1993) 363:83–5), p85 PI-3' Kinase (Xingquan, L., et al., in *Mol. Cell. Biol.* (1993) 13:5225–5232), dynamin (Gout, I., et al., in *Cell* (1993) 75:25–36), AFAP-110 (Flynn, D. C., et al., in *Mol. Cell. Biol.* (1993) 13:7892–7900), and CD42 (Barfod, E. T., et al., in *J. Biol. Chem.* (1993) 268:26059–26062). These proteins tend to possess short, proline-rich stretches of amino acids, some of which have been directly implicated in SH3 binding. A variety of consensus sequences have been proposed, although the similarity among proline-rich regions of different SH3-binding proteins tends to be fairly low. Also, attempts to build consensus sequences are likely complicated by the incorporation of data from proteins that bind different SH3 domains.

Thus, Cicchetti, P., et al., in *Science* (1992) 257:803–806, published their work relating to the isolation and sequencing of two naturally-occurring proteins that could be bound in vitro by the SH3 domain of the abl oncogene product. These workers found that SH3 domains bind short, proline-rich regions of such proteins. Subsequently, this same group disclosed further results (Ren, R. et al., supra) in which the SH3 binding sites of the SH3 binding proteins were localized to "a nine- or ten-amino acid stretch rich in proline residues." A consensus sequence incorporating the features of the SH3 binding sites of four SH3 binding proteins was proposed: XPXXPPPΨXP (SEQ ID NO:1), wherein X indicates a position in the amino acid sequence which is not conserved among the four SH3 binding proteins, P represents proline, and Ψ indicates a hydrophobic amino acid residue, such as P or L.

The screening of complex random peptide libraries has been used to identify peptide epitopes for monoclonal (Scott, J. K. and Smith, G. P. in *Science* (1990) 249:386–390) and polyclonal (Kay, B. K., et al., in *Gene* (1993) 128:59–65) antibodies, as well as peptide ligands for a variety of proteins, including streptavidin (Devlin, J. J., et al., in *Science* (1990) 249:404–406; and Lam, K., et al., in *Nature* (1991) 354:82–84), the endoplasmic reticulum chaperone BiP (Blond-Elguindi, S., et al., in *Cell* (1993) 75:717–728), and CaM (Dedman, J. R., et al., in *J. Biol. Chem.* (1993) 268:23025–23030).

Recently, Chen, J. K. et al., in *J. Am. Chem. Soc.* (1993) 115:12591–12592, described ligands for the SH3 domain of phosphatidylinositol 3-kinase (PI-3' Kinase) which were isolated from a biased combinatorial library. A "biased" library is to be distinguished from a "random" library in that the amino acid residue at certain positions of the synthetic peptide are fixed, i.e., not allowed to vary in a random fashion. Indeed, as stated by these research workers, screening of a "random" combinatorial library failed to yield suitable ligands for a PI-3' Kinase SH3 domain probe. The binding affinities of these unsuitable ligands was described as weak, >100 μM, based on dissociation constants measured by the Biosensor System (BIAcore).

More recently, Yu, et al. (Yu, H., et al., in *Cell* (1994) 76:933–945) used a "biased" synthetic peptide library of the form XXXPPXPXX (SEQ ID NO:2), wherein X represents any amino acid other than cysteine, to identify a series of peptides which bind the Src and PI-3' Kinase SH3 domains. The bias was accomplished by fixing the proline residues at the specific amino acid positions indicated for the "random" peptide. As stated previously, without this bias, the technique disclosed fails to identify any SH3 domain-binding peptides.

A consensus sequence, based on 13 binding peptides was suggested: RXLPPRPXX (SEQ ID NO:3), where X tends to be a basic residue (like R, K or H). The binding affinities of several SH3 binding peptides were disclosed as ranging from 8.7 to 30 μM. A "composite" peptide, RKLPPRPRR (SEQ ID NO:4), was reported to have a binding affinity of 7.6 μM. This value compares favorably to the binding affinity of the peptide, VPPPVPPRRR (SEQ ID NO:5), to the N-terminal SH3 domain of Grb2. See, Kraulis, P. J. *J. Appl. Crystallogr.* (1991) 24:946. Recognizing the limitations of their technique, Chen and co-workers, supra, stated that their results "illustrate the utility of biased combinatorial libraries for ligand discovery in systems where there is some general knowledge of the ligand-binding characteristics of the receptor" (emphasis added).

Yu and co-workers, supra, further described an SH3 binding site consensus sequence, XpØPpXP (SEQ ID NO:6), wherein X represents non-conserved residues, Ø represents hydrophobic residues, P is proline, and p represents residues that tend to be proline. A consensus motif of RXLPPRPXX (SEQ ID NO:7), where X represents any amino acid other than cysteine, was proposed for ligands of PI-3' Kinase SH3 domain. A consensus motif of RXLPPL-PRø (SEQ ID NO:8), where ø represents hydrophobic residues, was proposed for ligands of Src SH3 domain. Still, the dissociation constants reported for the 9-mer peptides ranged only from about 8–70 μM and selectivity between one type of SH3 domain and another was relatively poor, the $K_D$s differing by only about a factor of four.

Hence, there remains a need to develop techniques for the identification of Src SH3 binding peptides which do not rely on such "biased" combinatorial peptide libraries that are limited to a partially predetermined set of amino acid sequences. Indeed, the isolation of SH3 binding peptides from a "random" peptide library has not been achieved successfully before now. Furthermore, particular peptides having much greater binding affinities, whether general or more selective binding for specific SH3 domains, remain to be identified. Binding peptides specific for particular SH3 domains are useful, for example, in modulating the activity of a particular SH3 domain-containing protein, while leaving others bearing an SH3 domain unaffected. Still, the more promiscuous general binding peptides are useful for the modulation of a broad spectrum of SH3 domain-containing proteins.

The present invention relates to such SH3 binding peptides, methods for their identification, and compositions comprising same. In particular, peptides comprising particular sequences of amino acid residues are disclosed which were isolated from random peptide libraries. In the present invention, clones were isolated from a phage-displayed random peptide library which exhibited strong binding affinities for SH3 domain-containing protein targets. Some of these protein targets, include Abl, Src, Grb2, PLC-δ, PLC-γ, Ras GAP, Nck, and p85 PI-3' Kinase. From the nucleotide sequence of the binding phage, the amino acid sequence of the peptide inserts has been deduced. Synthetic peptides having the desired amino acid sequences are shown to bind the SH3 domain of the target proteins. In particular, synthetic peptides combining a core consensus sequence and additional amino acid residues flanking the core sequence are especially effective at binding to particular target protein SH3 domains. The SH3 binding peptides disclosed herein can be utilized in a number of ways, including the potential modulation of oncogenic protein activity in vivo. These peptides also serve as useful leads in the production of peptidomimetic drugs that modulate a large class of proteins involved in signal transduction pathways and oncogenesis.

3. SUMMARY OF THE INVENTION

Accordingly, three phage-displayed random peptide libraries were screened for isolates that bind to bacterial fusion proteins consisting of the Src homology region 3 (SH3) and glutathione S-transferase (GST). DNA sequencing of the isolates showed that they contained sequences that resemble the consensus motif, RPLPPLP (SEQ ID NO:9), within their 8, 22, or 36 amino acid long random regions. When peptides were synthesized corresponding to the pIII inserts of the SH3-binding phage, they bound to the GST fusions of the SH3 domains of Src and the Src-related proteins, such as Yes, but not of Grb2, Crk, Abl, or PLCγ1. The synthesized peptides bind quite well to the Src SH3 domain and act as potent competitors of natural Src SH3 interactions in cell lysates. For instance, these peptides can compete with radiolabelled proteins from cell lysates in binding to immobilized Src-GST, with an apparent $IC_{50}$ of 1–10 μM. When a peptide, bearing the consensus sequence RPLPPLP (SEQ ID NO:9) was injected into *Xenopus laevis* oocytes, it accelerated the rate of progesterone-induced maturation. These results demonstrate the utility of phage-displayed random peptide libraries in identifying SH3-binding peptide sequences and that such identified peptides exhibit both in vivo and in vitro biological activity.

Thus, it is an object of the present invention to provide peptides having at least nine and up to forty-five amino acid residues, including an amino acid sequence of the formula, R-2-L-P-5-6-P-8-9 (SEQ ID NO:10), positioned anywhere along the peptide, in which each number represents an amino acid residue, such that 2 represents any amino acid residue except cysteine, 5 and 6 each represents a hydrophobic amino acid residue, 8 represents any amino acid residue except cysteine, and 9 represents a hydrophilic amino acid residue except cysteine, each letter being the standard one-letter symbol for the corresponding amino acid, said peptide exhibiting a binding affinity for the SH3 domain of Src, provided that said peptide is not R-P-L-P-P-L-P-T-S (SEQ ID NO:11). In a particular embodiment of the present invention, the peptides also exhibit a binding affinity for the SH3 domain of Src-related proteins, including Yes, Fyn, Lyn, Lck, Hck and Fgr.

The present invention also contemplates SH3 domain-binding peptides that further comprise a C-terminal-flanking amino acid sequence of the formula 10, 10-11, 10-11-12, 10-11-12-13 (SEQ ID NO:12) or 10-11-12-13-14 (SEQ ID NO:13), in which each number represents any amino acid residue except cysteine, such that 10 is bound to 9 by a peptide bond. Furthermore, peptides are also provided which further comprise an N-terminal-flanking amino acid sequence of the formula 1', 2'-1', 3'-2'-1' or 4'-3'-2'-1' (SEQ ID NO:14) in which each number represents any amino acid residue except cysteine, such that 1' is bound to R by a peptide bond.

Thus, in a particular embodiment, a peptide is disclosed having at least thirteen and up to forty-five amino acid residues, including an amino acid sequence of the formula, 3'-2'-1'-R-2-L-P-5-6-P-8-9-10 (SEQ ID NO:15), positioned anywhere along the peptide, in which each number represents an amino acid residue, such that 3', 2', 1', 2, 8, and 10 each represents any amino acid residue except cysteine, 5 and 6 each represents a hydrophobic amino acid residue, and 9 represents a hydrophilic amino acid residue except cysteine, each letter being the standard one-letter symbol for the corresponding amino acid, said peptide exhibiting a binding affinity for the SH3 domain of Src.

The present invention also seeks to provide new consensus sequences or motifs that reflect variations in SH3 domain binding selectivities or specificities. The present invention also contemplates conjugates of the SH3 binding peptides and a second molecule or chemical moiety. This second molecule may be any desired substance whose delivery to the region of the SH3 domain of a particular protein (or cell containing the protein) is sought. Possible target cells include, but are not limited to, neural cells, immune cells (e.g., T cells, B cells, natural killer cells, and the like), osteoclasts, platelets, epidermal cells, and the like, which cells express Src, Src-related proteins, and potentially, other SH3 domain-containing proteins. In this manner, the modulation of the biological activity of proteins bearing an SH3 domain can be accomplished.

Other methods and compositions consistent with the objectives of the present invention are likewise disclosed. In particular, a method is disclosed of modulating the activity of Src or Src-related proteins comprising administering a composition comprising an effective amount of a peptide of the present invention and a carrier, preferably a pharmaceutically acceptable carrier. In a specific embodiment, the contemplated method results in the inhibition of the activity of Src or Src-related proteins. Alternatively, the method is effective to activate Src or Src-related proteins.

In yet another embodiment, a method is disclosed of identifying a peptide having a region that binds to an SH3 domain comprising: (a) providing an immobilized target protein comprising an SH3 domain; (b) incubating the immobilized target protein with an aliquot taken from a random peptide library; (c) washing unbound library peptides from the immobilized target protein; (d) recovering the peptide bound to the immobilized target protein; and (e) determining the primary sequence of the SH3 domain-binding peptide.

Moreover, a method is disclosed of imaging cells, tissues, and organs in which Src or Src-related proteins are expressed, which comprises administering an effective amount of a composition comprising an SH3 domain-binding peptide conjugated to detectable label or an imaging agent.

Other objectives of the present invention will become apparent to one of ordinary skill in the art after consideration of the above disclosure and the following detailed description of the preferred embodiments.

4. BRIEF DESCRIPTION OF THE FIGURES

FIG. 1 illustrates a scheme for the generation of a random 36 amino acid peptide library (TSAR-9; e.g., SEQ ID NO:16). Oligonucleotides were synthesized (SEQ ID NOS:17–18), converted into double-stranded DNA, cleaved with restriction enzymes (SEQ ID NOS:19–20), and cloned into the M13 vector, m663. The random peptide region encoded by the oligonucleotides is shown in the box (SEQ ID NO:16) and is situated at the N-terminus of mature protein III (SEQ ID NO:21).

Figure 2:
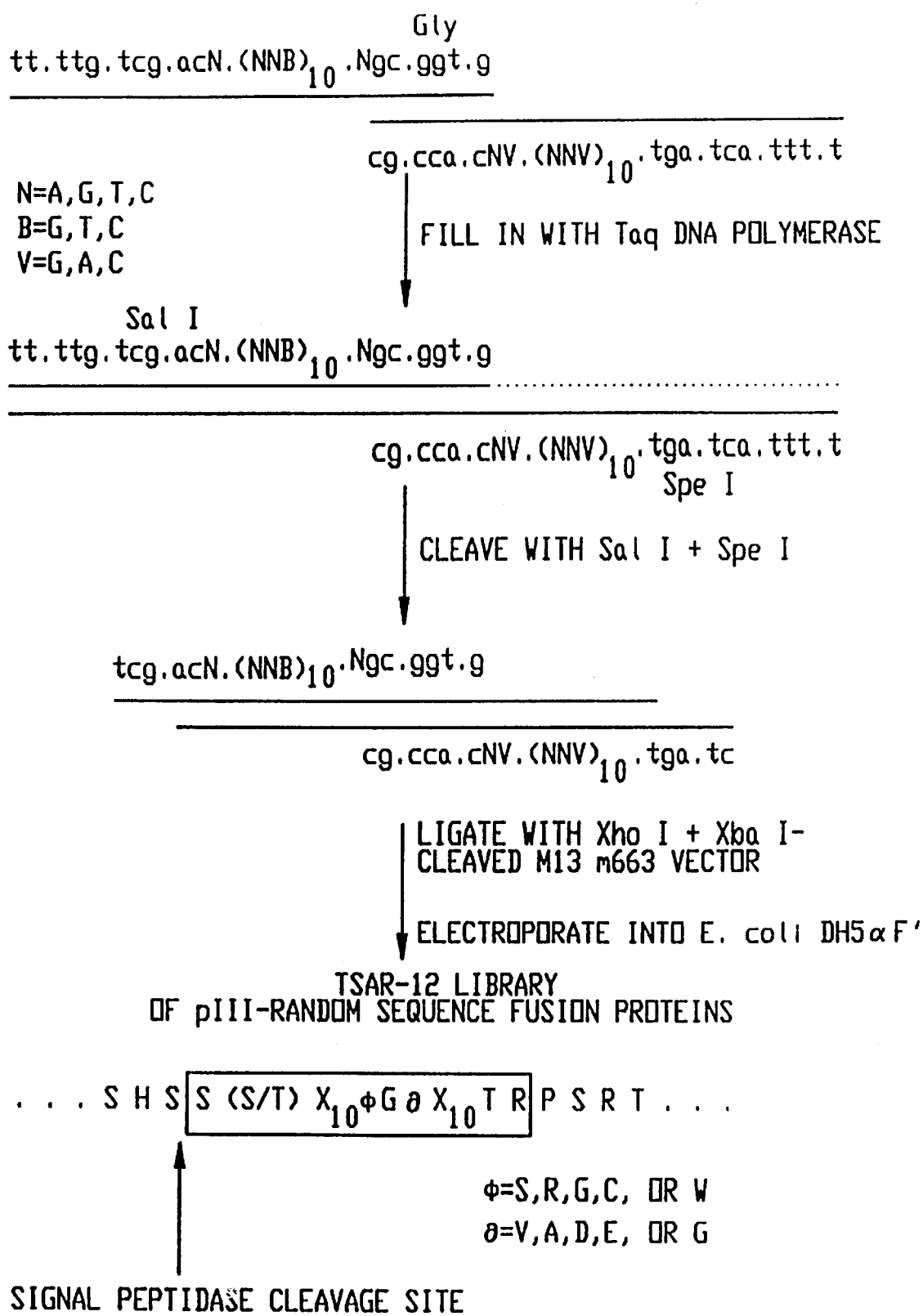

FIG. 2 illustrates a scheme for the generation of a random 22 amino acid peptide library (TSAR-12; e.g., SEQ ID NO:23). Oligonucleotides were synthesized (SEQ ID NOS:24–25), converted into double-stranded DNA, cleaved with restriction enzymes (SEQ ID NOS:26–27), and cloned into the M13 vector, m663. The random peptide region encoded by the oligonucleotides is shown in the box (SEQ ID NO:23) and is situated at the N-terminus of mature protein III (SEQ ID NO:28).

Figure 3:
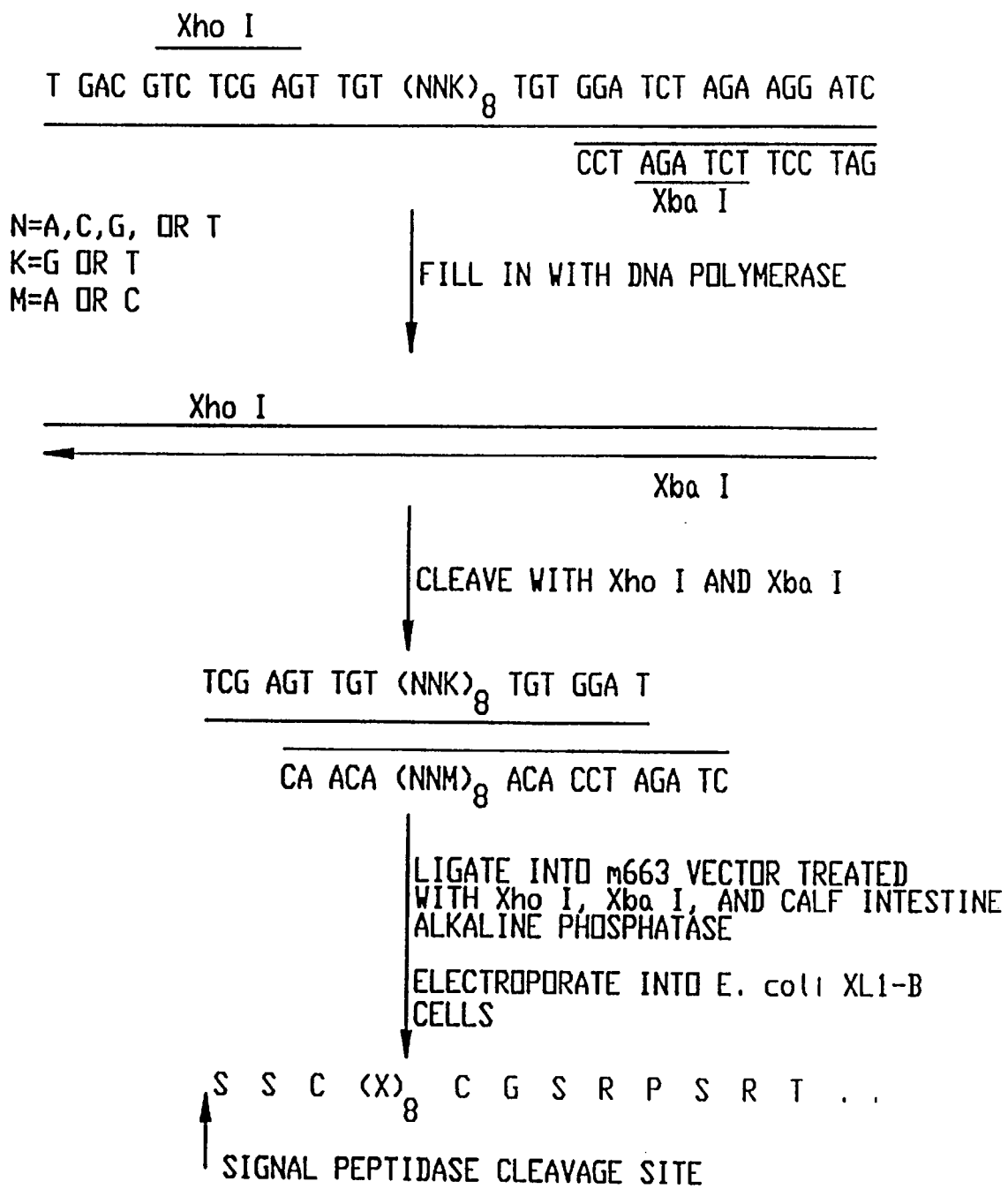

FIG. 3 illustrates a scheme for the generation of a random 8 amino acid peptide library (R8C; SEQ ID NO:30). Oligonucleotides were synthesized (SEQ ID NOS:31–32), converted into double-stranded DNA, cleaved with restriction enzymes (SEQ ID NOS:33–34), and cloned into the M13 vector, m663. The random peptide region (SEQ ID NO:30) is flanked by cysteine residues and is situated at the N-terminus of mature protein III (SEQ ID NO:35).

Figure 4:
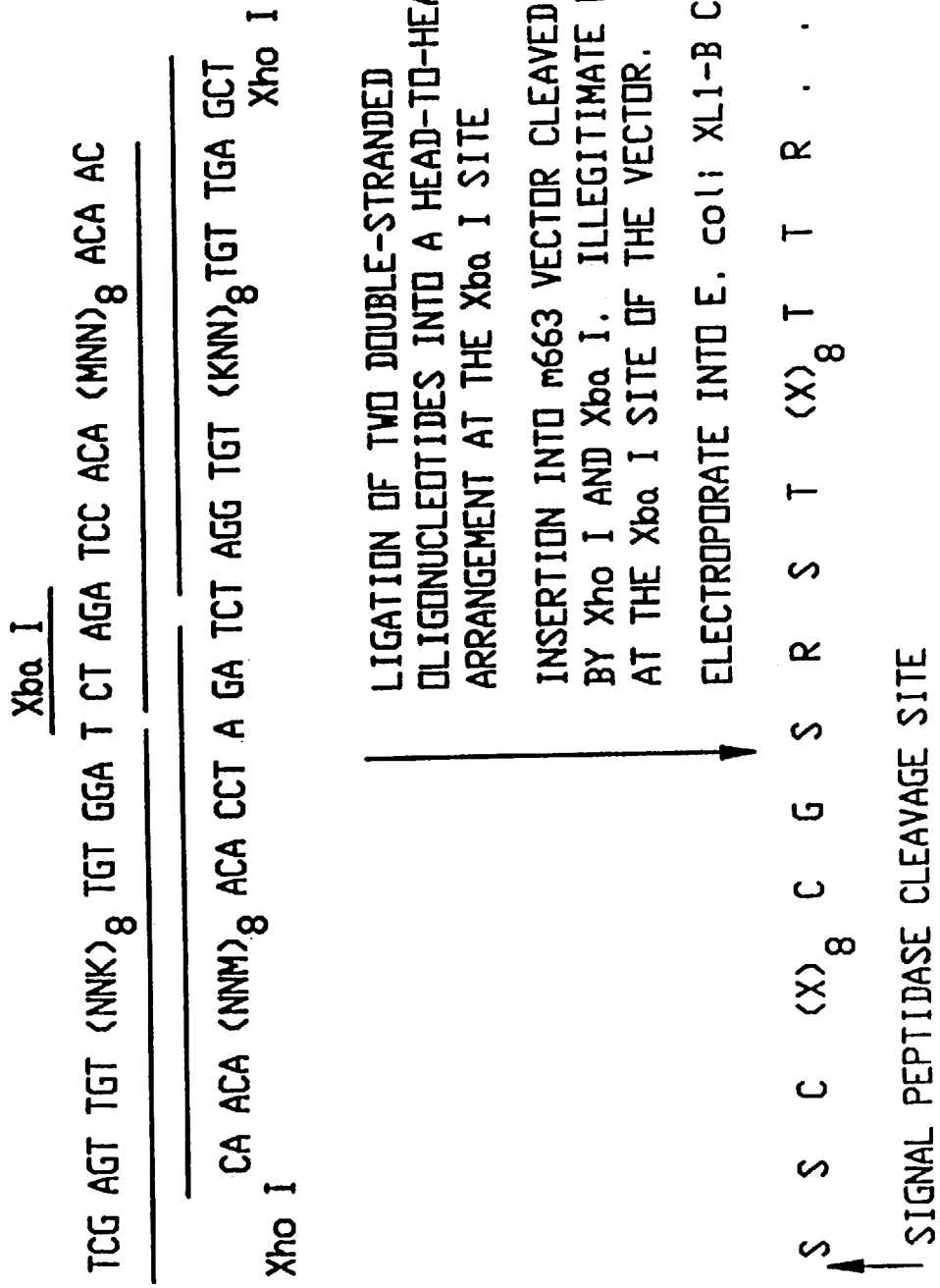

FIG. 4 illustrates the possible origin of one class of double-insert R8C recombinants (e.g., encoding SEQ ID NO:36). Double-stranded oligonucleotides (e.g., SEQ ID NO:37) may have ligated in a head-to-head fashion at the Xba I site prior to cloning in the Xho I-Xba I cleaved M13 vector.

FIG. 5 shows a list of random peptide recombinants (SEQ ID NOS:38–61 and 106) isolated by the method of the present invention and the displayed peptide sequence. The amino acid sequences are aligned to highlight the core sequences. The flanking sequences are shown to the N-terminal and C-terminal ends of the core sequence.

Figure 6:
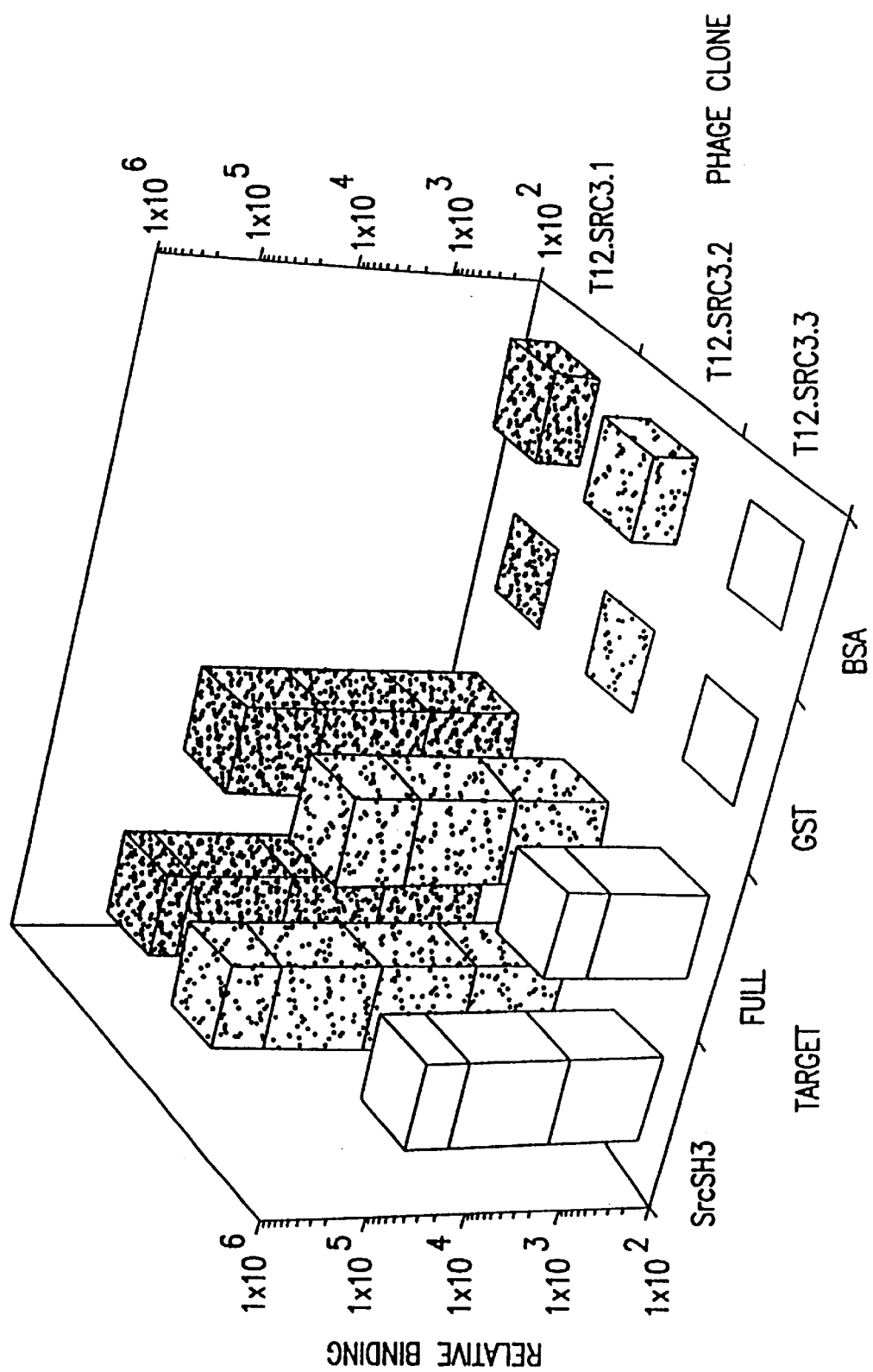

FIG. 6 graphically illustrates the relative binding affinities of selected phage clones for various SH3 domains. The results indicate that certain amino acid sequences provide generic SH3 domain binding, while others can provide greater selectivity for the SH3 domain of Src. Still other clones exhibit Src SH3 domain preferential binding.

Figure 7:
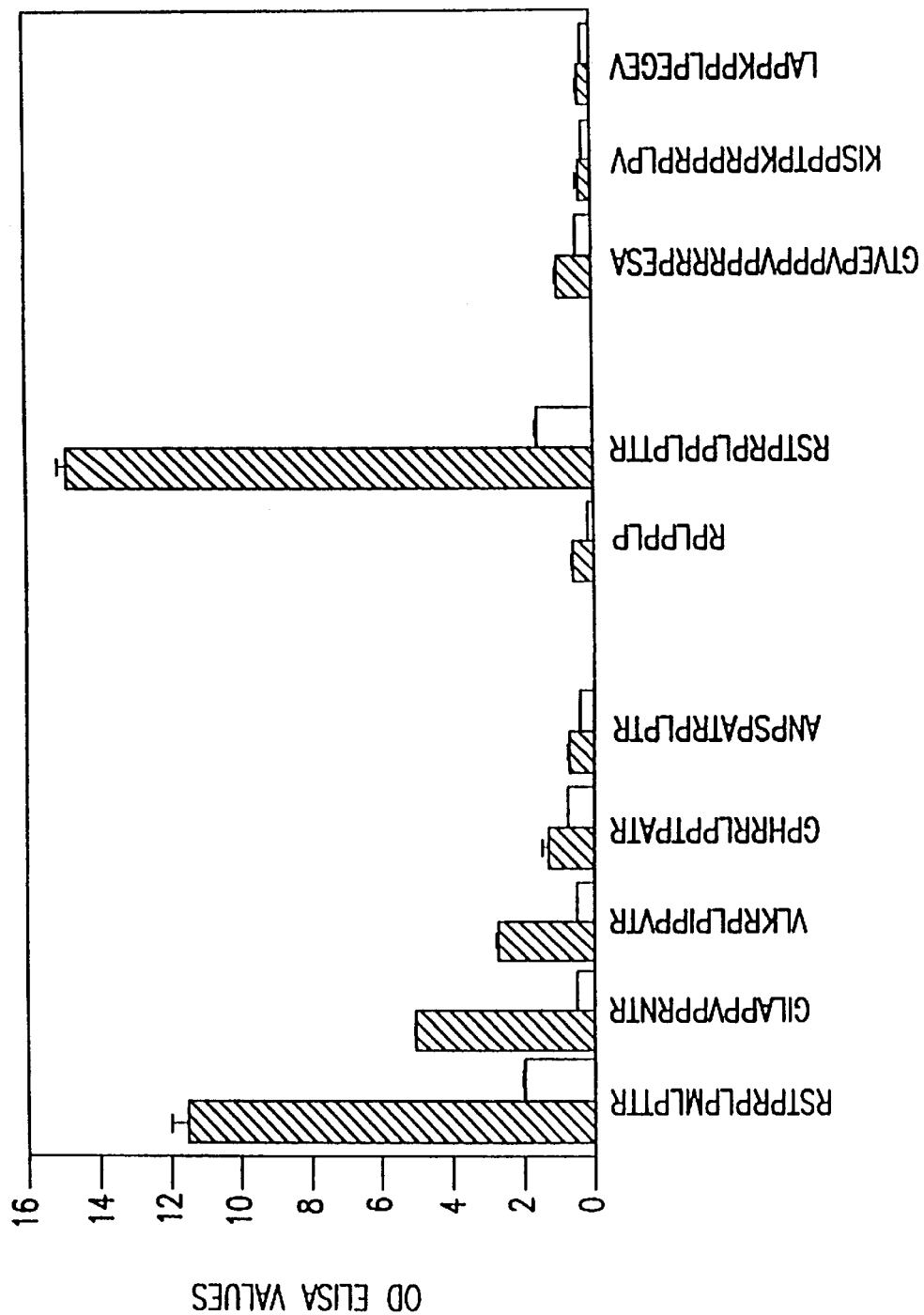

FIG. 7 shows the binding of synthetic peptides (SEQ ID NOS:9 and 62–70) representing Src SH3-selected phage inserts to Src SH3-GST fusion target (shaded columns) over background GST binding (unshaded columns) relative to the core peptide RPLPPLP (SEQ ID NO:9) and proline-rich peptide segments derived from naturally occurring proteins. Bound biotinylated peptide was detected with streptavidin-alkaline phosphatase ELISA. Each point was performed in triplicate; average absorbance at 405 nm is presented. Error bars represent SD.

Figure 8:
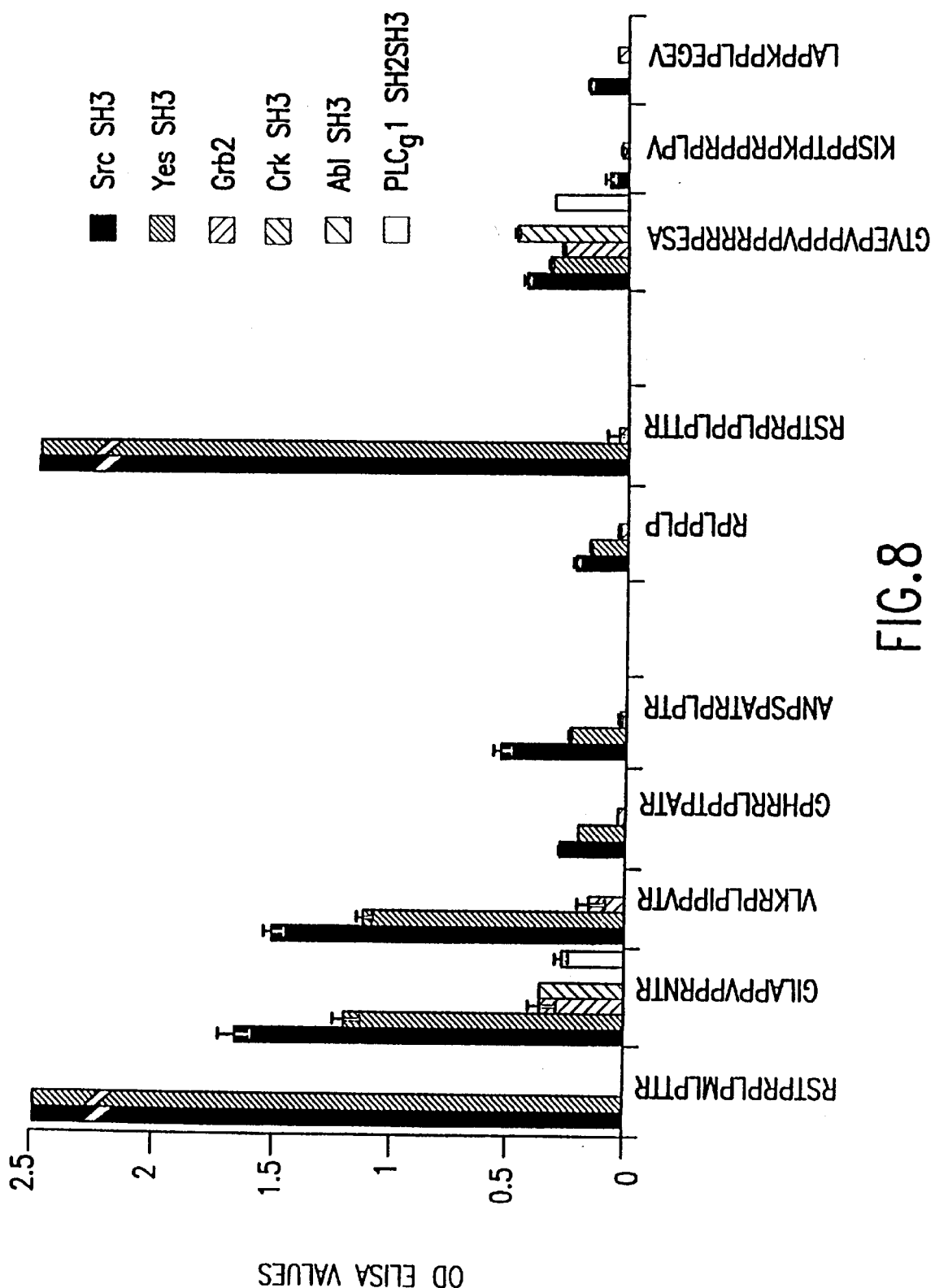

FIG. 8 illustrates the relative specificity of selected peptides (SEQ ID NOS:9 and 62–70) for SH3 domains derived from different proteins. In particular, the binding affinities of the peptides for the SH3 domains of the following protein fusion targets were tested: Src SH3-GST, Yes SH3-GST, Grb2-GST, Crk SH3-GST, Abl SH3-GST, PLCγ1 SH2SH3-GST. Bound biotinylated peptide was detected with streptavidin-alkaline phosphatase. Each point was performed in triplicate; values are average signal (absorbance at 405 nm) above GST background, with error bars representing standard deviation. Hatched bars indicate saturation of the ELISA signal.

Figure 9:
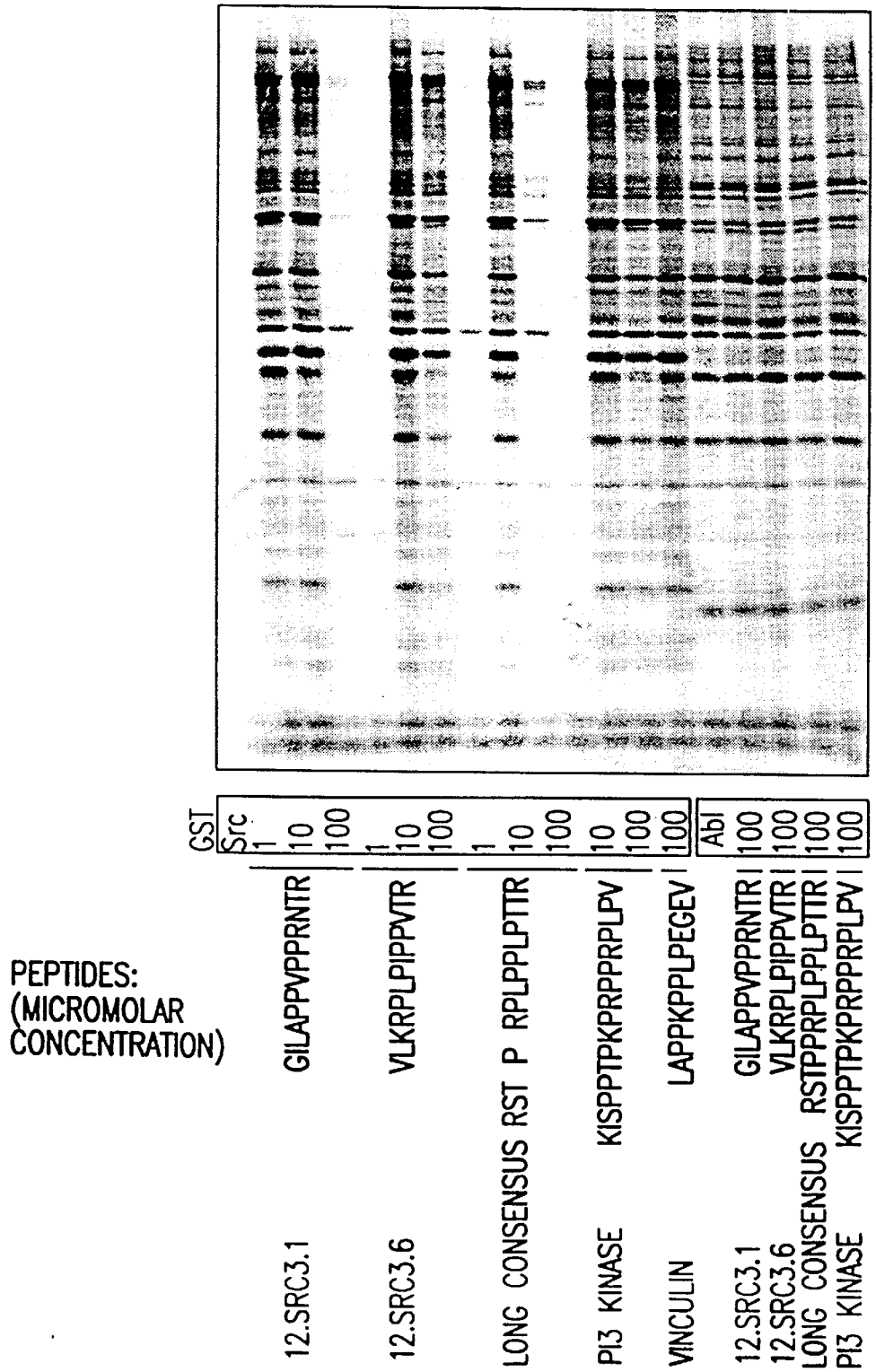

FIG. 9 presents the results of competition experiments in which selected peptides were found to inhibit the binding of proteins from cell lysates to immobilized Src SH3-GST or Abl SH3-GST protein fusion targets.

Figure 10:
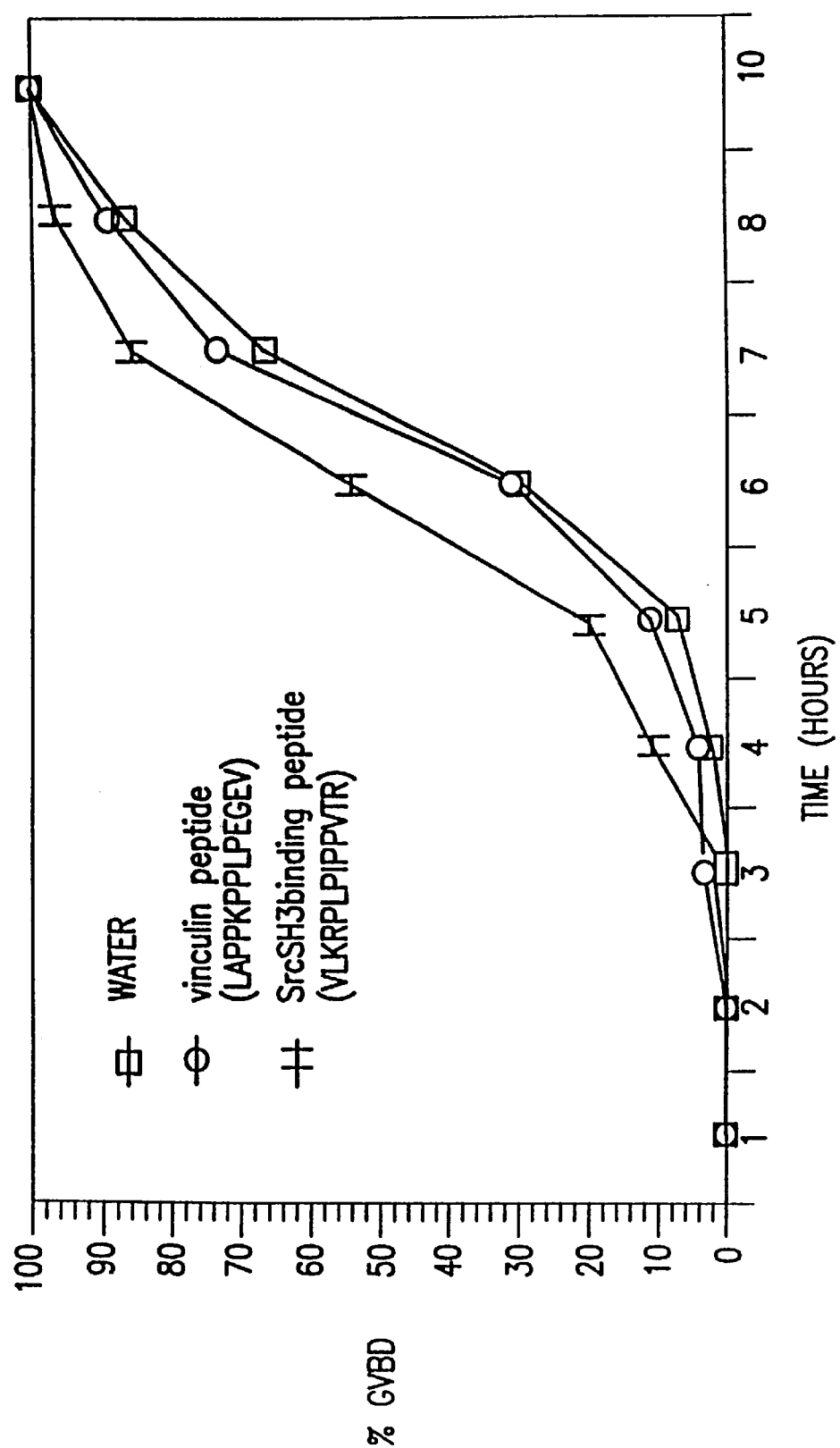
Figure 11A:
Figure 11B:
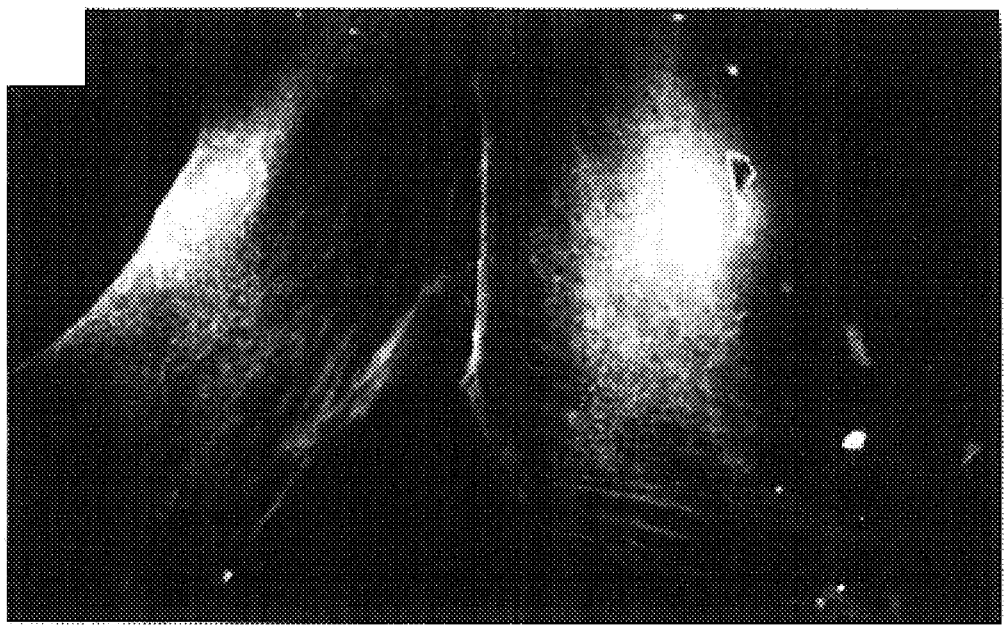
Figure 11C:
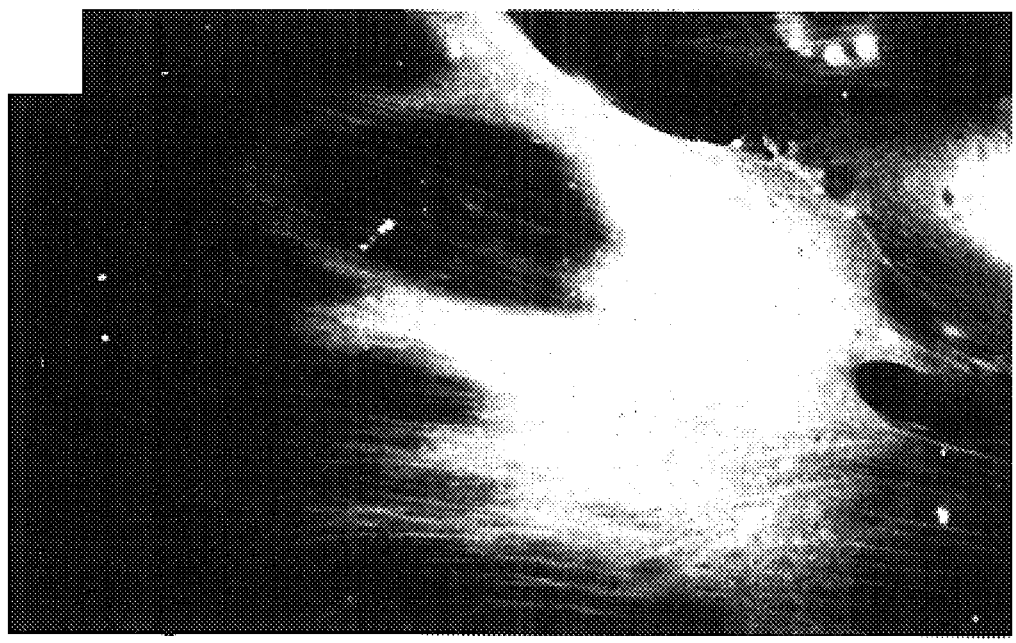
Figure 11D:
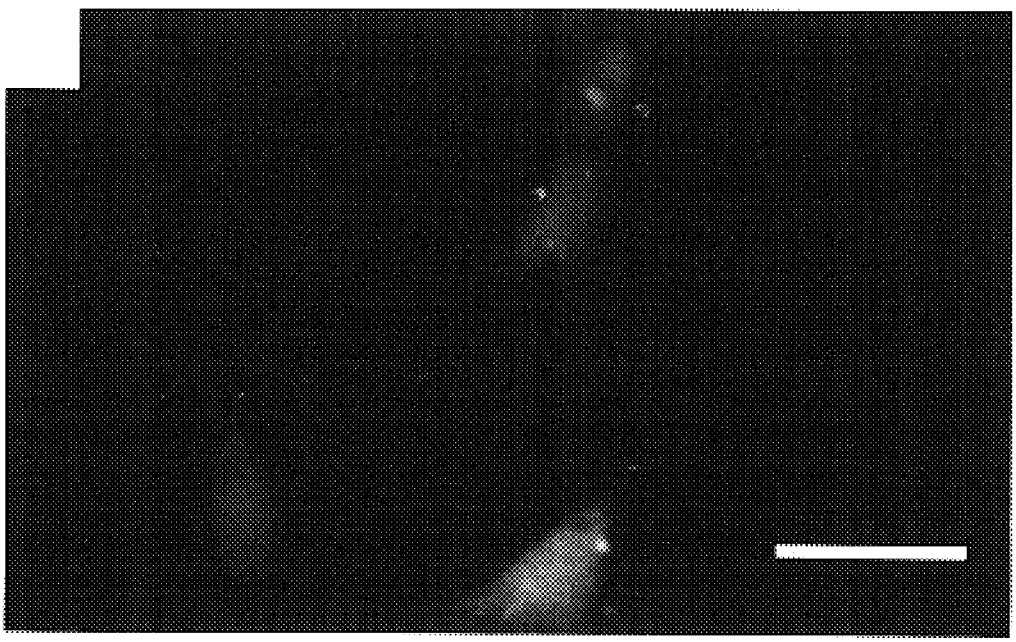

FIG. 10 presents a graph illustrating the increased rate of progesterone-induced maturation of oocytes injected with an SH3 domain-binding peptide, VLKRPLPIPPVTR (SEQ ID NO:64), of the present invention. Briefly, Stage VI oocytes were prepared and injected as previously described (see, Kay, B. K., in *Methods in Cell Biol.* (1991) 36:663–669). Oocytes were injected with 40 nL of 100 μM test peptide or water. After injection, the oocytes were placed in 2 μg/mL progesterone (Sigma, St. Louis, Mo.) and scored hourly for germinal vesicle breakdown (GVBD).

FIG. 11 shows the results of fluorescence experiments in which certain peptides, Panel A=VLKRPLPIPPVTR (SEQ ID NO:64), Panel B=GILAPPVPPRNTR (SEQ ID NO:63), Panel C=RSTPRPLPPLPTTR (SEQ ID NO:67), of the invention were shown to localize within cellular compartments thought to contain Src or Src-related proteins.

5. DETAILED DESCRIPTION OF THE PREFERRED EMBODIMENTS

5.1. General Considerations

The present invention relates to peptides that exhibit a binding affinity for an SH3 domain, which domain has been found to be present in a number of physiologically significant proteins. In particular, peptides are disclosed which exhibit general binding characteristics to the SH3 domains found in a group of proteins, including but not limited to Abl, Src, Grb2, PLC-δ, PLC-γ, Ras GAP, Nck, and p85 PI-3'Kinase. Preferred peptides exhibit selective, if not specific, binding affinity for the SH3 domain of Src. As described herein, the peptides of the present invention include a core sequence, preferably a consensus sequence, and additional amino acid residues that flank the core sequence. These peptides, including the methods for their identification, are described in greater detail, below.

Thus, in a specific embodiment of the invention, peptides are provided which have at least nine and up to about forty-five amino acid residues, including an amino acid sequence resembling the formula, R-2-L-P-5-6-P-8-9 (SEQ ID NO:10), positioned anywhere along the peptide. In the above-mentioned formula, each number represents an amino acid residue, such that 2 represents any amino acid residue except cysteine, 5 and 6 each represents a hydrophobic amino acid residue, 8 represents any amino acid residue except cysteine, and 9 represents a hydrophilic amino acid residue except cysteine. Each letter used in the formulas herein represent the standard one-letter symbol for the corresponding amino acid. When the peptide is a 9-mer, the peptide R-P-L-P-P-L-P-T-S (SEQ ID NO:11) is excluded. The peptides of particular interest are those that exhibit a binding affinity for the SH3 domain of Src and Src-related proteins, including Yes, Fyn, Lyn, Lck, Hck and Fgr. Preferably, the peptides of the invention exhibit a binding affinity for the SH3 domain of Src, which is at least three-fold, more preferably at least four-fold, most preferably at least about five-fold greater than that exhibited by the peptide RPLPPLP (SEQ ID NO:9). In still other embodiments, the peptides exhibit a binding affinity for the SH3 domain of Src which is at least ten-fold greater than that exhibited by the peptide RPLPPLP (SEQ ID NO:9).

In specific embodiments, peptides are disclosed in which the various amino acid residues at the indicated positions may independently have the following preferred identities: 2 is a P, R, A, L, Q, E or S, more preferably P or R; 5 represents a P, M, I or L, more preferably P or M; 6 is a P, L, I or V, more preferably P or L; 8 is a T, R, P, I, N, E, V, S, A, G or L, more preferably T or R; and 9 is a T, R, S, H or D, more preferably T or R. Despite the preference for hydrophobic amino acid residues at 5 and 6, in some cases it may be desirable to have hydrophilic amino acid residues at these positions. Specifically, amino acid residue 5 may be a T, R or S, and amino acid residue 6 may be a T or R. Likewise, while a hydrophilic amino acid residue is preferred at position 9, in some instances a hydrophobic residue, such as a P or A, may be desirable.

The present invention also contemplates SH3 domain-binding peptides with a minimum length of 10, 11, 12, 13, 14, 15 or more amino acids. Such peptides contain additional amino acid residues flanking the core sequence of R-2-L-P-5-6-P (SEQ ID NO:71) either at the C-terminal end, the N-terminal end or both. Thus, for example, such peptides include those that further comprise a C-terminal-flanking amino acid sequence of the formula 10, 10-11, 10-11-12, 10-11-12-13 (SEQ ID NO:12) or 10-11-12-13-14

(SEQ ID NO:13), in which each number represents any amino acid residue except cysteine, such that the amino acid residue 10 is bound to the amino acid residue 9 by a peptide bond. In that case, specific embodiments include an amino acid residue 10 which is T, R, L, S, D, P, A or N, preferably T or R, an amino acid residue 11 which is R, P, A, Q, S or T, preferably R or P, an amino acid residue 12 which is P, S, R or T, preferably P or S, an amino acid residue 13 which is P, S, R, F, H or T, preferably P or S, and an amino acid residue 14 which is S, R, G or T, preferably, S or R.

Furthermore, peptides are also provided which further comprise an N-terminal-flanking amino acid sequence of the formula 1', 2'-1', 3'-2'-1' or 4'-3'-2'-1' (SEQ ID NO:14) in which each number represents any amino acid residue except cysteine, such that 1' is bound to R by a peptide bond. In such a case, specific embodiments are provided in which the amino acid residue 1' is T, P, S, N, F, W, K, H, Q or G, preferably T or P, wherein the amino acid residue 2' is S, T, G, P, R, Q, L, A or H, preferably S or T, wherein the amino acid residue 3' is R, S, P, G, A, V, Y or L, preferably S or T, and wherein the amino acid residue 4' is R, S, V, T, G, L or F, preferably R or S.

In a particular embodiment, a peptide is disclosed having at least thirteen and up to forty-five amino acid residues, including an amino acid sequence of the formula, 3'-2'-1'-R-2-L-P-5-6-P-8-9-10 (SEQ ID NO:15), positioned anywhere along the peptide, in which each number represents an amino acid residue, such that 3', 2', 1', 2, 8, and 10 each represents any amino acid residue except cysteine, 5 and 6 each represents a hydrophobic amino acid residue, and 9 represents a hydrophilic amino acid residue except cysteine, each letter being the standard one-letter symbol for the corresponding amino acid, said peptide exhibiting a binding affinity for the SH3 domain of Src. Preferred 13-mers include, but are not limited to, those having an amino acid residue 5 which is a P or M, an amino acid residue 1' which is T, P, S or N, an amino acid residue 2' which is S or T, an amino acid residue 3' which is R or S, and an amino acid residue 10 which is T or R. In all the SH3 domain-binding peptides described herein, the prohibition against the use of the hydrophilic amino acid residue cysteine (C) does not extend beyond the 7-mer "core" sequence and the additional amino acid residues flanking the core up to a total (core+ flanking) of about 20 amino acids. That is, the occasional use of a cysteine is not absolutely prohibited. What should be kept in mind is that the potential for the formation of intramolecular disulfide bonds, to form a cyclic structure, be minimized as much as possible. Applicants have found that cyclized structures appear to be disfavored, at least with potential binding peptides of less than about 15 amino acid residues in length. The concern for the formation of cyclized structures comprising the core sequence diminishes with increasing size of the peptide. Presumably, a large enough structure, though cyclic, may allow the critical core sequence to adopt a more or less linear conformation.

In particular, specific peptides are disclosed which exhibit binding affinities to SH3 domains. These include the peptides, RSTPRPLPMLPTTR (SEQ ID NO. 62), RSTPRPLPPLPTTR (SEQ ID NO. 67), GILAPPVPPRNTR (SEQ ID NO. 63), VLKRPLPIPPVTR (SEQ ID NO. 64), GPHRRLPPTPATR (SEQ ID NO. 65), and ANPSPATRPLPTR (SEQ ID NO. 66).

Phage clones are also disclosed, along with the amino acid sequences that are responsible for SH3 domain binding. These phage clones are identified in FIG. 5.

In other embodiments of the present invention, SH3 domain-binding peptides are contemplated which have a total of 11, 13, 14, 18, 20, 22, 23, 25, 30, 36, 38 or 45 amino acid residues.

The peptides of the present invention, having been disclosed herein, may be prepared by any number of practicable methods, including but not limited to solution-phase synthesis, solid-phase synthesis, protein expression by a transformed host, cleavage from a naturally-derived, synthetic or semi-synthetic polypeptide, or a combination of these techniques.

The SH3 binding peptides exhibit a wide range of biological activity which includes the enhancement (or inhibition, depending on the particular peptide or the nature of the peptide's target molecule, in this case a protein bearing an SH3 domain) of the natural function or biological activity of the peptide's target molecule. For example, the interaction of the binding peptide of the present invention could result in the modulation of the oncogenic activity of the target molecule bearing the SH3 domain. If the target molecule has, in turn, a natural binding partner or ligand, the peptides of the present invention may also exhibit antagonistic or agonistic activity in relation to the biological activity of the natural binding partner.

Thus, it is an object of the present invention to provide a method of activating Src or Src-related protein tyrosine kinases by administering an effective amount of the SH3 domain-binding peptides generally described herein. The intensity of the immune response can thus be stimulated, for example, by the increased production of certain lymphokines, such as TNF-alpha and interleukin-1. As is generally known to those of ordinary skill in the art, a more intense immune response may be in order in certain conditions, such as in combating a particularly tenacious infection, viral or otherwise, or a malignancy.

Furthermore, in a specific embodiment of the present invention, a conjugate compound is contemplated which comprises the peptide of the present invention and a second chemical moiety. The second chemical moiety can be selected from a wide variety of chemical compounds including the peptide itself. Typically, however, the second chemical moiety is selected to be other than the peptide of the present invention, including but not limited to an amino acid, a peptide other than an SH3 binding peptide of the present invention, a polypeptide or protein (i.e., the conjugate is a fusion protein), a nucleic acid, a nucleoside, a glycosidic residue (i.e., any sugar or carbohydrate), a label or image-enhancing agent (including metals, isotopes, radioisotopes, chromophores, fluorophores (such as FITC, TRITC, and the like), and enzyme substrates), a drug (including synthetic, semisynthetic, and naturally-occurring compounds), small molecules (e.g., biotin, hormones, factors) and the like.

The peptide of the present invention can be conjugated to the second chemical moiety either directly (e.g., through appropriate functional groups, such as an amine or carboxylic acid group to form, for example, an amine, imine, amide, ester, acyl or other carbon—carbon bond) or indirectly through the intermediacy of a linker group (e.g., an aliphatic or aromatic polyhydroxy, polyamine, polycarboxylic acid, polyolefin or appropriate combinations thereof). Moreover, the term "conjugate," as used herein, is also meant to encompass non-covalent interactions, including but not limited to ionic, affinity or other complexation interactions. Preferably, such other non-covalent interactions provide definable, most preferably, isolatable chemical conjugate species.

As described further herein, the peptides of the present invention have been shown to localize within certain cellular compartments which contain Src or Src-related proteins.

Consequently, the above-described conjugate can be utilized as a delivery system for introduction of a drug to cells, tissues or organs that include SH3 domain-containing proteins.

It should also be pointed out that the present invention seeks to provide a recombinant construct comprising a nucleic acid or its complement that includes codons or nucleotide sequences encoding a peptide having a region that binds to an SH3 domain, preferably the Src SH3 domain. The recombinant nucleic acid may be a DNA or RNA polynucleotide.

In a specific embodiment, the present invention contemplates a recombinant construct which is a transforming vector. Such vectors include those well known to those of ordinary skill in the art, which effect the transfer or expression of the nucleotide sequence after introduction to a host, such as recombinant plasmid, phage or yeast artificial chromosome. These vectors may be closed circular loops or they may be linearized. The vectors contemplated include those that exist extrachromosomally after host transformation or transfection, as well as those that integrate within or even displace portions of the host chromosome. The vectors may be introduced to the cell with the help of transfection aids or techniques well-known in the art. For example, these aids or techniques may take the form of electroporation, use of calcium chloride, calcium phosphate, DEAB dextran, liposomes or polar lipid reagents known as LIPOFECTIN™ transfection promoter or LIPOFECTAMINE™ transfection promoter. In addition, the present invention contemplates the direct introduction of the desired nucleic acid to the host cell, for instance, by injection.

Transformed host cells are also obtained by the methods of the present invention which are capable of reproducing the polynucleotide sequences of interest and/or expressing the corresponding peptide products. A variety of hosts are contemplated, including prokaryotic and eukaryotic hosts. In particular, bacterial, viral, yeast, animal, and plant cells are potentially transformable hosts. Thus, a method is disclosed to obtain a transformed host cell that can produce, preferably secrete, a peptide having a region that binds to an SH3 domain comprising (a) providing an expression vector, preferably a secretory expression vector, comprising a nucleotide sequence encoding at least one copy of a peptide having a region that binds to an SH3 domain; and (b) introducing the vector to a competent host cell.

The peptides, thus produced, may then be introduced to cells, tissues, organs, or administered to the subject for the purpose of modulating the biochemical activity of the SH3 domain-containing proteins present therein. Accordingly, in specific embodiments of the present invention, compositions are provided which comprise an SH3 domain-binding peptide, including a core sequence and flanking sequences, and a suitable carrier.

The compositions contemplated by the present invention may also include other components, from those that facilitate the introduction or administration of the compositions to those that have their own innate activity, such as a prophylactic, a diagnostic or a therapeutic action. Such innate activity may be distinct from that of the peptides of the present invention or be complementary thereto. In any event, the compositions of the present invention include those that are suitable for administration into mammals, including humans. Preferably, the compositions (including necessarily the carrier) of the present invention are sterile, though others may need only be cosmetically, agriculturally or pharmaceutically acceptable. Still other compositions may be adapted for veterinary use.

The compositions, including the drug delivery systems described herein, are contemplated to be administered in a variety of ways, such as parenterally, orally, enterally, topically or by inhalation. The compositions may also be administered intranasally, opthalmically or intravaginally. Furthermore, the compositions of the invention can take several forms, such as solids, gels, liquids, aerosols or patches.

In another embodiment of the present invention a method is provided of identifying a peptide having a region that binds to an SH3 domain comprising: (a) providing an immobilized target protein comprising an SH3 domain; (b) incubating the immobilized target protein with an aliquot taken from a phage-displayed random peptide library, which library includes peptides having a random sequence of $\geq 8$ amino acid residues; (c) washing unbound phage from the immobilized target protein; (d) recovering the phage bound to the immobilized target protein; and (e) determining the relevant nucleotide sequence of said binding phage nucleic acid and deducing the primary sequence corresponding to the SH3 domain-binding peptide. Preferably, the method further comprises amplifying the titer of the recovered phage and repeating the steps of incubation, washing and recovery to provide SH3 domain-binding peptide-enriched phage.

Any other mode by which the peptide library, random or otherwise, can be "displayed" can be utilized in the present invention, however. Moreover, the present applicants believe that longer random peptide sequences (e.g., >6 amino acid residues, preferably >10, and most preferably, >12) provide not only much greater diversity but also a richer degree of secondary structure conducive to binding activity. If the random region of the peptide is less than or equal to an 8-mer, it should preferably not be cyclized.

5.2. Preparation of Random Peptide Libraries

The preparation and characterization of the preferred phage-displayed random peptide libraries have been described elsewhere. See, for example, Kay, B. K. et al. in *Gene* (1992) 128:59–65, for a description of the preparation of the phage-displayed random peptide library known as TSAR-9, more below. In particular, by cloning degenerate oligonucleotides of fixed length into bacteriophage vectors, recombinant libraries of random peptides can be generated which are expressed at the amino-terminus of the pIII protein on the surface of M13 viral particles. (There are 3–5 copies of the pIII-fusion on the surface of each particle.) Phage display offers several conveniences: first, the expressed peptides are on the surface of the viral particles and accessible for interactions; second, the recombinant viral particles are stable (i.e., can be frozen, exposed to pH extremes); third, the viruses can be amplified; and fourth, each viral particle contains the DNA encoding the recombinant genome. Consequently, these libraries can be screened by isolating viral particles that bind to targets. The isolates can be grown up overnight, and the displayed peptide sequence responsible for binding can be deduced by DNA sequencing.

These libraries have approximately $>10^8$ different recombinants, and nucleotide sequencing of the inserts suggests that the expressed peptides are indeed random in amino acid sequence. These libraries are referred to herein as TSAR libraries, where TSAR stands for Totally Synthetic Affinity Reagents. The preparation of the TSAR libraries are described further below.

5.3. SH3 Binding Clones and Their Characteristics

Accordingly, peptides have been isolated from an unconstrained random peptide library which exhibit a binding affinity for SH3 domains. Furthermore, the binding affinities exhibited by the disclosed peptides differ in their selectivities with certain peptides showing comparable binding affinities for SH3 domains derived from different proteins, while others manifest greater affinities for specific SH3 domains.

The amino acid sequence of various peptides isolated by the present method are listed in FIG. 5 and Table 1. As can be seen from this list, certain groups of SH3 domain binding peptides are isolated from three separate random peptide libraries, each based on a different type of random peptide insert, all displayed at the amino-terminus of the pIII protein on the surface of M13 viral particles. Ten clones were isolated from the R8C library, seven from the TSAR-12 library, and seven from the TSAR-9 library. The sequences are presented to highlight the particular amino acid residues believed to bind directly to the SH3 domain, as well as to point out the remaining amino acid residues of the random insert and the viral flanking sequences and complementary site amino acid residues common to each group of clones. The frequency with which each particular clone is found in each library is also indicated in FIG. 5. Thus, clones T12.SRC3.1 and T12.SRC3.2 are by far the most abundant clones found among the three libraries.

Interestingly, all the binding peptides are found to have the proline-rich amino acid residue motif, which is apparently responsible for binding, the motif being located predominantly at the C-terminal end of the insert, although each clone also contains an insert at the N-terminal end. The significance of this observation is not presently understood, although this finding may indicate the possible importance of the C-terminal viral flanking sequences in SH3 domain binding.

Indeed, a synthetic peptide bearing only the core consensus sequence RPLPPLP (SEQ ID NO:9) was less effective in binding to target SH3 domains than synthetic peptides that also included additional amino acid residues flanking the core sequences. Thus, 13-mers and 14-mers having the sequences RSTPRPLPMLPTTR (SEQ ID NO:62), RSTPRPLPPLPTTR (SEQ ID NO:67), GILAPPVPPRNTR (SEQ ID NO:63), GPHRRLPPTPATR (SEQ ID NO:65), and VLKRPLPIPPVTR (SEQ ID NO:64) have been prepared and shown to bind to SH3 domains, such as those of Src and Yes, much more avidly than the 7-mer, RPLPPLP (SEQ ID NO:9). The 13-mer ANPSPATRPLPTR (SEQ ID NO:66) has been shown to have binding affinities comparable to the core consensus sequence. In each case, the 13-mers comprise a 7-mer "core" sequence plus additional amino acid residues flanking same, some of which additional amino acid residues are contributed by the viral flanking sequences.

Thus, in one embodiment of the present invention, a 7-mer core includes a consensus motif of the formula RXLPøøP (SEQ ID NO:71), wherein R is arginine, L is leucine, P is proline, x represents any amino acid except cysteine and ø represents a hydrophobic amino acid residue.

By "hydrophobic amino acid residue," the applicants mean to include F, Y, W, V, A, I, L, P or M, each letter representing the standard one-letter designation for the corresponding amino acid residue.

Furthermore, a preferred 9-mer peptide comprising two additional amino acids on the C-terminal end of the core sequence is envisioned having a consensus motif of the formula RXLPøøPXψ. In this preferred 9-mer consensus motif, the symbol ψ represents a hydrophilic amino acid residue, except cysteine. By "hydrophilic amino acid residue," the applicants mean to include K, R, H, D, E, N, Q, T, S or C, and the other symbols are as defined above. For the purposes of the present invention, a glycine residue (G) may be considered either a hydrophobic or a hydrophilic amino acid residue. The one-letter symbols B and Z, which stand for N or D and Q or E, respectively, are considered hydrophilic amino acid residues.

Particular 13-mer peptides of the present invention include those listed, below. It is noted, however, that not all the following 13-mer peptides correlate strictly to or comply with the preferred 9-mer consensus motif, described above. Those peptides that do not comply (indicated in italics, with the non-complying amino acid residues underscored) can, thus, be described as "resembling" those that do comply (indicated in normal type) with the preferred 9-mer consensus motif: PGFRELPPLPPSR (SEQ ID NO:72), AQSRPLPIPPETR (SEQ ID NO:73), VLKRPLPIPPVTR (SEQ ID NO:64), PPNSPLPPLPTHL (SEQ ID NO:74), TGRGPLPPLPNDS (SEQ ID NO:75), YSTRPVPPITRPS (SEQ ID NO:76), SHKSRLPPLPTRP (SEQ ID NO:77), YRFRALPSPPSAS (SEQ ID NO:78), GPHRRLPPTPATR (SEQ ID NO:65), LAQRQLPPTPGRD (SEQ ID NO:79), ALQRRLPRTPPPA (SEQ ID NO:80), PATRPLPTRPSRT (SEQ ID NO:81), YSTRPLPSRPSRT (SEQ ID NO:82), XPGRILLLPSEPR (SEQ ID NO:83), SGGILAPPVPPRN (SEQ ID NO:84), RSTRPLPILPRTT (SEQ ID NO:85), STPRPLPMLPTTR (SEQ ID NO:86), STNRPLPMIPTTR (SEQ ID NO:87), RSTRPLPSLPITT (SEQ ID NO:88), STSRPLPSLPTTR (SEQ ID NO:89), RSTRSLPPLPPTT (SEQ ID NO:90), RSTRQLPIPPTTT (SEQ ID NO:91), STPRPLPLIPTTP (SEQ ID NO:92), RSTRPLPPTPLTT (SEQ ID NO:93), and RSTRPQPPPPITT (SEQ ID NO:94). Accordingly, other peptides not specifically disclosed, which either comply with or "resemble" the preferred 9-mer consensus motif, can be readily envisioned by those of ordinary skill in the art and are considered to be equivalent to those that are specifically disclosed above. In particular, non-compliance at positions 1 (S, G, and I, in place of R, are tolerated), 3 (V, A, and Q, in place of L, are tolerated), 4 (L, in place of P, is tolerated), 5 (hydrophilic amino acid residues, S, R, and T, are tolerated in place of a hydrophobic amino acid residue), 6 (hydrophilic amino acid residues, R and T, are tolerated in place of a hydrophobic amino acid residue), 7 (T, and S, in place of P, are tolerated), and 9 (P and A are tolerated in place of a hydrophilic amino acid residue) have been observed.

TABLE 1

SEQ ID NOS OF THE SEQUENCES SHOWN IN FIG. 5

| SEQ ID NO: | CLONE | SEQUENCE | | |
| --- | --- | --- | --- | --- |
| 38 | T9, SRC3, 2 | SSFFDQQWDYSIAEKMHPIRPGF | RELPPLP | PSRASFGGGASRPSR |
| 39 | T12, SRC3, 4 | STNVWVTGSVIARGAQS | RPLPIPP | ETRPSR |
| 40 | T12, SRC3, 6 | STAPWGLRVAHEGGVLK | RPLPRPP | VTRPSR |
| 41 | T9, SRC3, 4 | SSSGYVVPKRLGDMREYNAHPGLHVPPN | SPLPPLP | THLQSSRPSR |

TABLE 1-continued

SEQ ID NOS OF THE SEQUENCES SHOWN IN FIG. 5

| SEQ ID NO: | CLONE | SEQUENCE | | |
|---|---|---|---|---|
| 42 | T9, SRC3, 6 | SSRGEGNNIISSRPFLSNSDPGVSNKLTGR | GPLPPLP | NDSRPSR |
| 43 | T12, SRC3, 7 | STAVSFRFMPGGGGAFYST | RPVPPIT | RPSRT |
| 44 | T12, SRC3, 5 | STAHSLWDWGTFSGVSHKS | RLPPLPT | RPSRT |
| 45 | T9, SRC3, 7 | PGYARIVSYRF | RALPSPP | SASRPSR |
| 46 | T12, SRC3, 3 | STNDVDWMHMWNSGGPH | RRLPPTP | ATRPSR |
| 47 | T9, SRC3, 5 | SSDNWARRVHASEKIYTDLSPGILLAQ | RQLPPTP | GRDPSHSRPSR |
| 48 | T9, SRC3, 1 | SSESPLMYNRVGALQSLTSVPGSMMHFALQ | RRLPRTP | PPASRPSR |
| 49 | T12, SRC3, 2 | STRWSHSWPGYVGGANPSPAT | RPLPTRP | SRTVESC |
| 50 | T9, SRC3, 3 | SRYNDLGTRPVSEVIKYDYFPGYSQHVITPDGSYST | RPLPSRP | SRTVESC |
| 51 | T9, SRC3, 8 | PG | RILLLPS | EPRTFYNYGHDSRPSR |
| 52 | T12, SRC3, 1 | STMYGVSWLSSGSGGILA | PPVPPRN | TRPSR |
| | | CONSENSUS | RPLPPLP | |
| 53 | R8C, YES3, 6 | SSCTEKTVSGWCGSRST | RPLPILP | RTTRPSR |
| 54 | R8C, YES3, 5 | SSCMLPTDGWQCGSRSTP | RPLPMLP | TTRPSR |
| 55 | R8C, YES3, 3 | SSCDGTQFRLNCGSRSTN | RPLPMIP | TTRPSR |
| 56 | R8C, YES3, 1/SRC3.1 | SSCMQGQAGLKCGSRST | RPLPSLP | ITTRPSR |
| 57 | R8C, YES3, 7/SRC3, 2 | SSCYREKDTWGCGSRSTS | RPLPSLP | TTRPSR |
| 58 | R8C, YES3, 2 | SSCLFEQGAGTCGSRST | RSLPPLP | PTTRPSR |
| 106 | R8C, YES3, 4 | SSCDHTLGLGWCGSRST | RQLPIPP | TTTRPSR |
| 59 | R8C, YES3, 10 | SSCDTGRIAPGCGSRSTP | RPLPLIP | TTPRSTNLNLTSTTTRPSR |
| 60 | R8C, YES3, 8 | SSCGLDNAAKTCGSRST | RPLPPTP | LTTRPSR |
| 61 | R8C, YES3, 9 | SSCSRAHETEMCGSRST | RPQPPPP | ITTRPSR |
| | | CONSENSUS | RPLPPLP | |

5.3.1. Binding Specificities

It has been discovered that certain of the binding peptides disclosed have a greater relative binding affinity for one SH3 domain over another. Referring now to FIG. 8, the relative binding affinities of the various peptides described above toward different SH3 domain targets are graphically presented. As one can see, the relative binding affinities of the respective peptides can differ by orders of magnitude. Thus, as shown in FIG. 8, the peptide GPHRRLPPTPATR (SEQ ID NO:65), having the relevant sequence of the phage clone identified as T12.SRC3.3, is specific to Src family SH3 domains, including, but not limited to, Src, Yes, Lck, Hck, Fgr, Fyn, and Lyn. This SH3 binding peptide has little affinity for SH3 domains derived from PLCγ or Grb2. On the other hand, the peptide GILAPPVPPRNTR (SEQ ID NO:63), corresponding to the relevant sequence of the phage clone T12.SRC3.1, which is one of the most abundant binding clones found by the present method, binds generically to a broad range of SH3 domains, including Src, PLCγ, and Grb2.

On an intermediate level, the present invention has also uncovered a peptide, VLKRPLPIPPVTR (SEQ ID NO:64), corresponding to the relevant sequence of the phage clone T12.SRC3.6, which is Src preferential; that is, this peptide exhibits strong binding affinities for members of the Src family, some binding affinities for Grb2 proteins, but little binding affinities for PLCγ domains. The peptide ANPS-PATRPLPTR (SEQ ID NO:66), corresponding to the relevant sequence of the phage clone T12.SRC3.2, also exhibits Src family specificity similar to GPHRRLPPTPATR (SEQ ID NO:65). The peptides RSTPRPLPMLPTTR (R8C.YES3.5; SEQ ID NO:62) and RSTPRPLPPLPTTR (representative consensus motif; SEQ ID NO:67) are highly specific for SH3 domain of Src, Yes, and other Src-related proteins.

5.4. Further Discussion of Binding Experiments

At the outset it is apparent that the binding affinity of certain peptides to the SH3 domain of Src and Src-related proteins is governed by more than just the presence of the preferred core consensus sequences, RPLPPLP (SEQ ID NO:9) or RPLPMLP (SEQ ID NO:95; i.e., RPLP(P/M)LP, SEQ ID NO:96). Thus, while the synthetic peptides RST-PRPLPMLPTTR (R8C.YES3.5; SEQ ID NO:62) and RST-PRPLPPLPTTR (consensus; (SEQ ID NO:67) exhibit a strong specific binding affinity for Src SH3, the other synthetic peptides tested also exhibited an avid binding affinity to SH3 domains relative to the 7-mer, RPLPPLP (SEQ ID NO:9). These other peptides, GILAPPVPPRNTR (SEQ ID NO:63), VLKRPLPIPPVTR (SEQ ID NO:64), GPHRRLPPTPATR (SEQ ID NO:65), and ANPSPATR-PLPTR (SEQ ID NO:66), sport core sequences and flanking sequences that do not closely adhere to the preferred core consensus sequences. Thus, these results suggest that binding affinity to SH3 domains is governed to a large extent by the nature of the amino acid residues flanking the core 7-mer sequence.

The binding characteristics of Src SH3-selected peptides was determined using synthetic biotinylated peptides corresponding to the sequences displayed by Src SH3-selected phage. These biotinylated peptides were assayed for direct binding to immobilized Src SH3-GST. Each of the five library-derived peptides tested were found to bind to Src SH3-GST and Yes SH3-GST over background (FIG. 8). Furthermore, a strong correlation was observed between the similarity of a given peptide to the preferred core consensus sequence RPLP(P/M)LP and the peptide's affinity for Src SH3-GST. The core sequence of the clone T12.SRC3.1 (GILAPPVPPRNTR; SEQ ID NO:63) appears to provide more generic SH3 domain-binding characteristics.

Experiments comparing the relative binding of various phage clones to SH3 domains taken from a variety of proteins demonstrated the preference of these clones for Src and Src-related SH3 domains over SH3 domains taken from other proteins.

It was further found that while the 7-mer having the consensus sequence RPLPPLP (SEQ ID NO:9) bound to Src SH3-GST only weakly, peptides comprising the consensus sequence flanked by residues encoded by one of the Src SH3-selected clones (R8C.YES3.5), RSTP (SEQ ID NO:97) at the N-terminal end and TTR at the C-terminal end, bound significantly better than any of the peptides tested (FIG. 7). Thus, as stated previously, sequences that flank the RPLP (P/M)LP (SEQ ID NO:96) core appear to be important contributors to SH3 binding. It is further surmised that a peptide having or resembling the sequence RSTPAPPVP-PRTTR (SEQ ID NO:98) should exhibit strong but generic binding to a variety of SH3 domains.

Similarly, it is observed that most of the Src SH3-binding motifs are located near the carboxy-terminus of the random peptides, adjacent to sequences which are fixed in every clone (FIG. 5). The exceptional clones tend to possess sequences that resemble motifs that include fixed flanking sequences. This clustering contrasts with previous results, in which binding motifs are distributed throughout the random peptide. Kay, B. K., et al., in *Gene* (1993) 128:59–65.

The binding of the library-derived Src SH3-binding peptides was compared to that of peptides corresponding to proline-rich regions of natural proteins. Peptides corresponding to SH3-binding regions in human PI-3' Kinase (KISPPTPKPRPPRPLPV; SEQ ID NO:69) and human SOS1.20 (GTVEPVPPPVPPRRRPESA; SEQ ID NO:68), as well as a proline-rich region of the cytoskeletal protein vinculin (LAPPKPPLPEGEV; SEQ ID NO:70), bound Src SH3 less well than the library-derived peptides (FIG. 7).

As mentioned above, the relative specificity of binding was explored. Thus, the relative binding of Src SH3-selected peptides to equal amounts of GST fusions to SH3 domains from different proteins was determined (FIG. 8). While all of the library-derived peptides bound the Src and Yes SH3 domains almost equally well, none of the peptides (with the exception of peptide T12.SRC3.1, the most divergent peptide tested) bound the SH3 domains of Grb2, Crk, Abl or PLCγ1 appreciably. Thus, the library-derived peptides, in contrast with a peptide derived from SOS1, exhibit SH3 binding that is relatively specific for Src-family members.

Next, it was determined whether the binding to the Src SH3 domain was qualitatively like the interactions of the SH3 domain and natural proteins found in cell lysates. Thus, radiolabeled proteins were prepared from NIH 3T3 cell lysates and chromatographed over Src SH3-GST immobilized on glutathione linked SEPHAROSE™ agarose. SDS-PAGE shows that a number of proteins can be affinity purified in this manner. The synthesized peptides bind quite well to the Src SH3 domain, as they can compete the binding of radiolabeled proteins from cell lysates to immobilized Src-GST, with an $IC_{50}$ of 1–10 mM (FIG. 9). In conclusion, the peptides can efficiently block the interaction of cellular proteins with Src SH3 in vitro.

Moreover, *Xenopus laevis* oocytes injected with mRNA encoding constituitively active Src undergo progesterone-induced maturation at an accelerated rate relative to oocytes injected with water or c-Src mRNA. Unger, T. F. and Steele, R. E. in *Mol. Cell. Biol.* (1992) 12:5485–5498. To explore the ability of the library-derived Src SH3-binding peptides to exert a biochemical effect in vivo, the influence of the peptides on the maturation of *Xenopus laevis* oocytes was examined. Hence, stage VI oocytes were injected with peptide, exposed to progesterone, and scored for germinal vesicle breakdown. FIG. 10 shows that the rate of maturation was accelerated by approximately one hour when oocytes were injected with the SH3-binding peptide consisting of RPLPPLP (SEQ ID NO:9) flanked by residues from clone T12.SRC3.6 (VLKRPLPIPPVTR; SEQ ID NO:64), but not with water or a peptide corresponding to a proline-rich segment of vinculin (LAPPKPPLPEGEV; SEQ ID NO:70) as controls. The magnitude of this effect is roughly equivalent to that seen with injection of mRNA encoding constituitively active Src. See, e.g., FIG. 3B in Unger, T. F. and Steele, R. E., supra. This result suggests that the library-derived Src SH3-binding peptide is effectively relieving an inhibitory effect of the Src SH3 domain upon Src PTK activity. This model is consistent with a number of studies which have demonstrated an inhibitory effect of the Src SH3 domain upon Src kinase and transforming activity. See, e.g., Okada, M., et al., supra; Murphy, S. M., et al., supra; and Superti-Furga, G., et al., supra.

5.5. Diagnostic and Therapeutic Agents Based on SH3 Binding Peptides and Additional Methods of Their Use As already indicated above, the present invention also seeks to provide diagnostic, prophylactic, and therapeutic agents based on the SH3 binding peptides described herein.

In one embodiment, diagnostic agents are provided, preferably in the form of kits, comprising an SH3 domain-binding peptide and a detectable label conjugated to said peptide directly, indirectly or by complexation, said peptide comprising: (i) a core sequence motif of the formula RXLPøøP (SEQ ID NO:71), wherein X represents any amino acid except cysteine and ø represents a hydrophobic amino acid residue, including F, Y, W, V, A, I, L, P, M or G, each letter representing the standard one-letter designation for the corresponding amino acid residue; and (ii) two or more additional amino acid residues flanking said core sequence at its C-terminal end, N-terminal end or both.

The diagnostic agents of the present invention can be used to detect the presence of SH3 domains of a generic or specific type in cells, tissues or organs either in vitro or in vivo. For in vivo applications, the diagnostic agent is preferably mixed with a pharmaceutically acceptable carrier for administration, either enterally, parenterally or by some other route dictated by the needs of the particular application.

In a particular embodiment, for example, an assay based on a fusion product is contemplated which comprises a Src SH3 domain-binding peptide of the invention and a substrate for deregulated or "activated" Src. For instance, a muscle biopsy, taken from a subject suspected of being infected by the Rous sarcoma virus, can be treated with an effective amount of the fusion product. By subsequent analysis of the degree of conversion of the substrate, one can potentially detect infection by the Rous sarcoma virus in the subject, particularly mammals, especially chickens. The presence of the retrovirus, which causes the expression of deregulated or "activated" Src, may thus be indicated by unusually high levels of Src as revealed by large amounts of the converted substrate. See, for example, Paxton, W. G. et al., in *Biochem. Biophys. Res. Commun.* (1994) 200(1):260–267 (detection of phosphorylated tyrosine and serine residues of angiotensin II AT1 receptor, a substrate of Src family tyrosine kinases); another suitable substrate may be the protein p68 (Fumagalli, S. et al., in *Nature* (1994) 368(6474):871–874; Taylor, S. J. and Shalloway, D., in *Ibid.* at 867–871.

Alternatively, the enzyme can be isolated by selective binding to a form of the SH3 domain-binding peptides of the present invention (e.g., biotin-peptide conjugate). After isolation of the protein-peptide conjugate complex (e.g., on a column comprising streptavidin), the activity of the enzyme can then be assayed by conventional methods to determine its level of protein kinase activity which can be taken as an indication of the presence of the deregulated or "activated"

form of the enzyme. An assay for Src kinase has been described by Klinz and Maness, in *Neuroprotocols* (a companion to *Neuroscience*)(1992) 1(3):224–231.

Moreover, the diagnostic agents of the invention can also serve as imaging agents of cells, tissues or organs, especially those that contain proteins with an SH3 domain. For example, neural cells (e.g., neurons, other areas of the brain), osteoclasts, osteoblasts, platelets, immune cells, and other dividing cells are known to express or contain proteins with SH3 domains. Thus, an image can be taken of portions of the body to serve as a baseline for subsequent images to detect physiologic or biochemical changes in the subject's body. For instance, changes in the condition of cellular levels of Src or a transformation of the cellular Src to an "activated" form may be detected using the diagnostic or imaging agents of the present invention.

Accordingly, it has been demonstrated that an SH3-binding peptide tagged with a fluorescence emitter can provide an image of the cytoskeleton. The images are presented in FIG. 11. As can be seen from FIG. 11, panels A, B, and C show the fluorescence image that is obtained on treating NIH 3T3 fibroblasts with SH3 domain-binding peptides modified to include a fluorescent tag. In sharp contrast, panel D shows only a dark image that is produced when the cells are treated with a proline-rich segment of vinculin as a control.

In another embodiment, an SH3 domain-binding peptide-horseradish immunoperoxidase complex or related immunohistochemical agent could be used to detect and quantitate specific receptor molecules in tissues, serum or body fluids. In particular, the present invention provides useful diagnostic reagents for use in immunoassays, Southern or Northern hybridization, and in situ assays. Accordingly, the diagnostic agents described herein may be suitable for use in vitro or in vivo.

In addition, the diagnostic or imaging agent of the present invention is not limited by the nature of the detectable label. Hence, the diagnostic agent may contain one or more such labels including, but not limited to, radioisotope, fluorescent tags, paramagnetic substances, heavy metals, or other image-enhancing agents. Those of ordinary skill in the art would be familiar with the range of label and methods to incorporate or conjugate them into the SH3 domain-binding peptide to form diagnostic agents.

In yet a further embodiment, pharmaceutical compositions are provided comprising an SH3 domain-binding peptide and a pharmaceutically acceptable carrier. In a specific embodiment of the invention, the pharmaceutical composition is useful for the modulation of the activity of SH3 domain-containing proteins. By "modulation" is meant either inhibition or enhancement of the activity of the protein target.

Accordingly, a pharmaceutical composition is disclosed comprising an SH3 domain-binding peptide and a pharmaceutically acceptable carrier, said peptide comprising: (i) a 9-mer sequence motif of the formula RXLPøøPXψ (SEQ ID No:10), wherein X represents any amino acid except cysteine, ø represents a hydrophobic amino acid residue, and wherein ψ is a hydrophilic amino acid residue except cysteine, each letter representing the standard one-letter designation for the corresponding amino acid residue; and, optionally, (ii) additional amino acid residues flanking the 9-mer sequence at its C-terminal end, N-terminal end or both, up to a total of 45 amino acid residues, including said 9-mer sequence. Preferably, the peptide comprises at least one, more preferably at least two, and most preferably at least three additional amino acids flanking the 9-mer sequence.

As stated above, the therapeutic or diagnostic agents of the invention may also contain appropriate pharmaceutically acceptable carriers, diluents and adjuvants. Such pharmaceutical carriers can be sterile liquids, such as water and oils including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin.

Such compositions will contain an effective therapeutic amount of the active compound together with a suitable amount of carrier so as to provide the form for proper administration to the subject. While intravenous injection is a very effective form of administration, other modes can be employed, including but not limited to intramuscular, intraperitoneal, and subcutaneous injection, and oral, nasal, enteral, and parenteral administration.

The therapeutic agents and diagnostic agents of the instant invention are used for the treatment and/or diagnosis of animals, and more preferably, mammals including humans, as well as dogs, cats, horses, cows, pigs, guinea pigs, mice and rats. Accordingly, other methods contemplated in the present invention, include, but are not limited to, a method of modulating, i.e., inhibiting or enhancing, bone resorption in a mammal (see, e.g., Hall, T. J., in *Biochem. Biophys. Res. Commun.* (1994) 199(3):1237–44), a method of disrupting protein tyrosine kinase-mediated signal transduction pathways or a method of regulating the processing, trafficking or translation of RNA in a cell by introducing or administering an effective amount of an SH3 domain-binding peptide of the present invention (see, e.g., Taylor, S. J. and Shalloway, D., supra).

The diagnostic or therapeutic agents of the present invention can be modified by attachment to soluble macromolecules such as proteins, polysaccharides, or synthetic polymers. For example, the peptide could be coupled to styrene-maleic acid copolymers (see, e.g., Matsumura and Maeda, *Cancer Res.* (1986) 46:6387), methacrylamide copolymers (Kopececk and Duncan, *J. Controlled Release* (1987) 6:315), or polyethylene glycol (PEG) (e.g., Hershfield and Buckley, *N. Engl. J. Med.* (1987) 316:589; Ho et al., *Drug Metab. Dispos.* (1986) 14:349; Chua et al., *Ann. Intern. Med.* (1988) 109:114).

The agents, if desired, are further targeted by attachment to an antibody, especially a monoclonal antibody. Such antibodies include but are not limited to chimeric, single chain, Fab fragments, and Fab expression libraries. In one embodiment the agent is coupled to the macromolecule via a degradable linkage so that it will be released in vivo in its active form.

In another embodiment, the therapeutic or diagnostic agent may be delivered in a vesicle, in particular a liposome. See, Langer, *Science* (1990) 249:1527–1533; Treat et al., in *Liposomes in the Therapy of Infectious Disease and Cancer*, Lopez-Berestein and Fidler (eds.), Liss, New York (1989) pp. 353–365; Lopez-Berestein, ibid., pp. 317–327.

In yet another embodiment, the therapeutic or in vivo diagnostic agent can be delivered in a controlled release system. In one embodiment, a pump may be used (see Langer, supra; Sefton, *CRC Crit. Ref. Biomed. Eng.* (1987) 14:201; Buchwald et al., *Surgery* (1980) 88:507; Saudek et al., *N. Engl. J. Med.* (1989) 321:574). In another embodiment, polymeric materials may be used (see Medical Applications of Controlled Release, Langer and Wise (eds.), CRC Pres., Boca Raton, Fla., 1974; Controlled Drug Bioavailability, Drug Product Design and Performance, Smolen and Ball (eds.) Wiley, New York 1984; Raner and Peppas, *J. Macromol. Sci. Rev. Macromol. Chem.* (1983) 23:61; see, also, Levy et al., *Science* (1985) 228:190; During et al., *Ann. Neurol.* (1989) 25:351; Howard et al., *J. Neurosurg.* (1989) 71:105). In a preferred embodiment, a controlled release system may be placed next to the therapeutic target, thus requiring only a fraction of the systemic dose (see, e.g., Goodson, in *Medical Applications of Controlled Release*, supra, (1984) 2:115–138). It will be recognized by one of ordinary skill in the art that a particular advantage of the invention is that a peptide will not be subject to the problems of denaturation and aggregation associated with proteins held in the warm, most environment of a body in a controlled release system.

Other controlled release systems are discussed in the review by Langer, in *Science* (1990) 249:1527–1533.

6. EXAMPLES

6.1. Preparation of the TSAR-9 Library

6.1.1. Synthesis and Assembly of Oligonucleotides

FIG. 1 shows the formula of the oligonucleotides and the assembly scheme used in construction of the TSAR-9 library. The oligonucleotides were synthesized with an applied Biosystems 380a synthesizer (Foster City, Calif.), and the full-length oligonucleotides were purified by HPLC.

Five micrograms of each of the pair of oligonucleotides were mixed together in buffer (10 mM Tris-HCl, pH 8.3, 15 mM KCl, 0.001% gelatin, 1.5 mM magnesium chloride), with 0.1% TRITON™ X-100, 2 mM dNTP's, and 20 units of TAQ™ DNA polymerase. The assembly reaction mixtures were incubated at 72° C. for 30 seconds and then 30° C. for 30 seconds; this cycle was repeated 60 times. It should be noted that the assembly reaction is not PCR, since a denaturation step was not used. Fill-in reactions were carried out in a thermal cycling device (Ericomp, LaJolla, Calif.) with the following protocol: 30 seconds at 72° C., 30 seconds at 30° C., repeated for 60 cycles. The lower temperature allows for annealing of the six base complementary region between the two sets of the oligonucleotide pairs. The reaction products were phenol/chloroform extracted and ethanol precipitated. Greater than 90% of the nucleotides were found to have been converted to double stranded synthetic oligonucleotides.

After resuspension in 300 μL of buffer containing 10 mM Tris-HCl, pH 7.5, 1 mM EDTA (TE buffer), the ends of the oligonucleotide fragments were cleaved with Xba I and Xho I (New England BioLabs, Beverly, Mass.) according to the supplier's recommendations. The fragments were purified by 4% agarose gel electrophoresis. The band of correct size was removed and electroeluted, concentrated by ethanol precipitation and resuspended in 100 μL TE buffer. Approximately 5% of the assembled oligonucleotides can be expected to have internal Xho I or Xba I sites; however, only the full-length molecules were used in the ligation step of the assembly scheme. The concentration of the synthetic oligonucleotide fragments was estimated by comparing the intensity on an ethidium bromide stained gel run along with appropriate quantitated markers. All DNA manipulations not described in detail were performed according to Maniatis, supra.

To demonstrate that the assembled enzyme digested oligonucleotides could be ligated, the synthesized DNA fragments were examined for their ability to self-ligate. The digested fragments were incubated overnight at 18° C. in ligation buffer with T4 DNA ligase. When the ligation products were examined by agarose gel electrophoresis, a concatamer of bands was visible upon ethidium bromide staining. As many as five different unit length concatamer bands (i.e., dimer, trimer, tetramer, pentamer, hexamer) were evident, suggesting that the synthesized DNA fragments were efficient substrates for ligation.

6.1.2. Construction of Vectors

The construction of the M13 derived phage vectors useful for expressing a TSAR library has been recently described (Fowlkes, D. et al. *BioTech.* (1992) 13:422–427). To express the TSAR-9 library, an M13 derived vector, m663, was constructed as described in Fowlkes. The m663 vector contains the pIII gene having a c-myc-epitope, i.e., as a stuffer fragment, introduced at the mature N-terminal end, flanked by Xho I and Xba I restriction sites (see also, FIG. 1 of Fowlkes).

6.1.3. Expression of the TSAR-9 Library

The synthesized oligonucleotides were then ligated to Xho I and Xba I double-digested m663 RF DNA containing, the pIII gene (Fowlkes) by incubation with ligase overnight at 12° C. More particularly, 50 ng of vector DNA and 5 ng of the digested synthesized DNA and was mixed together in 50 μL ligation buffer (50 mM Tris, pH 8.0, 10 mM MgCl$_2$, 20 mM DTT, 0.1 mM ATP) with T4 DNA ligase. After overnight ligation at 12° C., the DNA was concentrated by ethanol precipitation and washed with 70% ethanol. The ligated DNA was then introduced into *E. coli* (DH5αF'; GIBCO BRL, Gaithersburg, Md.) by electroporation.

A small aliquot of the electroporated cells was plated and the number of plaques counted to determine that $10^8$ recombinants were generated. The library of *E. coli* cells containing recombinant vectors was plated at a high density (~400,000 per 150 mM petri plate) for a single amplification of the recombinant phage. After 8 hr, the recombinant bacteriophage were recovered by washing each plate for 18 hr with SMG buffer (100 mM NaCl, 10 mM Tris-HCl, pH 7.5, 10 mM MgCl$_{21}$ 0.05% gelatin) and after the addition of glycerol to 50% were frozen at −80° C. The TSAR-9 library thus formed had a working titer of ~$2 \times 10^{11}$ pfu/ml.

6.2. Preparation of TSAR-12 Library

FIG. 2 shows the formula for the synthetic oligonucleotides and the assembly scheme used in the construction of the TSAR-12 library. As shown in FIG. 2, the TSAR-12 library was prepared substantially the same as the TSAR-9 library described in Section 6.1 above with the following exceptions: (1) each of the variant non-predicted oligonucleotide sequences, i.e., NNB, was 30 nucleotides in length, rather than 54 nucleotides; (2) the restriction sites included at the 5' termini of the variant, non-predicted sequences were Sal I and Spe 1, rather than Xho I and Xba I; and (3) the invariant sequence at the 3' termini to aid annealing of the two strands was GCGGTG and CGCCAC rather than CCAGGT and GGTCCA (5' to 3').

After synthesis including numerous rounds of annealing and chain extension in the presence of dNTP's and TAQ™ DNA polymerase, and purification as described above in Section 6.1.1, the synthetic double stranded, oligonucleotide fragments were digested with Sal I and Spe I restriction enzymes and ligated with T4 DNA ligase to the nucleotide sequence encoding the M13 pll gene contained in the m663 vector to yield a library of TSAR-expression vectors as described in Sections 6.1.2 and 6.1.3. The ligated DNA was then introduced into E. coli (DH5αF'; GIBCO BRL, Gaithersburg, Md.) by electroporation. The library of E. coli cells were plated at high density (~400,000 per 150 mm petri plate) for amplification of the recombinant phage. After about 8 hr, the recombinant bacteriophage were recovered by washing, for 18 hr with SMG buffer and after the addition of glycerol to 50% were frozen at −80° C.

The TSAR-12 library thus formed had a working titer of $\sim 2 \times 10^{11}$ pfu/mL.

6.3. Characterization of the TSAR-9 and -12 Libraries

The inserted synthetic oligonucleotides for each of the TSAR libraries, described in Sections 6.1 and 6.2 above, had a potential coding complexity of $20^{36}$ ($\sim 10^{47}$) and $20^{20}$, respectively, and since $\sim 10^{14}$ molecules were used in each transformation experiment, each member of these TSAR libraries should be unique. After plate amplification the library solution or stock has $10^4$ copies of each member/mL.

It was observed that very few (<10%) of the inserted oligonucleotide sequences characterized so far in both of the libraries have exhibited deletions or insertions. This is likely a reflection of the accuracy assembling the oligonucleotides under the conditions used and the fact that certain types of mutations (i.e., frame-shifts) would not be tolerated as pIII an essential protein for phage propagation.

In order to determine whether any coding bias existed in the variant non-predicted peptides expressed by these libraries, perhaps due to biases imposed in vitro during synthesis of the oligonucleotides or in vivo during expression by the reproducing phage, inserts were sequenced as set forth below.

6.3.1. Characterization of TSAR-9 Library

Inserted synthetic oligonucleotide fragments of 23 randomly chosen isolates were examined from the TSAR-9 library. Individual plaques were used to inoculate 1 ml of 2XYT broth containing E. coli (DH5αF') cells and the cultures were allowed to grow overnight at 37° C. with aeration. DNA was isolated from the culture supernatants according to Maniatis, supra. Twenty-three individual isolates were sequenced according to the method of Sanger (Proc. Natl. Acad. Sci. USA (1979) 74:5463–5467) using as a primer the oligonucleotide 5'-AGCGTAACGATCTCCCG (SEQ ID NO. 99), which is 89 nucleotides downstream of the pIII gene cloning site of the m663 vector used to express the TSARS.

Nucleotide sequences and their encoded amino acid sequences were analyzed with the MACVECTOR™ computer program (IBI, New Haven, Conn.). The Microsoft EXCEL program was used to evaluate amino acid frequencies. Such analyses showed that the nucleotide codons coding for and hence most amino acids, occurred at the expected frequency in the TSAR-9 library of expressed proteins. The notable exceptions were glutamine and tryptophan, which were over- and under-represented, respectively.

It is of interest to note the paucity of TAG stop codons in the inserts, i.e., only 2 of ~200 isolates characterized contained a TAG stop codon. About half $[1-(47/48)^{36}]$ of the phage inserts were expected to have at least one TAG codon in view of the assembly scheme used. However, most of the TAG-bearing phage appear to have been lost from the library, even though the bacterial host was supE. This may be a consequence of suppression being less than 100% effective.

The amino acids encoded by the inserted double stranded synthesized oligonucleotide sequences, excluding the fixed PG-encoding centers, were concatenated into a single sequence and the usage frequency determined for each amino acid using the Microsoft EXCEL™ program. These frequencies were compared to that expected from the assembly scheme of the oligonucleotides, and the divergence from expected values represented by the size of the bars above and below the baseline. Chi square analysis was used to determine the significance of the deviations. The majority of amino acids were found to occur at the expected frequency, with the notable exceptions that glutamine and tryptophan were somewhat over- and under-represented, respectively. Thus, except for the invariant Pro-Gly, any position could have any amino acid; hence, the sequences are unpredicted or random.

6.3.2. Characterization of TSAR-12 Library

Approximately 10 randomly chosen inserted oligonucleotides from the TSAR-12 library were examined by DNA sequencing as described above in Section 6.3.1. The isolates were chosen at random from the TSAR-12 library and prepared for sequencing, as were the TSAR-9 isolates. Analysis showed that except for the invariant Gly any position could have any amino acid; hence, the sequences are unpredicted or random.

6.4. Preparation of R8C Library

Referring now to FIG. 3, two oligonucleotides were synthesized on an Applied Biosystems Model 380a machine with the sequence 5'-TGACGTCTCGAGTTGTNNKNN-KNNKNNKNNKNNKNNKTGTGGAT CTAGAAGG-ATC-3'(SEQ ID NO:31) and 5'-GATCCTTCTAGATCC-3' (SEQ ID NO:32), where N is an equimolar ratio of deoxy-nucleotides A, C, G, and T, and K is an equimolar ratio of G and T. Fifty pmol of each oligonucleotide was incubated at 42° C. for 5 min, then 37° C. for 15 min, in 50 μL of SEQUENASE™ buffer (U.S. Biochemicals, Cleveland, Ohio) with 0.1 μg/μL acetylated BSA, and 10 mM DTT. After annealing, 10 units of SEQUENASETM DNA polymerase (U.S. Biochemicals) and 0.2 mM of each dNTP were added and incubated at 37 ° C. for 15 min. The sample was then heated at 65° C. for 2 hr, digested with 100 units of both Xho I and Xba I (New England BioLabs, Beverly, Mass.), phenol extracted, ethanol precipitated, and resolved on a 15% non-denaturing polyacrylamide gel. The assembled, digested fragment was gel purified prior to ligation. The vector, m663 (Fowlkes, D. et al. Biotech. (1992) 13:422∝427), was prepared by digestion with Xho I and Xba I, calf alkaline phosphatase (Boebringer Mannheim, Indianapolis, Tenn.) treatment, phenol extracted, and purified by agarose gel electrophoresis. To ligate, 20 μg vector was combined with 0.2 μg insert in 3 mL with T4 DNA ligase (Boebringer Mannheim), according to the manufacturer. After removal of the protein and buffer by phenol extraction and ethanol precipitation, the ligated DNA was electroporated into XL1-Blue E. coli (Stratagene, San Diego, Calif.) and plated for eight hours at 37° C. To recover the recombinant phage, the top agar was collected with a spatula, mixed with an equal volume of 100 mM NaCl, 10 mM $MgCl_2$, and 50 mM Tris-HCl (pH 7.5), and disrupted by two passes through an 18-gauge syringe needle. The bacterial cells were removed by centrifugation, and phage particles were collected by polyethylene glycol precipitation and stored at −70° C. in 25% glycerol. The library had $10_8$ total recombinants and a working titer of $6 \times 10^{13}$ pfu/mL.

Members of the library were checked for inserts by the polymerase chain reaction (Saiki, et al. Science (1988)

239:487–491). Individual plaques on a petri plate were touched with a sterile toothpick and the tip was stirred into 2 xYT with F+ E. coli bacteria and incubated overnight at 37° C. with aeration. Five microliters of the phage supernatant were then transferred to new tubes containing buffer (67 mM Tris-HCl, pH 8.8/10 mM β-mercaptoethanol/16.6 mM ammonium sulfate/6.7 mM EDTA/50 μg bovine serum albumin per mL), 0.1 mM deoxynucleotide triphosphates, and 1.25 units of TAQ™ DNA polymerase (Boehringer Mannheim, Indianapolis, Ind.) with 100 pmoles of oligonucleotide primers. The primers flanked the cloning site in gene III of m663 (5'-TTCACCTCGAAAGCAAGCTG-3' (SEQ ID NO:100) and 5'-CCTCATAGTTAGCGTAACG-3' (SEQ ID NO:101)). The assembly reactions were incubated at 94° C. for 1 min, 56° C. for 2 min, and 72° C. for 3 min; this cycle was repeated 24 times. The reaction products were then resolved by electrophoresis on a NUSIEVE™ 2.0% agarose gel (FMC, Rockland, Me.). Gels revealed that for 20 plaques tested, all were recombinant and had single inserts of the expected size.

Based on the sample size of the library, it was anticipated that 100% of the recombinants had single inserts. However, all of the SH3-binding phage isolated from the R8C library had double-inserts. Such phage are presumed rare (i.e., <5%) within the library, yet because the SH3-binding peptide appears to need to be linear they were selected for by our screening methods. Most likely they were formed during the generation of the library; one scenario is that the inserts ligated together to form head-to-head dimers and that they were subsequently cloned into m663 DNA by ligation with the vector's Xho I sticky end and by illegitimate ligation with the vector's Xba I site (see, FIG. 4).

6.5. Preparation of Target-coated Microtiter Wells 6.5.1. Preparation of GST-SH3 Fusion Proteins The preparation of Src-GST fusion protein was first described by Smith and Johnson, in Gene (1988) 67:31, the disclosure of which is incorporated by reference herein. Briefly, pGEX-derived (Pharmacia, Piscataway, N.J.) constructs expressing GST fusion proteins containing the SH3 domains of Src, Grb2, Crk, Abl, or PLCγ were obtained from Dr. Channing Der (University of North Carolina at Chapel Hill); a construct expressing the SH3 domain of Yes was obtained from Dr. Marius Sudol (Rockefeller University). The use of the pGEX bacterial expression vector for the production of GST-SH3 fusion proteins is well-known to those in the art. See, e.g., Cicchetti, P. et al., in Science (1992) 257:803–806. Briefly, the coding region for a particular SH3 domain can be fused in-frame at the Bam HI site of pGEX-2T. Thus, fusion proteins were prepared as per the manufacturer's instructions, and quantified by Coomassie Blue staining of SDS-polyacrylamide gels. Microtiter wells were coated with 5–20 μg GST-SH3 fusion protein in 100 mM NaHCO$_3$, pH 8.5, blocked with 100 mM NaHCO$_3$ (pH 8.5) 1% BSA, and washed. All washes consisted of five applications of 1XPBS, 0.1% TWEEN™ 20 surfactant, 0.1% BSA (Buffer A). Where appropriate, the amount of protein bound to each well was quantified with an anti-GST antibody-based ELISA (Pharmacia, Piscataway, N.J.), and with a GST-binding phage, isolated during the course of this work.

6.5.2. Coating of Microtiter Wells

Bacterially expressed Src SH3 glutathione-S-transferase (Src-GST) fusion protein was purified from bacterial lysates using glutathione agarose 4B (Pharmacia), according to the manufacturer's instructions. Bound Src-GST fusion protein was eluted from the glutathione agarose with 10 mM glutathione in PBS. Microtiter wells were then coated with Src-GST fusion protein (1–10 μg/well, in 50 mM NaHCO$_3$, pH 8.5) overnight at 4° C. To block non-specific binding of phage, 100 μL 1% BSA in 100 mM NaHCO$_3$, pH 8.5, was added to each well and allowed to incubate at room temperature for 1 hour. The wells were then washed five times with 200 μL PBS, 0.1% TWEEN™ 20 surfactant, 0.1% BSA (Buffer A).

6.6. Biopanning and Subsequent Characterization Of Phage-displayed Random Peptide Libraries with Src-GST Fusion Protein as Target Molecule 6.6.1. Isolation of Src SH3-Binding Phage Library screens were performed as previously described. Kay, B. K., et al., in Gene (1993) 128:59–65. Briefly, 1×10$^{11}$ pfu TSAR 9, TSAR 12, or R8C phage in Buffer A were incubated in a Src SH3-GST-coated well for 2 hours. The wells were washed, and bound phage were eluted with 100 μL 50 mM glycine.HCl (pH 2.2), transferred to a new well, and neutralized with 100 mL 200 mM NaHPO$_4$ (pH 7.0). Recovered phage were used to infect 1×10$^9$ DH5αF' E. coli cells in 20 mL 2xYT; the infected cells were grown overnight, resulting in a 1000- to 10,000-fold amplification of phage titer. Amplified phage were panned twice more, as above, excepting the amplification step. Binding phage recovered after the third round of panning were plated at a low density on a lawn of DH5αF' E. coli cells to yield isolated plaques for clonal analysis. Isolated plaques were used to produce small cultures from which phage stocks and DNA were recovered for phage binding experiments and dideoxy sequencing (Sanger, F., et al., in Proc. Natl. Acad. Sci. USA (1977) 74:5463–5467), respectively. Clones were confirmed as binding the SH3 domain by applying equal titers of phage to wells containing Src SH3-GST or GST alone, and titering the number of eluted particles from each well, or detecting bound phage with an anti-phage antibody-based ELISA (Pharmacia).

Indeed, the ability of isolated phage clones to bind to several SH3 domains derived from a variety of different proteins can be investigated by the manner described above. GST-SH3 fusion proteins containing SH3 domains from a variety of different proteins are bound to microliter wells. An aliquot of the aforementioned phage stocks (50 μL) is introduced into wells containing the different GST-SH3 fusion proteins. After room temperature incubation for 1–2 hours, the liquid contents of the microtiter plates are removed, and the wells are washed 5 times with 200 μL Buffer A. Bound phage are eluted with 100 μL 50 mM glycine (pH 2.2), transferred to a new well, and neutralized with 100 μL 200 mM NaHPO$_4$ (pH 7.0). The phage are diluted 10$^{-3}$- to 10-6-fold, and aliquots are plated onto lawns of DH5αF' E. coli cells to establish the number of plaque forming units in the output sample. From these experiments, the relative specificity of different Src SH3 binding clones for SH3 domains derived from other proteins is determined.

6.6.2. Phage ELISA and Nucleotide Sequencing

To evaluate the binding of isolates to various target proteins, enzyme-linked-immuno-assays (ELISA) were also performed. Bacterial cultures were infected with phage isolates and cultured overnight in 2XYT at 37° C. The cells were spun down and 25 mL of supernatant was added to microtiter plate wells coated with 50 μL of protein (1 mg/mL in 100 mM NaHCO$_3$, pH 8.4; overnight at 4° C. or for a few hours at room temperature) and blocked (1 mg/mL BSA in 100 mM NaHCO$_3$, pH 8.4; for about one hour). The phage are incubated in the well with 25 μl of PBS-0.1% TWEEN™

20 surfactant at RT for 2 hr. The wells are then washed multiple times over 30 minutes. To each well is added 50 μL of polyclonal anti-phage antibody conjugated to horseradish peroxidase. The antibody is diluted 1:3000 in BSA-PBS-TWEEN™ 20 surfactant; it was obtained from Pharmacia (Piscataway, N.J.; catalog number 27-9402-01). After 30 minutes, the wells are washed again with BSA-PBS-TWEEN™ 20 surfactant for ~20 minutes. Finally, 100 μL of ABTS reagent (Pharmacia, with $H_2O_2$) are added to each well for the development of color. Plates are read with a plate reader (Molecular Devices, Menlo Park, Calif.) at 405 nm wavelength.

The nucleotide sequence of the relevant segments of the Src SH3 binding clones (or phage clones that bind to SH3 domains of other proteins) were sequenced using standard methods. Sanger, F., et al., in Proc. Natl. Acad. Sci. USA (1977) 74:5463–5467. The oligo primer 5'-AGCGTAACGATCTAAA-3'(SEQ ID NO:102) was used, which is 89 nucleotides downstream of the gene III cloning site of M13 m666. The nucleotide sequences were analyzed with the MAC VECTOR™ computer program (IBI, New Haven, Conn., USA). From this nucleotide sequence information the primary sequence of each Src SH3 binding peptide was deduced. The corresponding synthetic peptides were then prepared by techniques well known in the art with or without flanking sequences. Indeed, these synthetic peptides have been shown to bind to SH3 domain targets, with those possessing the phage flanking amino acid residues exhibiting greater binding affinity.

6.7 In Vitro Peptide Binding Assays

Peptides were obtained from Research Genetics (Birmingham, Ala.), Chiron Mimotopes (Victoria, Australia), or synthesized by conventional techniques by Dr. J. Mark Carter of Cytogen Corporation (Princeton, N.J.). Peptide purity was assessed by HPLC and/or mass spectrometry. Biotinylated peptides were synthesized with either a KSGSG (SEQ ID NO:103) or a GSGS (SEQ ID NO:104) peptide linker (a spacer) between the biotin and the N-terminus of the peptide. Binding experiments were performed as above, excepting the use of 10 μM peptide instead of phage. Bound biotinylated peptide was detected with streptavidin conjugated to alkaline phosphatase (Sigma Chemical Co., St. Louis, Mo.). After one hour incubation period at room temperature, the wells were washed, and a solution of 3 mM p-nitrophenyl-phosphate (US Biochemicals, Cleveland, Ohio) in 50 mM $NaCO_3$ (pH 9.8), and 50 mM $MgCl_2$ was added and color allowed to develop. Signals were read with an ELISA plate reader (Molecular Devices, Menlo Park, Calif.) at 405 nm wavelength. Binding experiments were performed in triplicate. The results are presented in FIGS. 7 and 8.

6.8. Peptide Competition of GST-SH3 Affinity Precipitations of Cell Lysates

Labeled proteins are prepared by incubating a culture of HeLa cells overnight with ≧100 μCi/mL $^{35}$S-methionine. The cells are then washed and lysed with mild detergent. This mixture of radioactive proteins is incubated with Src-GST fusion protein that has been immobilized on glutathione-linked SEPHAROSE™ agarose beads (Pharmacia, Piscataway, N.J.). After several hours of tumbling, the beads are pelleted gently by low-speed centrifugation, and the supernatant is discarded. The beads are then resuspended into a slurry in PBS-0.1% TWEEN™ 20 surfactant, pelleted, and washed several additional times. Finally, a 2% SDS solution is added to the sample, which is then boiled at 100° C. for 3 minutes. Afterward, the sample is centrifuged, and the supernatant loaded on a 10% polyacrylamide SDS gel for electrophoresis. After the proteins have been resolved, the gel is fixed, dried down, and exposed to X-ray film for autoradiography or phosphor plates for scanning by a Molecular Dynamics PHOSPHORIMAGER™.

The ability of Src SH3 to bind certain $^{35}$S-labeled proteins is examined for competability with exogenous peptides. Synthetic peptides corresponding to phage-displayed inserts and motifs are added at the time that the lysate is incubated with the Src-GST fusion protein immobilized on glutathione-linked sepharose beads. The SH3 binding peptides block binding of all or some of the labeled proteins while negative control peptides (unrelated peptide sequences) do not. The amount of competition is quantified and correlated with the amount of added SH3-domain binding peptides.

Alternatively, NIH 3T3 cells were grown in Dulbecco's Modified Eagle Medium (DME) +10% fetal calf serum (FCS) +80 μCi/mL Tran$^{35}$Slabel (ICN), washed with PBS, lysed in RIPA buffer, and pelleted. Supernatant from 1.5×10$^6$ cells was precleared with 100 μg glutathione-agarose-immobilized GST. The supernatant was then incubated with 10 μg glutathione-agarose-immobilized GST-SH3 fusion protein with or without added test peptide in a final volume of 250 μL. Pelleted beads were washed with 1 mL each of RIPA, RIPA +1% deoxycholate+0.1% SDS, and PBS, resuspended in 50 μL SDS-PAGE sample buffer, boiled, and subjected to SDS-PAGE (7.5%). Labeled proteins were detected by phosphorimaging (Molecular Dynamics). The results are presented in FIG. 9.

6.9. Peptide Competition of GST-SH3 Affinity Precipitations of PI-3' Kinase from Cell Lysates It is possible to follow the precipitation of PI-3' Kinase by Src from cell lysates in the presence or absence of SH3-binding peptides. HeLa cells are lysed with detergent and the protein mixtures are incubated for several hours with the Src-GST fusion protein immobilized on glutathione-linked Sepharose beads. After several hours of tumbling, the beads are pelleted gently by low-speed centrifugation and the supernatant is discarded. The beads are then resuspended into a slurry in PBS-0.1% Tween 20, pelleted, and washed several additional times. Finally, an SDS solution is added to the sample, which is then boiled at 100° C. for 3 minutes. Subsequently, the sample is centrifuged, and the supernatant is loaded on a 10% polyacrylamide SDS gel for electrophoresis. After the proteins have been resolved, the gel is blotted to nitrocellulose or nylon (i.e., western blot). The filter is then probed with a PI-3' Kinase antibody (monoclonal and polyclonal antibodies are available from Upstate Biotechnology Incorporated, Lake Placid, N.Y.) and an enzyme-linked secondary antibody. The amount of PI-3' Kinase is then quantitated.

The ability of Src SH3 to bind PI-3' Kinase is examined for competability with exogenous peptides. Synthetic peptides corresponding to phage-displayed inserts and motifs are added at the time that the lysate is incubated with the Src-GST fusion protein that has been immobilized on glutathione-linked sepharose beads. Ten-fold and one hundred-fold molar excess of peptides are used relative to SH3 proteins. The SH3 binding peptides block binding of the PI-3' Kinase as detected on western blots while negative control peptides (unrelated peptide sequences) do not. The amount of competition is quantified and correlated with the amount of added SH3-domain binding peptides.

6.10. In Vivo Association of SH3-Binding Peptides With SH3-Domains of Proteins To demonstrate association of the SH3-binding peptides with SH3-domains of proteins inside cells, the SH3-binding peptides are tagged and localized in cells. For example, Bar-Sagi et al., in *Cell* (1993) 74:83–91, have shown that SH3-binding proteins localize to the cytoskeleton when expressed in cells. Thus, the SH3 domain-binding peptides of the present invention can serve as cellular targetting signals (e.g., to the cytoskeleton). Accordingly, the peptides are tagged with biotin and, subsequently, injected into cells. Alternatively, one can transfect into cells a recombinant plasmid that expresses a fusion protein comprising of the SH3-binding peptide and the green fluorescent protein (GFP, Chalfie et al., in *Science* (1994) 263:802–805). The location of the biotinylated peptide or the GFP fusion protein is then assayed with FITC-labeled streptavidin in paraformaldehyde-fixed cells or by direct fluorescence in living cells, respectively. Localization of the SH3-binding peptides to the cytoskeleton demonstrates that the SH3-binding peptides can bind SH3-domain proteins in vivo. In addition, focal adhesions, which are rich in Src, are also sites of potential subcellular localization of SH3-binding peptides.

Thus, NIH 3T3 fibroblasts were cultured in vitro on glass coverslips coated with fibronectin. After two days of growth at 37° C., the cells were fixed for one hour at room temperature in the presence of 2% paraformaldehyde (pH 7.5). The coverslips were washed with PBS-0.1% Tween 20 several times to remove the fixative. Next, the coverslips were dipped into acetone (chilled at −20° C.) for approximately 20 seconds and allowed to air-dry. The coverslips were washed again with PBS-0.1% Tween 20, containing BSA (1 mg/mL), and incubated for 2 hours at room temperature with different biotinylated peptides in PBS-0.1% Tween 20. The coverslips were washed and then incubated with 1 mg/mL streptavidin-Cy3 (Jackson Immunoresearch Co., West Grove, Pa.) for 1 hour at room temperature. Finally, the coverslips were washed in PBS-0.1% Tween 20, mounted in a glycerol solution on a glass slide, and viewed with a Nikon Optiphot epifluorescence microscope and a 60× oil immersion lens.

The results are presented in FIG. 11, in which panel A displays cells stained with the conjugate biotin-spacer-VLKRPLPIPPVTR (SEQ ID NO:64); panel B exhibits cells stained with the conjugate, biotin-spacer-GILAPPVPPRNTR (SEQ ID NO:63); panel C shows cells stained with the long consensus peptide, biotin-spacer-RSTPRPLPPLPTTR (SEQ ID NO:67); and panel D shows cells stained with the proline-rich vinculin peptide conjugate, biotin-spacer-LAPPKPPLPEGEV (SEQ ID NO:70). The "spacer" sequence is KSGSG (SEQ ID NO:103). As shown in FIG. 11, the panels in which SH3 domain-binding peptides were used present a bright display of fluorescence activity that is in sharp contrast to the relatively "dark" features of panel D (non-SH3 domain binding vinculin segment). These results demonstrate further the ability of the SH3 domain-binding peptides of the present invention to localize to protein targets (e.g., Src and Src-related proteins) within cells and provide an image thereof.

6.11. In Vivo Modulation of Src In Oocytes with SH3-Binding Peptides

When *Xenopus laevis* oocytes are injected with mRNA encoding deregulated Src, there are dramatic cytological and biochemical changes in the oocyte (Unger, T. F. and Steele, R. E., in *Mol. Cell. Biol.* (1992) 12:5485–5498). The applicants have obtained the plasmid for generating Src mRNA, which is available from Dr. Robert Steele (University of California at Irvine). Synthetic SH3-binding peptides are injected into oocytes that have been previously injected with Src mRNA. The state of the cytoskeleton is inspected visually by observing the arrangement of cortical pigment granules under a dissecting microscope. The state of phosphorylation of several proteins is examined by western blotting with an anti-phosphotryosine monoclonal antibody (4G10; Upstate Biotechnology Incorporated), as described in Unger and Steele, above.

6.12. Progesterone-induced *X. laevis* Oocyte Maturation

Segments of adult ovary were removed surgically and incubated in 0.1% collagenase type D (Boehringer Mannheim, Indianapolis, Ind.) in $Ca^{2+}$-free OR2 (82.5 mM NaCl, 2.5 mM KCl, 1.0 mM $MgCl_2$, 1.0 mM $Na_2HPO_4$, 5.0 mM HEPES, and 3.8 mM NaOH, pH 7.6). Oocytes were then washed 3–5 times with OR2 containing 1.0 mM $CaCl_2$ and allowed to recover in OR2 overnight at 18° C. Stage VI oocytes were injected with 40 nL of 100 mM peptide or water. After injection, the oocytes were placed in OR2 with 2 mg/mL progesterone (Sigma, St Louis, Mo.) and incubated at 20° C. oocytes were scored at hourly time points for germinal vesicle breakdown (GVBD).

FIG. 10 presents the results of this experiment. As shown by the graph, oocytes injected with the SH3 domain-binding peptide VLKRPLPIPPVTR (SEQ ID NO:64) exhibit a faster rate of progesterone-induced germinal vesicle breakdown relative to oocytes that had been injected with water or with the proline-rich vinculin peptide, LAPPKPPLPEGEV (SEQ ID NO:70). These results parallel those obtained by Unger and Steele, supra, who observed a gross alteration in the cortex of oocytes that had been injected with RNA encoding a deregulated Src variant ("active" Src) versus those injected with RNA encoding the wild-type Src ("cellular" Src). Also, as shown in FIG. 3B of the Unger and Steele article, oocytes injected with deregulated or active Src RNA matured at a faster rate than oocytes injected with water or wild-type Src RNA.

The present results obtained with Src SH3 domain-binding peptides suggest that these peptides modulate the biochemical activity of "cellular" Src; in particular, it is proposed that at least some of the Src SH3 domain-binding peptides of the present invention upregulate the biochemical activity of "cellular" Src, which may be downregulated or inhibited in its normal state. Hence, the administration of the SH3 domain-binding peptides of the present invention can constitute a novel method of modulating the activity of Src or Src-related proteins. Specifically, certain of these peptides are able to activate Src-family proteins.

6.13. In Vivo Antagonism of Src In Src Transformed Cells with SH3-binding Peptides The coding regions for SH3-binding peptides are cloned into vectors that direct their expression in animal cells. A bipartite gene is constructed, encoding a protein with c-myc epitope and SH3-binding peptide, which is transcribed from a strong constitutive promoter (e.g., SV40, CMV, HSV TK, calmodulin). The vector is introduced into either normal or Src-transformed cells via transfection (e.g., electroporation, calcium phosphate, liposomes, DEAE dextran). Transfected cells express the bipartite gene transiently in culture. To create stable transformed cell lines, the vector carries a selectable marker (e.g., neomycin resistance) or transfection is performed in the presence of excess plasmid carrying a selectable marker (e.g., neomycin resistance) and cells selected for the marker. Transfected cells are stained by immunofluorescence to detect expression of the bipartite protein. The hybridoma 9E10 secretes a monoclonal antibody that is highly specific for the c-myc epitope (EQKLISEEDLN [SEQ ID NO:105]; see, Evan, G. A. et al., in *Mol. Cell. Biol.* (1985) 5:3610–3616). This antibody is used in immunofluorescence experiments to demonstrate that the bipartite protein is expressed inside the cells, and in some cases, localized to subcellular structures enriched in SH3 domain bearing proteins.

There are several controls used in these experiments. First, cells are transfected with vectors that do not have the SH3-binding peptide coding region. Second, normal (non-transformed) cells are transfected. Third, cells transformed by oncogenes other than Src are used in the transfection experiments. Fourth, cells are stained with other monoclonal antibodies that do not recognize the c-myc epitope.

Transfected cells are examined for any changes in cell shape, behavior, and metabolism as a consequence of expressing the SH3 binding peptides. Cell shape is examined by phase contrast microscope at several times after transfection; in particular, the flatness of the cells, their adhesion to the substrate, and the degree of cell ruffling are monitored. Cell division rates, cell migration, and contact inhibition are also observed over time. Finally, the amount of phosphorylated tyrosine in transfected cells is quantitated by phosphoaminoacid analysis and with an anti-phosphotryosine monoclonal antibody (4G10; Upstate Biotechnology Incorporated) in western blotting experiments.

It should be apparent to one of ordinary skill that many other embodiments of the present invention can be contemplated beyond the preferred embodiments described above but which other embodiments nevertheless fall within the scope and spirit of the present invention. Hence, the present invention should not be construed to be limited to the preferred embodiments described herein, which serve only to illustrate the present invention, but only by the claims that follow.

Also, numerous references are cited throughout the specification. The complete disclosures of these references are incorporated by reference herein.

What is claimed is:
1. An SH3-binding peptide of up to 45 amino acid residues in length consisting essentially of an amino acid sequence selected from the group consisting of: SEQ TD NOs: 38–61 and SEQ ID NO: 106.

* * * * *

```
                          SEQUENCE LISTING (1) GENERAL INFORMATION:

(iii) NUMBER OF SEQUENCES: 106

(2) INFORMATION FOR SEQ ID NO: 1:

(i) SEQUENCE CHARACTERISTICS:
         (A) LENGTH: 10 amino acids
         (B) TYPE: amino acid
         (D) TOPOLOGY: unknown (ii) MOLECULE TYPE: peptide (ix) FEATURE:
         (A) NAME/KEY: Modified-site
         (B) LOCATION: 8
         (D) OTHER INFORMATION: /note= "X = a hydrophobic amino acid
             residue, such as Pro or Leu"

(xi) SEQUENCE DESCRIPTION: SEQ ID NO: 1:

Xaa Pro Xaa Xaa Pro Pro Pro Xaa Xaa Pro
1               5                   10

(2) INFORMATION FOR SEQ ID NO: 2:

(i) SEQUENCE CHARACTERISTICS:
         (A) LENGTH: 9 amino acids
         (B) TYPE: amino acid
         (D) TOPOLOGY: unknown (ii) MOLECULE TYPE: peptide (ix) FEATURE:
         (A) NAME/KEY: Modified-site
         (B) LOCATION: 1..3
         (D) OTHER INFORMATION: /note= "X = any amino
             acid residue other than Cys"

(ix) FEATURE:
         (A) NAME/KEY: Modified-site
         (B) LOCATION: 6
         (D) OTHER INFORMATION: /note= "X = any amino
             acid residue other than Cys"

(ix) FEATURE:
```

(A) NAME/KEY: Modified-site
        (B) LOCATION: 8..9
        (D) OTHER INFORMATION: /note= "X = any amino
            acid residue other than Cys"

(xi) SEQUENCE DESCRIPTION: SEQ ID NO: 2:

Xaa Xaa Xaa Pro Pro Xaa Pro Xaa Xaa
1               5

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /note= "X tends to be a
            basic amino acid residue (like Arg, Lys or
            His)"

(ix) FEATURE:
        (A) NAME/KEY: Modified-site
        (B) LOCATION: 8..9
        (D) OTHER INFORMATION: /note= "X tends to be a
            basic amino acid residue (like Arg, Lys and
            His)"

(xi) SEQUENCE DESCRIPTION: SEQ ID NO: 3:

Arg Xaa Leu Pro Pro Arg Pro Xaa Xaa
1               5

(2) INFORMATION FOR SEQ ID NO: 4:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 4:

Arg Lys Leu Pro Pro Arg Pro Arg Arg
1               5

(2) INFORMATION FOR SEQ ID NO: 5:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO: 5:

Val Pro Pro Pro Val Pro Pro Arg Arg Arg
1               5                   10

(2) INFORMATION FOR SEQ ID NO: 6:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide

```
      (ix) FEATURE:
           (A) NAME/KEY: Modified-site
           (B) LOCATION: 2
           (D) OTHER INFORMATION: /note= "X tends to be
               Pro"

(ix) FEATURE:
           (A) NAME/KEY: Modified-site
           (B) LOCATION: 3
           (D) OTHER INFORMATION: /note= "X = a hydrophobic
               amino acid residue"

(ix) FEATURE:
           (A) NAME/KEY: Modified-site
           (B) LOCATION: 5
           (D) OTHER INFORMATION: /note= "X tends to be
               Pro"

(xi) SEQUENCE DESCRIPTION: SEQ ID NO: 6:

Xaa Xaa Xaa Pro Xaa Xaa Pro
1               5

(2) INFORMATION FOR SEQ ID NO: 7:

(i) SEQUENCE CHARACTERISTICS:
           (A) LENGTH: 9 amino acids
           (B) TYPE: amino acid
           (D) TOPOLOGY: unknown (ii) MOLECULE TYPE: peptide (ix) FEATURE:
           (A) NAME/KEY: Modified-site
           (B) LOCATION: 2
           (D) OTHER INFORMATION: /note= "X= any amino acid
               residue other than Cys"

(ix) FEATURE:
           (A) NAME/KEY: Modified-site
           (B) LOCATION: 8..9
           (D) OTHER INFORMATION: /note= "X = any amino
               acid residue other than Cys"

(xi) SEQUENCE DESCRIPTION: SEQ ID NO: 7:

Arg Xaa Leu Pro Pro Arg Pro Xaa Xaa
1               5

(2) INFORMATION FOR SEQ ID NO: 8:

(i) SEQUENCE CHARACTERISTICS:
           (A) LENGTH: 9 amino acids
           (B) TYPE: amino acid
           (D) TOPOLOGY: unknown (ii) MOLECULE TYPE: peptide (ix) FEATURE:
           (A) NAME/KEY: Modified-site
           (B) LOCATION: 9
           (D) OTHER INFORMATION: /note= "X = any
               hydrophobic amino acid residue"

(xi) SEQUENCE DESCRIPTION: SEQ ID NO: 8:

Arg Xaa Leu Pro Pro Leu Pro Arg Xaa
1               5

(2) INFORMATION FOR SEQ ID NO: 9:

(i) SEQUENCE CHARACTERISTICS:
           (A) LENGTH: 7 amino acids
           (B) TYPE: amino acid
           (D) TOPOLOGY: unknown
```

(ii) MOLECULE TYPE: peptide (xi) SEQUENCE DESCRIPTION: SEQ ID NO: 9:

Arg Pro Leu Pro Pro Leu Pro
1               5

(2) INFORMATION FOR SEQ ID NO: 10:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /note= "X = any amino
            acid residue except Cys"

(ix) FEATURE:
        (A) NAME/KEY: Modified-site
        (B) LOCATION: 5..6
        (D) OTHER INFORMATION: /note= "X = any
            hydrophobic amino acid residue"

(ix) FEATURE:
        (A) NAME/KEY: Modified-site
        (B) LOCATION: 8
        (D) OTHER INFORMATION: /note= "X = any amino
            acid residue except Cys"

(ix) FEATURE:
        (A) NAME/KEY: Modified-site
        (B) LOCATION: 9
        (D) OTHER INFORMATION: /note= "X = any
            hydrophilic amino acid residue except Cys"

(xi) SEQUENCE DESCRIPTION: SEQ ID NO: 10:

Arg Xaa Leu Pro Xaa Xaa Pro Xaa Xaa
1               5

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 11:

Arg Pro Leu Pro Pro Leu Pro Thr Ser
1               5

(2) INFORMATION FOR SEQ ID NO: 12:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (v) FRAGMENT TYPE: C-terminal (ix) FEATURE:
        (A) NAME/KEY: Modified-site
        (B) LOCATION: 1..4
        (D) OTHER INFORMATION: /note= "X = any amino
            acid residue except Cys"

```
           (xi) SEQUENCE DESCRIPTION: SEQ ID NO: 12:

Xaa Xaa Xaa Xaa
1

(2) INFORMATION FOR SEQ ID NO: 13:

(i) SEQUENCE CHARACTERISTICS:
               (A) LENGTH: 5 amino acids
               (B) TYPE: amino acid
               (D) TOPOLOGY: unknown (ii) MOLECULE TYPE: peptide (v) FRAGMENT TYPE: C-terminal (ix) FEATURE:
               (A) NAME/KEY: Modified-site
               (B) LOCATION: 1..5
               (D) OTHER INFORMATION: /note= "X = any amino
                   acid residue except Cys"

(xi) SEQUENCE DESCRIPTION: SEQ ID NO: 13:

Xaa Xaa Xaa Xaa Xaa
1               5

(2) INFORMATION FOR SEQ ID NO: 14:

(i) SEQUENCE CHARACTERISTICS:
               (A) LENGTH: 4 amino acids
               (B) TYPE: amino acid
               (D) TOPOLOGY: unknown (ii) MOLECULE TYPE: peptide (v) FRAGMENT TYPE: N-terminal (ix) FEATURE:
               (A) NAME/KEY: Modified-site
               (B) LOCATION: 1..4
               (D) OTHER INFORMATION: /note= "X = any amino
                   acid residue except Cys"

(xi) SEQUENCE DESCRIPTION: SEQ ID NO: 14:

Xaa Xaa Xaa Xaa
1

(2) INFORMATION FOR SEQ ID NO: 15:

(i) SEQUENCE CHARACTERISTICS:
               (A) LENGTH: 13 amino acids
               (B) TYPE: amino acid
               (D) TOPOLOGY: unknown (ii) MOLECULE TYPE: peptide (ix) FEATURE:
               (A) NAME/KEY: Modified-site
               (B) LOCATION: 1..3
               (D) OTHER INFORMATION: /note= "X = any amino
                   acid residue except Cys"

(ix) FEATURE:
               (A) NAME/KEY: Modified-site
               (B) LOCATION: 5
               (D) OTHER INFORMATION: /note= "X = any amino
                   acid residue except Cys"

(ix) FEATURE:
               (A) NAME/KEY: Modified-site
               (B) LOCATION: 8..9
               (D) OTHER INFORMATION: /note= "X = any
                   hydrophobic amino acid residue"
```

```
        (ix) FEATURE:
             (A) NAME/KEY: Modified-site
             (B) LOCATION: 11
             (D) OTHER INFORMATION: /note= "X = any amino
                 acid residue except Cys"

(ix) FEATURE:
             (A) NAME/KEY: Modified-site
             (B) LOCATION: 12
             (D) OTHER INFORMATION: /note= "X = any
                 hydrophilic amino acid residue except Cys"

(ix) FEATURE:
             (A) NAME/KEY: Modified-site
             (B) LOCATION: 13
             (D) OTHER INFORMATION: /note= "X = any amino
                 acid residue except Cys"

(xi) SEQUENCE DESCRIPTION: SEQ ID NO: 15:

Xaa Xaa Xaa Arg Xaa Leu Pro Xaa Xaa Pro Xaa Xaa Xaa
 1               5                  10

(2) INFORMATION FOR SEQ ID NO: 16:

(i) SEQUENCE CHARACTERISTICS:
         (A) LENGTH: 42 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /note= "X = Arg or Ser"

(xi) SEQUENCE DESCRIPTION: SEQ ID NO: 16:

Ser Xaa Xaa Xaa Xaa Xaa Xaa Xaa Xaa Xaa Xaa Xaa Xaa Xaa Xaa
 1               5                  10                  15

Xaa Xaa Xaa Xaa Pro Gly Xaa Xaa Xaa Xaa Xaa Xaa Xaa Xaa Xaa
            20                  25                  30

Xaa Xaa Xaa Xaa Xaa Xaa Xaa Xaa Ser Arg
            35                  40

(2) INFORMATION FOR SEQ ID NO: 17:

(i) SEQUENCE CHARACTERISTICS:
         (A) LENGTH: 69 bases
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 17:

GGCTCGAGNN NBNNBNNBNN BNNBNNBNNB NNBNNBNNBN                    40

NBNNBNNBNN BNNBNNBNNB NNBCCAGGT                                69

(2) INFORMATION FOR SEQ ID NO: 18:

(i) SEQUENCE CHARACTERISTICS:
         (A) LENGTH: 68 bases
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 18:
```

```
GGTCTAGAVN NVNNVNNVNN VNNVNNVNNV NNVNNVNNVN                  40

NVNNVNNVNN VNNVNNVNNV NNACCTGG                               68
```

(2) INFORMATION FOR SEQ ID NO: 19:

(i) SEQUENCE CHARACTERISTICS:
        (A) LENGTH: 66 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

```
TCGAGNNNBN NBNNBNNBNN BNNBNNBNNB NNBNNBNNBN                  40

NBNNBNNBNN BNNBNNBNNB CCAGGT                                 66
```

(2) INFORMATION FOR SEQ ID NO: 20:

(i) SEQUENCE CHARACTERISTICS:
        (A) LENGTH: 65 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

```
CTAGAVNNVN NVNNVNNVNN VNNVNNVNNV NNVNNVNNVN                  40

NVNNVNNVNN VNNVNNVNNA CCTGG                                  65
```

(2) INFORMATION FOR SEQ ID NO: 21:

(i) SEQUENCE CHARACTERISTICS:
        (A) LENGTH: 46 amino acids
        (B) TYPE: amino acid
        (D) TOPOLOGY: linear (ii) MOLECULE TYPE: protein (v) FRAGMENT TYPE: N-terminal (ix) FEATURE:
        (A) NAME/KEY: Modified-site
        (B) LOCATION: 2
        (D) OTHER INFORMATION: /note= "X = Arg or Ser"

(xi) SEQUENCE DESCRIPTION: SEQ ID NO: 21:

```
Ser Xaa Xaa Xaa Xaa Xaa Xaa Xaa Xaa Xaa Xaa Xaa Xaa Xaa Xaa
1               5                   10                  15

Xaa Xaa Xaa Xaa Pro Gly Xaa Xaa Xaa Xaa Xaa Xaa Xaa Xaa Xaa
            20                  25                  30

Xaa Xaa Xaa Xaa Xaa Xaa Xaa Xaa Ser Arg Pro Ser Arg Thr
        35                  40                  45
```

(2) INFORMATION FOR SEQ ID NO: 22:

(i) SEQUENCE CHARACTERISTICS:
        (A) LENGTH: 49 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 5

(D) OTHER INFORMATION: /note= "X = Arg or Ser"

(xi) SEQUENCE DESCRIPTION: SEQ ID NO: 22:

Ser His Ser Ser Xaa Xaa Xaa Xaa Xaa Xaa Xaa Xaa Xaa Xaa Xaa
1               5                   10                  15

Xaa Xaa Xaa Xaa Xaa Xaa Xaa Pro Gly Xaa Xaa Xaa Xaa Xaa Xaa
                20                  25                  30

Xaa Xaa Xaa Xaa Xaa Xaa Xaa Xaa Xaa Xaa Ser Arg Pro Ser Arg
        35                  40                  45

Thr (2) INFORMATION FOR SEQ ID NO: 23:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "X = Ser or Thr"

(ix) FEATURE:
        (A) NAME/KEY: Modified-site
        (B) LOCATION: 13
        (D) OTHER INFORMATION: /note= "X = Ser, Arg,
            Gly, Cys or Trp"

(ix) FEATURE:
        (A) NAME/KEY: Modified-site
        (B) LOCATION: 15
        (D) OTHER INFORMATION: /note= "X = Val, Ala,
            Asp, Glu, or Gly"

(xi) SEQUENCE DESCRIPTION: SEQ ID NO: 23:

Ser Xaa Xaa Xaa Xaa Xaa Xaa Xaa Xaa Xaa Xaa Xaa Xaa Gly Xaa Xaa
1               5                   10                  15

Xaa Xaa Xaa Xaa Xaa Xaa Xaa Xaa Xaa Thr Arg
                20                  25

(2) INFORMATION FOR SEQ ID NO: 24:

(i) SEQUENCE CHARACTERISTICS:
        (A) LENGTH: 48 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

TTTTGTCGAC NNNBNNBNNB NNBNNBNNBN NBNNBNNBNN                        40

BNGCGGTG                                                          48

(2) INFORMATION FOR SEQ ID NO: 25:

(i) SEQUENCE CHARACTERISTICS:
        (A) LENGTH: 48 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

```
TTTTACTAGT VNNVNNVNNV NNVNNVNNVN NVNNVNNVNN                            40

VNCACCGC                                                              48
```

(2) INFORMATION FOR SEQ ID NO: 26:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

```
TCGACNNNBN NBNNBNNBNN BNNBNNBNNB NNBNNBNGCG GTG                        43
```

(2) INFORMATION FOR SEQ ID NO: 27:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

```
CTAGTVNNVN NVNNVNNVNN VNNVNNVNNV NNVNNVNCAC CGC                        43
```

(2) INFORMATION FOR SEQ ID NO: 28:

(i) SEQUENCE CHARACTERISTICS:
        (A) LENGTH: 31 amino acids
        (B) TYPE: amino acid
        (D) TOPOLOGY: linear (ii) MOLECULE TYPE: protein (v) FRAGMENT TYPE: N-terminal (ix) FEATURE:
        (A) NAME/KEY: Modified-site
        (B) LOCATION: 2
        (D) OTHER INFORMATION: /note= "X = Ser or Thr"

(ix) FEATURE:
        (A) NAME/KEY: Modified-site
        (B) LOCATION: 13
        (D) OTHER INFORMATION: /note= "X = Ser, Arg,
            Gly, Cys or Trp"

(ix) FEATURE:
        (A) NAME/KEY: Modified-site
        (B) LOCATION: 15
        (D) OTHER INFORMATION: /note= "X = Val, Ala,
            Asp, Glu or Gly"

(xi) SEQUENCE DESCRIPTION: SEQ ID NO: 28:

```
Ser Xaa Xaa Xaa Xaa Xaa Xaa Xaa Xaa Xaa Xaa Xaa Gly Xaa Xaa
1               5                   10                  15

Xaa Xaa Xaa Xaa Xaa Xaa Xaa Xaa Xaa Thr Arg Pro Ser Arg Thr
            20                  25                  30
```

(2) INFORMATION FOR SEQ ID NO: 29:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (ix) FEATURE:
            (A) NAME/KEY: Modified-site
            (B) LOCATION: 5
            (D) OTHER INFORMATION: /note= "X = Ser or Thr"

(ix) FEATURE:
            (A) NAME/KEY: Modified-site
            (B) LOCATION: 16
            (D) OTHER INFORMATION: /note= "X = Ser, Arg,
                Gly, Cys or Trp"

(ix) FEATURE:
            (A) NAME/KEY: Modified-site
            (B) LOCATION: 18
            (D) OTHER INFORMATION: /note= "X = Val, Ala,
                Asp, Glu or Gly"

(xi) SEQUENCE DESCRIPTION: SEQ ID NO: 29:

Ser His Ser Ser Xaa Xaa Xaa Xaa Xaa Xaa Xaa Xaa Xaa Xaa Xaa Xaa
1               5                   10                  15

Gly Xaa Xaa Xaa Xaa Xaa Xaa Xaa Xaa Xaa Xaa Xaa Thr Arg Pro Ser
            20                  25                  30

Arg Thr (2) INFORMATION FOR SEQ ID NO: 30:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 30:

Xaa Xaa Xaa Xaa Xaa Xaa Xaa Xaa
1               5

(2) INFORMATION FOR SEQ ID NO: 31:

(i) SEQUENCE CHARACTERISTICS:
        (A) LENGTH: 58 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

TGACGTCTCG AGTTGTNNKN NKNNKNNKNN KNNKNNKNNK                  40

TGTGGATCTA GAAGGATC                                         58

(2) INFORMATION FOR SEQ ID NO: 32:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

GATCCTTCTA GATCC                                            15

(2) INFORMATION FOR SEQ ID NO: 33:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

```
TCGAGTTGTN NKNNKNNKNN KNNKNNKNNK NNKTGTGGAT                    40
```

(2) INFORMATION FOR SEQ ID NO: 34:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

```
CTAGATCCAC AMNNMNNMNN MNNMNNMNNM NNMNNACAAC                    40
```

(2) INFORMATION FOR SEQ ID NO: 35:

(i) SEQUENCE CHARACTERISTICS:
        (A) LENGTH: 19 amino acids
        (B) TYPE: amino acid
        (D) TOPOLOGY: unknown (ii) MOLECULE TYPE: protein (v) FRAGMENT TYPE: N-terminal (xi) SEQUENCE DESCRIPTION: SEQ ID NO: 35:

```
Ser Ser Cys Xaa Xaa Xaa Xaa Xaa Xaa Xaa Xaa Cys Gly Ser Arg Pro
1               5                   10                  15
Ser Arg Thr
```

(2) INFORMATION FOR SEQ ID NO: 36:

(i) SEQUENCE CHARACTERISTICS:
        (A) LENGTH: 28 amino acids
        (B) TYPE: amino acid
        (D) TOPOLOGY: unknown (ii) MOLECULE TYPE: protein (v) FRAGMENT TYPE: N-terminal (xi) SEQUENCE DESCRIPTION: SEQ ID NO: 36:

```
Ser Ser Cys Xaa Xaa Xaa Xaa Xaa Xaa Xaa Xaa Cys Gly Ser Arg Ser
1               5                   10                  15
Thr Xaa Xaa Xaa Xaa Xaa Xaa Xaa Xaa Thr Thr Arg
            20                  25
```

(2) INFORMATION FOR SEQ ID NO: 37:

(i) SEQUENCE CHARACTERISTICS:
        (A) LENGTH: 80 bases
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 37:

TCGAGTTGTN NKNNKNNKNN KNNKNNKNNK NNKTGTGGAT 40

CTAGATCCAC AMNMNNNMNN MNNMNNMNNM NNMNNACAAC 80

(2) INFORMATION FOR SEQ ID NO: 38:

(i) SEQUENCE CHARACTERISTICS:
        (A) LENGTH: 45 amino acids
        (B) TYPE: amino acid
        (D) TOPOLOGY: unknown (ii) MOLECULE TYPE: peptide (xi) SEQUENCE DESCRIPTION: SEQ ID NO: 38:

Ser Ser Phe Asp Gln Gln Asp Trp Asp Tyr Ser Ile Ala Glu Lys Met
1               5                   10                  15

His Pro Ile Arg Pro Gly Phe Arg Glu Leu Pro Pro Leu Pro Pro Ser
            20                  25                  30

Arg Ala Ser Phe Gly Gly Gly Ala Ser Arg Pro Ser Arg
            35                  40                  45

(2) INFORMATION FOR SEQ ID NO: 39:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO: 39:

Ser Thr Asn Val Trp Val Thr Gly Ser Val Ile Ala Arg Gly Ala Gln
1               5                   10                  15

Ser Arg Pro Leu Pro Ile Pro Pro Glu Thr Arg Pro Ser Arg
            20                  25                  30

(2) INFORMATION FOR SEQ ID NO: 40:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO: 40:

Ser Thr Ala Pro Trp Gly Leu Arg Val Ala His Glu Gly Gly Val Leu
1               5                   10                  15

Lys Arg Pro Leu Pro Ile Pro Pro Val Thr Arg Pro Ser Arg
            20                  25                  30

(2) INFORMATION FOR SEQ ID NO: 41:

(i) SEQUENCE CHARACTERISTICS:
        (A) LENGTH: 45 amino acids
        (B) TYPE: amino acid
        (D) TOPOLOGY: unknown (ii) MOLECULE TYPE: peptide (xi) SEQUENCE DESCRIPTION: SEQ ID NO: 41:

Ser Ser Ser Gly Tyr Val Val Pro Lys Arg Leu Gly Asp Met Arg Glu
1               5                   10                  15

```
Tyr Asn Ala His Pro Gly Leu His Val Pro Pro Asn Ser Pro Leu Pro
         20                  25                  30

Pro Leu Pro Thr His Leu Gln Ser Ser Arg Pro Ser Arg
         35                  40                  45

(2) INFORMATION FOR SEQ ID NO: 42:

(i) SEQUENCE CHARACTERISTICS:
        (A) LENGTH: 44 amino acids
        (B) TYPE: amino acid
        (D) TOPOLOGY: unknown (ii) MOLECULE TYPE: peptide (xi) SEQUENCE DESCRIPTION: SEQ ID NO: 42:

Ser Ser Arg Gly Glu Gly Asn Asn Ile Ile Ser Ser Arg Pro Phe Leu
1               5                  10                  15

Ser Asn Ser Asp Pro Gly Val Ser Asn Lys Leu Thr Gly Arg Gly Pro
         20                  25                  30

Leu Pro Pro Leu Pro Asn Asp Ser Arg Pro Ser Arg
         35                  40

(2) INFORMATION FOR SEQ ID NO: 43:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 43:

Ser Thr Ala Val Ser Phe Arg Phe Met Pro Gly Gly Gly Gly Ala Phe
1               5                  10                  15

Tyr Ser Thr Arg Pro Val Pro Pro Ile Thr Arg Pro Ser Arg Thr
         20                  25                  30

(2) INFORMATION FOR SEQ ID NO: 44:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 44:

Ser Thr Ala His Ser Leu Trp Asp Trp Gly Thr Phe Ser Gly Val Ser
1               5                  10                  15

His Lys Ser Arg Leu Pro Pro Leu Pro Thr Arg Pro Ser Arg Thr
         20                  25                  30

(2) INFORMATION FOR SEQ ID NO: 45:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (xi) SEQUENCE DESCRIPTION: SEQ ID NO: 45:

Pro Gly Tyr Ala Arg Ile Val Ser Tyr Arg Phe Arg Ala Leu Pro Ser
1               5                  10                  15

Pro Pro Ser Ala Ser Arg Pro Ser Arg
```

```
                20                  25
```

(2) INFORMATION FOR SEQ ID NO: 46:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO: 46:

```
Ser Thr Asn Asp Val Asp Trp Met His Met Trp Asn Ser Gly Gly Pro
1               5                   10                  15
His Arg Arg Leu Pro Pro Thr Pro Ala Thr Arg Pro Ser Arg
                20                  25                  30
```

(2) INFORMATION FOR SEQ ID NO: 47:

(i) SEQUENCE CHARACTERISTICS:
        (A) LENGTH: 45 amino acids
        (B) TYPE: amino acid
        (D) TOPOLOGY: unknown (ii) MOLECULE TYPE: peptide (xi) SEQUENCE DESCRIPTION: SEQ ID NO: 47:

```
Ser Ser Asp Asn Trp Ala Arg Arg Val His Ala Ser Glu Leu Ile Tyr
1               5                   10                  15
Thr Asp Leu Ser Pro Gly Ile Leu Leu Ala Gln Arg Gln Leu Pro Pro
                20                  25                  30
Thr Pro Gly Arg Asp Pro Ser His Ser Arg Pro Ser Arg
                35                  40                  45
```

(2) INFORMATION FOR SEQ ID NO: 48:

(i) SEQUENCE CHARACTERISTICS:
        (A) LENGTH: 45 amino acids
        (B) TYPE: amino acid
        (D) TOPOLOGY: unknown (ii) MOLECULE TYPE: peptide (xi) SEQUENCE DESCRIPTION: SEQ ID NO: 48:

```
Ser Ser Glu Ser Pro Leu Met Tyr Asn Arg Val Gly Ala Leu Gln Ser
1               5                   10                  15
Leu Thr Ser Val Pro Gly Ser Met Met His Phe Ala Leu Gln Arg Arg
                20                  25                  30
Leu Pro Arg Thr Pro Pro Ala Ser Arg Pro Ser Arg
                35                  40                  45
```

(2) INFORMATION FOR SEQ ID NO: 49:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (xi) SEQUENCE DESCRIPTION: SEQ ID NO: 49:

```
Ser Thr Arg Trp Ser His Ser Trp Pro Gly Tyr Val Gly Gly Ala Asn
1               5                   10                  15
Pro Ser Pro Ala Thr Arg Pro Leu Pro Thr Arg Pro Ser Arg Thr Val
                20                  25                  30
```

Glu Ser Cys
       35

(2) INFORMATION FOR SEQ ID NO: 50:

(i) SEQUENCE CHARACTERISTICS:
        (A) LENGTH: 50 amino acids
        (B) TYPE: amino acid
        (D) TOPOLOGY: unknown (ii) MOLECULE TYPE: peptide (xi) SEQUENCE DESCRIPTION: SEQ ID NO: 50:

Ser Arg Tyr Asn Asp Leu Gly Thr Arg Pro Val Ser Glu Val Ile Lys
1               5                  10                  15

Tyr Asp Tyr Phe Pro Gly Tyr Ser Gln His Val Ile Thr Pro Asp Gly
                20                  25                  30

Ser Tyr Ser Thr Arg Pro Leu Pro Ser Arg Pro Ser Arg Thr Val Glu
            35                  40                  45

Ser Cys
    50

(2) INFORMATION FOR SEQ ID NO: 51:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (xi) SEQUENCE DESCRIPTION: SEQ ID NO: 51:

Pro Gly Arg Ile Leu Leu Leu Pro Ser Glu Pro Arg Thr Phe Tyr Asn
1               5                  10                  15

Tyr Gly His Asp Ser Arg Pro Ser Arg
                20                  25

(2) INFORMATION FOR SEQ ID NO: 52:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (xi) SEQUENCE DESCRIPTION: SEQ ID NO: 52:

Ser Thr Met Tyr Gly Val Ser Trp Leu Ser Ser Gly Ser Gly Gly Ile
1               5                  10                  15

Leu Ala Pro Pro Val Pro Pro Arg Asn Thr Arg Pro Ser Arg
                20                  25                  30

(2) INFORMATION FOR SEQ ID NO: 53:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 53:

Ser Ser Cys Thr Glu Lys Thr Val Ser Gly Trp Cys Gly Ser Arg Ser
1               5                  10                  15

```
Thr Arg Pro Leu Pro Ile Leu Pro Arg Thr Thr Arg Pro Ser Arg
            20                  25                  30
```

(2) INFORMATION FOR SEQ ID NO: 54:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 54:

```
Ser Ser Cys Met Leu Pro Thr Asp Gly Trp Gln Cys Gly Ser Arg Ser
1               5                  10                  15
Thr Pro Arg Pro Leu Pro Met Leu Pro Thr Thr Arg Pro Ser Arg
            20                  25                  30
```

(2) INFORMATION FOR SEQ ID NO: 55:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 55:

```
Ser Ser Cys Asp Gly Thr Gln Phe Arg Leu Asn Cys Gly Ser Arg Ser
1               5                  10                  15
Thr Asn Arg Pro Leu Pro Met Ile Pro Thr Thr Arg Pro Ser Arg
            20                  25                  30
```

(2) INFORMATION FOR SEQ ID NO: 56:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 56:

```
Ser Ser Cys Met Gln Gly Gln Ala Gly Leu Lys Cys Gly Ser Arg Ser
1               5                  10                  15
Thr Arg Pro Leu Pro Ser Leu Pro Ile Thr Thr Arg Pro Ser Arg
            20                  25                  30
```

(2) INFORMATION FOR SEQ ID NO: 57:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 57:

```
Ser Ser Cys Tyr Arg Glu Lys Asp Thr Trp Gly Cys Gly Ser Arg Ser
1               5                  10                  15
Thr Ser Arg Pro Leu Pro Ser Leu Pro Thr Thr Arg Pro Ser Arg
            20                  25                  30
```

(2) INFORMATION FOR SEQ ID NO: 58:

(i) SEQUENCE CHARACTERISTICS:

(A) LENGTH: 31 amino acids
(B) TYPE: amino acid
(D) TOPOLOGY: unknown (ii) MOLECULE TYPE: peptide (xi) SEQUENCE DESCRIPTION: SEQ ID NO: 58:

Ser Ser Cys Leu Phe Glu Gln Gly Ala Gly Thr Cys Gly Ser Arg Ser
1               5                   10                  15

Thr Arg Ser Leu Pro Pro Leu Pro Pro Thr Thr Arg Pro Ser Arg
            20                  25                  30

(2) INFORMATION FOR SEQ ID NO: 59:

(i) SEQUENCE CHARACTERISTICS:
        (A) LENGTH: 44 amino acids
        (B) TYPE: amino acid
        (D) TOPOLOGY: unknown (ii) MOLECULE TYPE: peptide (xi) SEQUENCE DESCRIPTION: SEQ ID NO: 59:

Ser Ser Cys Asp Thr Gly Arg Ile Ala Pro Gly Cys Gly Ser Arg Ser
1               5                   10                  15

Thr Pro Arg Pro Leu Pro Leu Ile Pro Thr Thr Pro Arg Ser Thr Asn
            20                  25                  30

Leu Asn Leu Thr Ser Thr Thr Thr Arg Pro Ser Arg
            35                  40

(2) INFORMATION FOR SEQ ID NO: 60:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 60:

Ser Ser Cys Gly Leu Asp Asn Ala Ala Lys Thr Cys Gly Ser Arg Ser
1               5                   10                  15

Thr Arg Pro Leu Pro Pro Thr Pro Leu Thr Thr Arg Pro Ser Arg
            20                  25                  30

(2) INFORMATION FOR SEQ ID NO: 61:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 61:

Ser Ser Cys Ser Arg Ala His Glu Thr Glu Met Cys Gly Ser Arg Ser
1               5                   10                  15

Thr Arg Pro Gln Pro Pro Pro Ile Thr Thr Arg Pro Ser Arg
            20                  25                  30

(2) INFORMATION FOR SEQ ID NO: 62:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 62:

Arg Ser Thr Pro Arg Pro Leu Pro Met Leu Pro Thr Thr Arg
1               5                   10

(2) INFORMATION FOR SEQ ID NO: 63:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 63:

Gly Ile Leu Ala Pro Pro Val Pro Pro Arg Asn Thr Arg
1               5                   10

(2) INFORMATION FOR SEQ ID NO: 64:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 64:

Val Leu Lys Arg Pro Leu Pro Ile Pro Pro Val Thr Arg
1               5                   10

(2) INFORMATION FOR SEQ ID NO: 65:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 65:

Gly Pro His Arg Arg Leu Pro Pro Thr Pro Ala Thr Arg
1               5                   10

(2) INFORMATION FOR SEQ ID NO: 66:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 66:

Ala Asn Pro Ser Pro Ala Thr Arg Pro Leu Pro Thr Arg
1               5                   10

(2) INFORMATION FOR SEQ ID NO: 67:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 67:

```
Arg Ser Thr Pro Arg Pro Leu Pro Pro Leu Pro Thr Thr Arg
1               5                   10
```

(2) INFORMATION FOR SEQ ID NO: 68:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO: 68:

```
Gly Thr Val Glu Pro Val Pro Pro Val Pro Pro Arg Arg Pro
1               5                   10                  15
Glu Ser Ala
```

(2) INFORMATION FOR SEQ ID NO: 69:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO: 69:

```
Lys Ile Ser Pro Pro Thr Pro Lys Pro Arg Pro Pro Arg Pro Leu Pro
1               5                   10                  15
Val
```

(2) INFORMATION FOR SEQ ID NO: 70:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 70:

```
Leu Ala Pro Pro Lys Pro Pro Leu Pro Glu Gly Glu Val
1               5                   10
```

(2) INFORMATION FOR SEQ ID NO: 71:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /note= "X = any amino
            acid residue except cysteine"

(ix) FEATURE:
        (A) NAME/KEY: Modified-site
        (B) LOCATION: 5..6
        (D) OTHER INFORMATION: /note= "X = a hydrophobic
            amino acid residue"

(xi) SEQUENCE DESCRIPTION: SEQ ID NO: 71:

```
Arg Xaa Leu Pro Xaa Xaa Pro
1               5
```

(2) INFORMATION FOR SEQ ID NO: 72:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 72:

```
Pro Gly Phe Arg Glu Leu Pro Pro Leu Pro Pro Ser Arg
1               5                   10
```

(2) INFORMATION FOR SEQ ID NO: 73:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 73:

```
Ala Gln Ser Arg Pro Leu Pro Ile Pro Pro Glu Thr Arg
1               5                   10
```

(2) INFORMATION FOR SEQ ID NO: 74:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 74:

```
Pro Pro Asn Ser Pro Leu Pro Pro Leu Pro Thr His Leu
1               5                   10
```

(2) INFORMATION FOR SEQ ID NO: 75:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 75:

```
Thr Gly Arg Gly Pro Leu Pro Pro Leu Pro Asn Asp Ser
1               5                   10
```

(2) INFORMATION FOR SEQ ID NO: 76:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 76:

```
Tyr Ser Thr Arg Pro Val Pro Pro Ile Thr Arg Pro Ser
1               5                   10
```

(2) INFORMATION FOR SEQ ID NO: 77:

(i) SEQUENCE CHARACTERISTICS:

(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 77:

Ser His Lys Ser Arg Leu Pro Pro Leu Pro Thr Arg Pro
1               5                   10

(2) INFORMATION FOR SEQ ID NO: 78:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 78:

Tyr Arg Phe Arg Ala Leu Pro Ser Pro Pro Ser Ala Ser
1               5                   10

(2) INFORMATION FOR SEQ ID NO: 79:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 79:

Leu Ala Gln Arg Gln Leu Pro Pro Thr Pro Gly Arg Asp
1               5                   10

(2) INFORMATION FOR SEQ ID NO: 80:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 80:

Ala Leu Gln Arg Arg Leu Pro Arg Thr Pro Pro Pro Ala
1               5                   10

(2) INFORMATION FOR SEQ ID NO: 81:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 81:

Pro Ala Thr Arg Pro Leu Pro Thr Arg Pro Ser Arg Thr
1               5                   10

(2) INFORMATION FOR SEQ ID NO: 82:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO: 82:

Tyr Ser Thr Arg Pro Leu Pro Ser Arg Pro Ser Arg Thr
1               5                   10

(2) INFORMATION FOR SEQ ID NO: 83:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 83:

Xaa Pro Gly Arg Ile Leu Leu Leu Pro Ser Glu Pro Arg
1               5                   10

(2) INFORMATION FOR SEQ ID NO: 84:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 84:

Ser Gly Gly Ile Leu Ala Pro Pro Val Pro Pro Arg Asn
1               5                   10

(2) INFORMATION FOR SEQ ID NO: 85:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 85:

Arg Ser Thr Arg Pro Leu Pro Ile Leu Pro Arg Thr Thr
1               5                   10

(2) INFORMATION FOR SEQ ID NO: 86:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 86:

Ser Thr Pro Arg Pro Leu Pro Met Leu Pro Thr Thr Arg
1               5                   10

(2) INFORMATION FOR SEQ ID NO: 87:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 87:

Ser Thr Asn Arg Pro Leu Pro Met Ile Pro Thr Thr Arg
1               5                   10

(2) INFORMATION FOR SEQ ID NO: 88:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 88:

Arg Ser Thr Arg Pro Leu Pro Ser Leu Pro Ile Thr Thr
1               5                   10

(2) INFORMATION FOR SEQ ID NO: 89:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 89:

Ser Thr Ser Arg Pro Leu Pro Ser Leu Pro Thr Thr Arg
1               5                   10

(2) INFORMATION FOR SEQ ID NO: 90:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 90:

Arg Ser Thr Arg Ser Leu Pro Pro Leu Pro Pro Thr Thr
1               5                   10

(2) INFORMATION FOR SEQ ID NO: 91:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 91:

Arg Ser Thr Arg Gln Leu Pro Ile Pro Pro Thr Thr Thr
1               5                   10

(2) INFORMATION FOR SEQ ID NO: 92:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 92:

Ser Thr Pro Arg Pro Leu Pro Leu Ile Pro Thr Thr Pro
1               5                   10

(2) INFORMATION FOR SEQ ID NO: 93:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 93:

Arg Ser Thr Arg Pro Leu Pro Pro Thr Pro Leu Thr Thr
1               5                   10

(2) INFORMATION FOR SEQ ID NO: 94:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 94:

Arg Ser Thr Arg Pro Gln Pro Pro Pro Ile Thr Thr
1               5                   10

(2) INFORMATION FOR SEQ ID NO: 95:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO: 95:

Arg Pro Leu Pro Met Leu Pro
1               5

(2) INFORMATION FOR SEQ ID NO: 96:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 5
        (D) OTHER INFORMATION: /note= "X = Pro or Met"

(xi) SEQUENCE DESCRIPTION: SEQ ID NO: 96:

Arg Pro Leu Pro Xaa Leu Pro
1               5

(2) INFORMATION FOR SEQ ID NO: 97:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 97:

Arg Ser Thr Pro
1

(2) INFORMATION FOR SEQ ID NO: 98:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 98:

Arg Ser Thr Pro Ala Pro Pro Val Pro Pro Arg Thr Thr Arg
1               5                   10

(2) INFORMATION FOR SEQ ID NO: 99:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

AGCGTAACGA TCTCCCG                                                17

(2) INFORMATION FOR SEQ ID NO: 100:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 100:

TTCACCTCGA AAGCAAGCTG                                             20

(2) INFORMATION FOR SEQ ID NO: 101:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 101:

CCTCATAGTT AGCGTAACG                                              19

(2) INFORMATION FOR SEQ ID NO: 102:

(i) SEQUENCE CHARACTERISTICS:
        (A) LENGTH: 16 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

AGCGTAACGA TCTAAA                                                 16

(2) INFORMATION FOR SEQ ID NO: 103:

(i) SEQUENCE CHARACTERISTICS:

(A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO: 103:

Lys Ser Gly Ser Gly
1               5

(2) INFORMATION FOR SEQ ID NO: 104:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 104:

Gly Ser Gly Ser
1

(2) INFORMATION FOR SEQ ID NO: 105:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO: 105:

Glu Gln Lys Leu Ile Ser Glu Glu Asp Leu Asn
1               5                   10

(2) INFORMATION FOR SEQ ID NO: 106:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 106:

Ser Ser Cys Asp His Thr Leu Gly Leu Gly Trp Cys Gly Ser Arg Ser
1               5                   10                  15

Thr Arg Gln Leu Pro Ile Pro Pro Thr Thr Thr Arg Pro Ser Arg
                20                  25                  30